US011559504B2

(12) United States Patent
Kester et al.

(10) Patent No.: US 11,559,504 B2
(45) Date of Patent: Jan. 24, 2023

(54) CERAMIDE NANOLIPOSOMES, COMPOSITIONS AND METHODS OF USING FOR IMMUNOTHERAPY

(71) Applicants: THE PENN STATE RESEARCH FOUNDATION, University Park, PA (US); THE CURATORS OF THE UNIVERSITY OF MISSOURI, Columbia, MO (US)

(72) Inventors: Mark Kester, Harrisburg, PA (US); Kevin Staveley-O'Carroll, Columbia, MO (US); Guangfu Li, Columbia, MO (US)

(73) Assignees: THE PENN STATE RESEARCH FOUNDATION, University Park, PA (US); THE CURATORS OF THE UNIVERSITY OF MISSOURI, Columbia, MO (US)

( * ) Notice: Subject to any disclaimer, the term of this patent is extended or adjusted under 35 U.S.C. 154(b) by 320 days.

(21) Appl. No.: 16/615,607

(22) PCT Filed: Jun. 1, 2018

(86) PCT No.: PCT/US2018/035594
§ 371 (c)(1),
(2) Date: Nov. 21, 2019

(87) PCT Pub. No.: WO2018/222989
PCT Pub. Date: Dec. 6, 2018

(65) Prior Publication Data
US 2020/0170970 A1 Jun. 4, 2020

Related U.S. Application Data

(60) Provisional application No. 62/514,536, filed on Jun. 2, 2017.

(51) Int. Cl.
*A61K 31/164* (2006.01)
*A61P 35/00* (2006.01)
(Continued)

(52) U.S. Cl.
CPC ............ *A61K 31/164* (2013.01); *A61K 9/127* (2013.01); *A61K 35/17* (2013.01); *A61P 35/00* (2018.01);
(Continued)

(58) Field of Classification Search
CPC ...................................................... A61K 31/64
See application file for complete search history.

(56) References Cited

U.S. PATENT DOCUMENTS 7,488,802 B2   2/2009   Collins et al.
7,521,051 B2   4/2009   Collins et al.
(Continued)

FOREIGN PATENT DOCUMENTS

CN   104922067 A    9/2015
EP     1767216 A1    3/2007
(Continued)

OTHER PUBLICATIONS

Adiseshaiah et al., "Synergistic combination therapy with nanoliposomal C6-ceramide and vinblastine is associated with autophagy dysfunction in hepatocarcinoma and colorectal cancer models", Cancer Letters, vol. 337, pp. 254-265, Apr. 29, 2013.
(Continued)

*Primary Examiner* — Benjamin J Packard
(74) *Attorney, Agent, or Firm* — McKee, Voorhees & Sease, PLC

(57) ABSTRACT

Methods and compositions for treating cancer are provided. Compositions comprising ceramide nanoliposomes are administered to a subject in need of such treatment. The composition administration also enhances immunotherapy.

(Continued)

Further administering compositions in combination with tumor antigen specific T-cells, and/or compositions in combination with tumor antigen expressing cells, and/or said compositions in combination with antagonists of PD-1 provides for enhanced results. Administration of the compositions provides for effective treatment of tumors including regression and eradication of established tumors.

16 Claims, 32 Drawing Sheets

Specification includes a Sequence Listing.

(51) Int. Cl.
```
A61K 9/127      (2006.01)
A61K 35/17      (2015.01)
C07K 16/28      (2006.01)
A61K 38/00      (2006.01)
A61K 39/00      (2006.01)
```
(52) U.S. Cl.
CPC .......... *C07K 16/2827* (2013.01); *A61K 38/00* (2013.01); *A61K 2039/5158* (2013.01); *A61K 2039/55555* (2013.01)

(56) References Cited

U.S. PATENT DOCUMENTS

```
8,008,449  B2   8/2011   Korman et al.
8,168,757  B2   5/2012   Finnefrock et al.
8,354,509  B2   1/2013   Carven et al.
8,747,891  B2   6/2014   Kester et al.
2011/0271358 A1 11/2011  Freeman et al.
2018/0092901 A1  4/2018  Denker et al.
```

FOREIGN PATENT DOCUMENTS

```
JP    9110722     A    4/1997
WO    2004004771  A1   1/2004
WO    2004056875  A1   7/2004
WO    2004072286  A1   8/2004
WO    2016141218  A1   9/2016
```

OTHER PUBLICATIONS

European Patent Office in connection with PCT/US2018/035594 filed Jun. 1, 2018, "Extended European Search Report", 11 pages, dated Feb. 17, 2021.
Tagaram et al., "Nanoliposomal ceramide prevents in vivo growth of hepatocellular carcinoma", Gut, vol. 60, pp. 695-701, 2011.
Avella et al., "Regression of Established Hepatocellular Carcinoma is Induced by Chemo-immunotherapy in an Orthotopic Murine Model", Hepatology, vol. 55(1), pp. 141-152, Jan. 2012.
Breous et al., "Potential of immunotherapy for hepatocellular carcinoma", Journal of Hepatology, vol. 54, pp. 830-834, 2011.
Duluc et al., "Tumor-associated leukemia inhibitory factor and IL-6 skew monocyte differentiation into tumor-associated macrophage-like cells", Blood, vol. 110, No. 13, pp. 4319-4330, Dec. 15, 2007.
Emens, Leisha A., "Chemoimmunotherapy", Cancer J., vol. 16(4), pp. 295-303, Jul. 1, 2011.
Fleetwood et al., "GM-CSF- and M-CSF-dependent macrophage phenotypes display differential dependence on Type I interferon signaling", Journal of Leukocyte Biology, vol. 86, pp. 411-421, Aug. 2009.
Forner et al., "Hepatocellular carcinoma", The Lancet, vol. 379, pp. 1245-1255, Mar. 31, 2012.
Gajewski et al., "Cancer Immunotherapy: Editorial overview", Current Opinion in Immunology, vol. 25, pp. 259-260, 2013.
Gajewski et al., "Innate and adaptive immune cells in the tumor microenvironment", Nature Immunology, vol. 14, No. 10, pp. 1014-1022, Oct. 2013.
Greten et al., "Current concepts of immune based treatments for patients with HCC: from basic science to novel treatment approaches", Gut., vol. 64(5), pp. 842-848, May 2015.
Held et al., "T antigen expression and tumorigenesis in transgenic mice containing a mouse major urinary protein/SV40 T antigen hybrid gene", The EMBO Journal, vol. 8, No. 1, pp. 183-191, 1989.
Herz et al., "Acid sphingomyelinase is a key regulator of cytotoxic granule secretion by primary T lymphocytes", Nature Immunology, vol. 10, No. 7, pp. 761-773 Jul. 2009.
Jiang et al., "Combinatorial therapies improve the therapeutic efficacy of nanoliposomal ceramide for pancreatic cancer", Cancer Biology & Therapy, vol. 12:7, pp. 574-585, Oct. 1, 2011.
Kester et al., "Preclinical development of a C6-ceramide NanoLiposome, a novel sphingolipid therapeutic", Biol. Chem., vol. 396(6-7), pp. 737-747, Mar. 3, 2015.
Kochenderfer et al., "Eradication of B-lineage cells and regression of lymphoma in a patient treated with autologous T cells genetically engineered to recognize CD19", Blood, vol. 116(20), pp. 4099-4102, Jul. 20, 2010.
Kochenderfer et al., "Chemotherapy—Refractory Diffuse Large B-Cell Lymphoma and Indolent B-Cell Malignancies Can Be Effectively Treated with Autologous T Cells Expressing an Anti-CD19 Chimeric Antigen Receptor", J. Clin. Oncol., vol. 33, No. 6, pp. 540-549, 2014.
Li et al., "Successful Chemoimmunotherapy against Hepatocellular Cancer in a Novel Murine Mode", J. Hepatol., vol. 66(1), pp. 75-85, Jan. 2017.
Liu et al., "Immune-based Therapy Clinical Trials in Hepatocellular Carcinoma", Journal Clinical & Cellular Immunology, vol. 6:6, 9 pages, Dec. 10, 2015.
Liu et al., "Targeting of survivin by nanoliposomal ceramide induces complete remission in a rat model of NK-LGL leukemia", Blood, vol. 116, No. 20, pp. 4192-4201, Nov. 18, 2010.
Mapara et al., "Tolerance and Cancer: Mechanisms of Tumor Evasion and Strategies for Breaking Tolerance", Journal of Clinical Oncology: Biology of Neoplasia, vol. 22, No. 6, pp. 1136-1151 Mar. 15, 2004.
Martinez et al., "Transcriptional Profiling of the Human Monocyte-to-Macrophage Differentiation and Polarization: New Molecules and Patterns of Gene Expression", Journal of Immunology, vol. 177, pp. 7303-7311, 2006.
Melief et al., "Strategies for Immunotherapy of Cancer", Advances in Immunology, vol. 75, pp. 235-282, 2000.
Moghimi et al., "Modulation of murine liver macrophage clearance of liposomes by diethylstilbestrol. The effect of visicle surface charge and a role for the complement receptor Mac-1 (CD11b/CD18) of newly recruited macrophages in liposome recognition", Journal of Controlled Release, vol. 78, pp. 55-65, 2002.
Morad et al., "Ceramide-orchestrated signalling in cancer cells", Nature Reviews, vol. 13, pp. 51-65, Jan. 2013.
Morales et al., "Springolipids and cell death", Apoptosis, vol. 12, pp. 923-939, 2007.
Mueller, Kristen L., "Realizing the Promise", Science, vol. 348, pp. 54-55, 2005.
Niu et al., "Combination treatment with comprehensive cryoablation and immunotherapy in metastatic hepatocellular cancer", World Journal of Gastroenterology, vol. 19(22), pp. 3473-3480, Jun. 14, 2013.
Baselga et al., "Pembrolizumab Superior to Ipilimumab in Melanoma", Cancer Discovery, vol. 5, 1 page Jun. 2015.
Pettus et al., "Ceramide in apoptosis: an overview and current perspectives", Biochimica et Biophysica Acta, vol. 1585, pp. 114-125, Oct. 29, 2002.
Pritzl et al., "A Ceramide Analogue Stimulates Dendritic Cells to Promote T Cell Responses upon Virus Infections", J. Immunol., vol. 194, pp. 4339-4349, Feb. 24, 2015.
Rhoads et al., "Satellite cell-mediated angiogenesis in vitro coincides with a functional hypoxia-inducible factor pathway". Am. J. Physiol Cell Physiol., vol. 296(6), pp. C1321-C1328, Jun. 2009.

(56) References Cited

OTHER PUBLICATIONS

Ribas et al., "Combining Cancer Immunotherapy and Targeted Therapy", Curr Opin Immunol, vol. 25(2), 11 pages, Apr. 2013.

Robbins et al., "A Pilot Trial Using Lymphocytes Genetically Engineered with an NY-ESO-1-Reactive T Cell receptor: Long-term Follow-up and Correlates with Response", Clin Cancer Res, vol. 21(5), pp. 1019-1027, Mar. 1, 2015.

Sallusto et al., "Ceramide Inhibits Antigen Uptake and Presentation by Dendritic Cells", J. Exp. Med., vol. 184, pp. 2411-2416, Dec. 1996.

Schneider et al., "Adaptive immunity suppresses formation and progression of diethylnitrosamine-induced liver cancer", Gut., vol. 61(12), pp. 1733-1743, Dec. 2012.

Sharma et al., "Novel cancer immunotherapy agents with survival benefit: recent successes and next steps", Nat Rev Cancer, vol. 11(11), pp. 805-812, Aug. 23, 2012.

Sica et al., "Macrophage Plasticity and Polarization in Liver homeostasis and Pathology", Hepatology, vol. 59, No. 5, pp. 2035-2043, May 2014.

Spiegel et al., "The outs and the ins of sphingosine-1-phosphate in immunity", Nat Rev Immunol, vol. 11(6), pp. 403-415, Jun. 2011.

Staveley-O'Carroll et al., "In Vivo Ligation of CD40 Enhances Priming Against the Endogenous Tumor Antigen and Promotes CD8+ T Cell Effector Function in SV40 T Antigen Transgenic Mice", The Journal of Immunology, vol. 171, pp. 697-707, 2003.

Stoffel et al., "Ceramide-independent CD28 and TCR signaling but reduced IL-2 secretion in T cells of acid sphingomyelinase-deficient mice", Eur. J Immunol., vol. 28, pp. 874-880, 1998.

Tran et al., "T-Cell Transfer Therapy Targeting Mutant KRAS in Cancer", New England Journal of Medicine, vol. 375:23, pp. 2255-2262, Dec. 8, 2016.

Vigneron, Nathalie, "Human Tumor Antigens and Cancer Immunotherapy", Hindawi Publishing Corporation, BioMed Research International, vol. 2015, Article ID 948501, 17 pages, Mar. 3, 2015.

Watters et al., "Targeting Glucosylceramide Synthase Synergizes with C6-Ceramide Nanoliposomes to Induce Apoptosis in NK Leukemia", Leuk Lymphoma, vol. 54(6), pp. 1288-1296, Jun. 2013.

Zhang et al., "ROS play a critical role in the differentiation of alternatively activated macrophages and the occurrence of tumor-associated macrophages", Cell Research, vol. 23, pp. 898-914, Apr. 26, 2013.

Zolnik et al., "Rapid Distribution of Liposomal Short-Chain Ceramide in Vitro and in Vivo", Drug Metabolism and Disposition, vol. 36, No. 8, pp. 1709-1715, May 15, 2008.

Zou, Weiping, "Immunosuppressive Networks in the Tumour Environment and Their Therapeutic Relevance", Nature Reviews, vol. 5, pp. 263-274 Apr. 2005.

Tagaram, et al., "Nanoliposomal ceramide prevents in vivo growth of hepatocellular carcinoma", Gut 2011; vol. 60, pp. 695-701 2011.

Saclier, et al., "Monocyte/macrophage interactions with myogenic precursor cells during skeletal muscle regeneration", The FEBS Journal, vol. 280, pp. 4118-4130 2013.

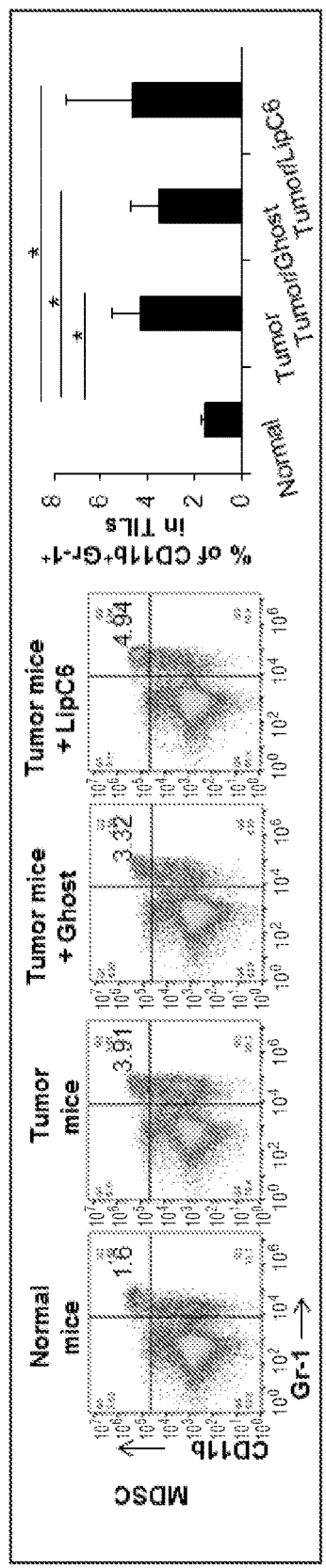
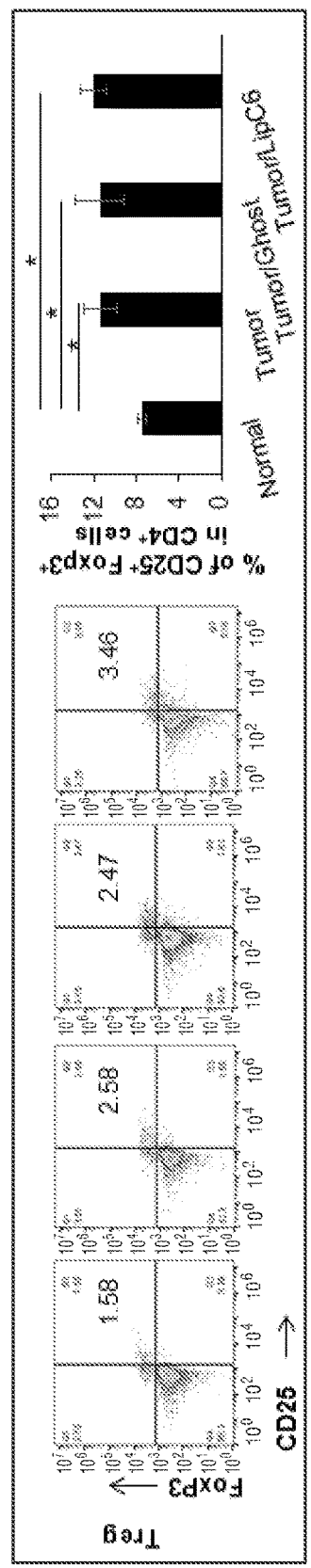
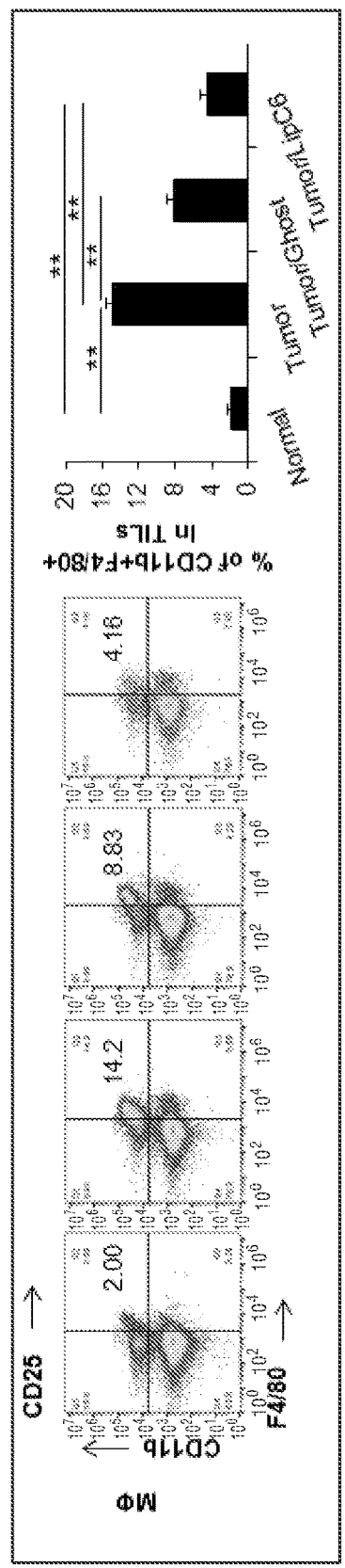
FIG. 3A
FIG. 3B
FIG. 3C

CERAMIDE NANOLIPOSOMES, COMPOSITIONS AND METHODS OF USING FOR IMMUNOTHERAPY

REFERENCE TO RELATED APPLICATIONS

This application claims priority to previously filed and application U.S. Ser. No. 62/514,536 filed Jun. 2, 2017, the contents of which are incorporated herein by reference in its entirety.

STATEMENT REGARDING FEDERALLY SPONSORED RESEARCH OR DEVELOPMENT

This invention was made with Government support under Grant Nos. CA164335 and CA208396 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 25, 2018 is named Kester_P12321WO00_SEQ_LISTING_ST25.txt and is 8,192 bytes in size.

BACKGROUND

Cancer is the leading cause of death world-wide. Manipulating the immune system for the treatment of established cancers has become part of the standard of care for several cancers[2-4]. Studies of immune checkpoints have led to important advances in the development of immunotherapeutic drugs[5,6]. For example, antibody-mediated blockade of cytotoxic T-lymphocyte-associated protein 4 (CTLA-4) and programmed death-1(PD-1) has been approved by the Food and Drug Administration (FDA) for the treatment of advanced melanoma, bladder, head and neck, and lung cancer[7]. These exciting advances in multiple cancer types support the translation of immunotherapies.

SUMMARY

Methods of treating cancer and compositions for same are provided. The method is to administration of a ceramide nanoliposome to a subject. The compositions comprise ceramide integrated into a nanoliposome to form ceramide nanoliposome. The ceramide may be a C2-26 ceramide and in one embodiment is a C6 ceramide. Administration of the ceramide nanoliposome may be combined with administration of tumor specific antigen T-cells, administration of tumor antigen expressing cells, administration of an antagonist of Programmed Death 1 protein, or administration of the ceramide nanoliposome combined with any combination of the above therapies.

DESCRIPTION

Figure 1A:
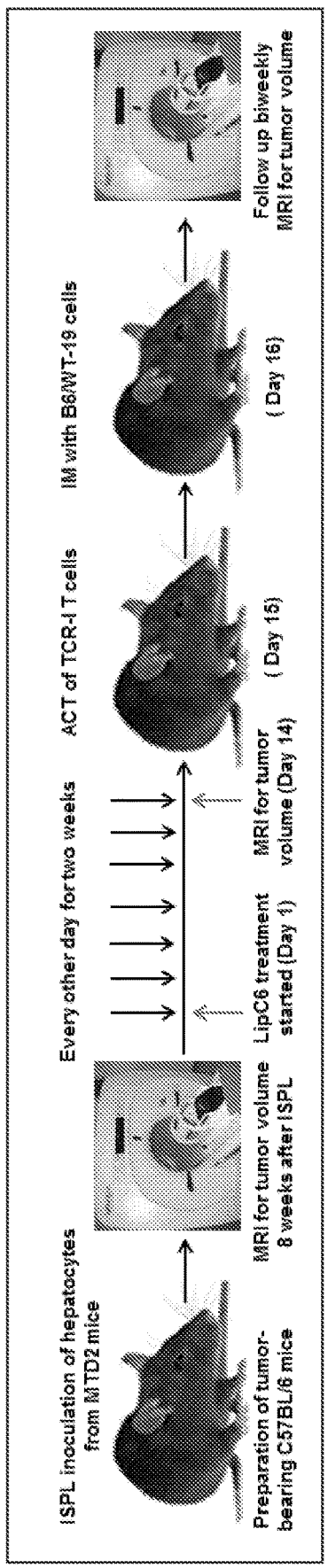
FIG. 1 shows photos (A) and C) and graphs (B, D) showing results of C6 nanoliposome (LipC6) injection in combination with TAS ACT and immunization that blocks tumor growth and effectively abolishes established HCC tumors. (A) Experimental design for therapeutic trial in TBMs. Mice bearing tumors detectable by MRI were randomly assigned to one of six groups and received the indicated administrations. (B) Mean tumor volume in mice over the experiment time is shown. Starting tumor volumes for each mouse was about 120 mm$^3$. (C) Representative images of MRI scans to detect tumors from the start to endpoints are shown. The tumors in images are shown by red dashed lines. (D) Waterfall plots showing the change in tumor volume at the experimental endpoint relative to the starting tumor volume for each mouse. In three vehicle-injected control groups, there was a progressive, substantial increase in tumor growth ranging from 600% to about 1500%. In three LipC6 injection-integrated groups, tumor growth was reduced, especially, combination of LipC6 with TCR-I and immunization resulted in about 10% reduction in tumor volume. n=6; error bars represent means±SD.

Methods of treating cancer are provided in which a ceramide nanoliposome is administered to a subject in need of treatment of cancer. The ceramide nanoliposome may comprise a C2-C26 ceramide, may in an embodiment be C6, C8, C10 and/or C12, and in another embodiment may comprise a C6 ceramide. Embodiments provide administration of the ceramide nanoliposome (CNL) may be combined with additional immunotherapy methods. An embodiment provides administration of CNL is combined with adoptive cell transfer therapy, which in further embodiments may provide the administration of the nanoliposome combined with administration to the subject of tumor specific antigen T-cells. Such tumor specific antigen T-cells may be naturally occurring or synthetic, including tumor cell receptors (TCR) or chimeric antigen receptors (CAR). Embodiments provide the CNL may be administered in combination with immunization, that is, administration of tumor antigen expressing cells. Additional embodiments provide administration of CNL is combined with administration of an antagonist of a Programmed Death 1 protein (PD-1). Still further embodiments provide administration of CNL combined with tumor specific antigen T-cells and/or administration of tumor antigen expressing cells and/or administration of an antagonist of PD-1. Methods described here result in enhancing immunotherapy. The methods provide for reduction of tumors, and further for eradication of existing tumors. Administration of the compositions may also provide for decease in population of PD-1+ TILs and/or decreased frequency of tumor associated macrophages. Increased M1 cytokine production and decreased M2 cytokine production is further provided.

Ceramide, a sphingolipid metabolite, has been demonstrated to be a powerful tumor suppressor[12-14] and may be involved in immune regulation[15]. Some studies indicate that ceramide is an essential component of T-cell receptor (TCR) signaling machinery. Pharmacologic or molecular inhibition of ceramide production impair TCR-induced interleukin-2 (IL-2) production and programmed cell death. Exogenous ceramide administration or sphingomyelinase-induced endogenous ceramide accumulation resulted in reconstitution of both responses[15]. However, it has not been used as a chemotherapeutic agent because of its cell impermeability and precipitation in aqueous solution. We developed a nanoliposome-loaded ceramide which in one example is a C6-ceremide (LipC6) to overcome this limitation and investigated its effects in mice with liver tumors. We have demonstrated that ceramide induces p-AKT-dependent apoptosis in human HCC cells in vitro and suppresses their xenograft tumor growth in vivo[16], exerting an inherent tumoricidal effect. In addition, we recently developed a clinically relevant murine model that mimics immune-tolerant human HCC[17]. Using this model, we are able to test if administration of ceramide can enhance antitumor immunotherapeutic strategies by significantly modulating the profound immunotolerant tumor microenvironment (TME) typical of HCC. Hepatocellular cancer (HCC) is now the second leading cause of cancer death with limited therapeutic options[1]. However, until now no immune-based therapeutic strategy has been successfully translated into an effective treatment for HCC9.

Figure 8:
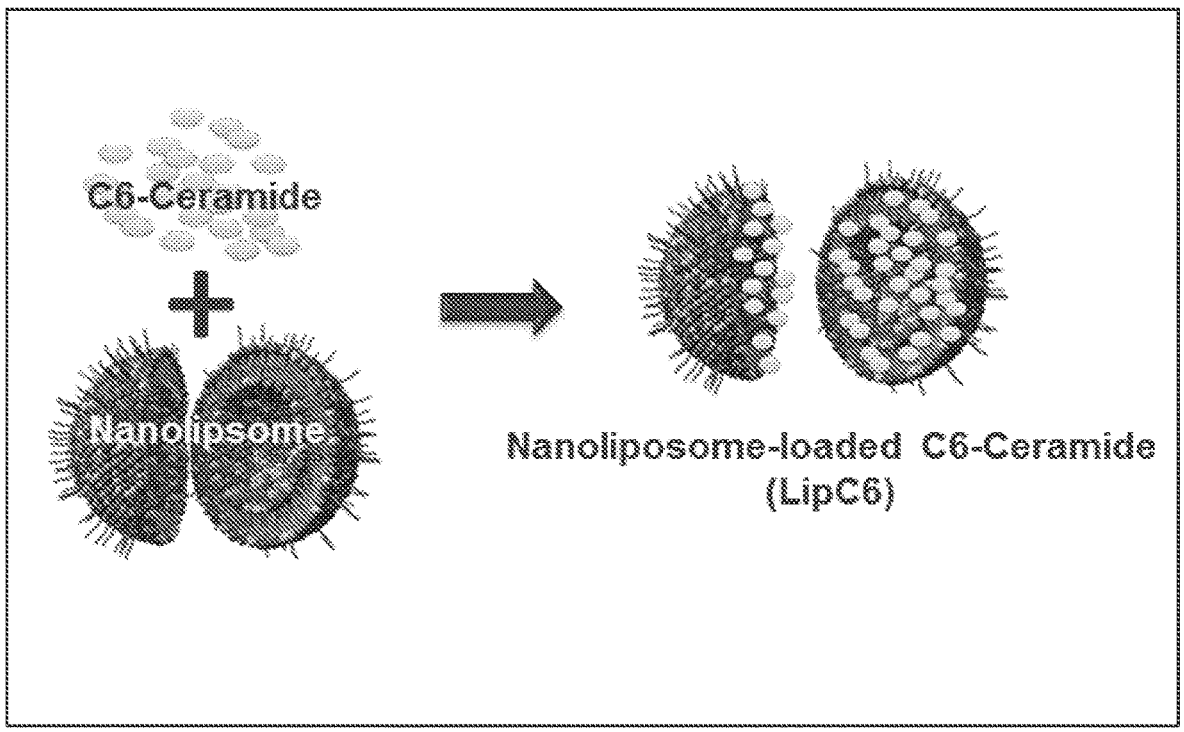
FIG. 8 is a schematic of a process of producing LipC6. Utilization of an advanced nanotechnology to synthesize nanoliposome-loaded C6-ceramid (LipC6). LipC6 is a stable, non-toxic nanoliposome formulation containing 15 mol % PEG and 30 mol % C6-Ceramide; hydrodynamic diameter is about 87 nm; zeta potential is −11±−1 mV; shelf life is more than 6 months.

A pro-apoptotic role of ceramide has been widely demonstrated in different cancers including in HCC[13,14]. Despite its key role in regulating tumor cell growth and death, its cell impermeability and precipitation in aqueous solution have limited ceramide's use as a therapeutic agent. Using nanotechnology advances in drug delivery, in one example we prepared a nanoliposome-loaded C6-ceramide (LipC6) (FIG. 8)[18]. This formulated LipC6 allows C6-ceramide to travel through the bloodstream and target tumor cells through enhanced cellular permeability and retention, facilitating its potential clinical use as a drug[18,19]. Moreover, extensive preclinical toxicological studies, including physiochemical characterization, and PK/PD analyses have been completed for LipC6 in two species (rats and beagles)[18]. In an example, an about 90 nm-sized, −8 mV, 15 molar percent PEG, 30 molar percent C6-ceramide nanoliposome has been shown to have a shelf life greater than 18 months. Ceramide is released from LipC6 by intrabilayer movement[20]. Specifically, in one example, the C6-ceramide partitions from the nano-platform to cells within the TME, including tumor cells and tumor associated macrophages (TAMs). Macrophages are key players in the homeostatic function of the liver. In response to changes in the local microenvironment, macrophages undergo polarized activation to M1 or M2[21]. M1 and M2 macrophages display different molecular phenotypes and release different cytokines, suppressing or promoting tumor growth. Reactive oxygen species (ROS) production has been demonstrated to be critical for macrophage differentiation[22]. With our clinically relevant HCC model, we now demonstrate that ceramide nanoliposomes mitigate the profound immunotolerant TME. This undocumented function is associated with modulation of TAMs through ROS signaling. Ceramide nanoliposome inherent tumoricidal effect combining with its ability to activate antitumor immunity results in the eradication of established tumors.

Ceramides are waxy lipid molecules made up of sphingosine and a fatty acid. Ceramide anionic liposomes that may be used here include the C2-C26 ceramides (N-acyl-sphingosine) or any combination thereof. An embodiment provides that the ceramide may be C6, C8, C10 and/or C12. In an embodiment the ceramide is C6. C6 ceramide is a sphingolipid metabolite that affects T-cell signaling. C6 ceramide is also known as N-hexanoyl-D-erythro-sphingosine and has the formula $C_{24}H_{47}NO_3$. See pubchem.ncbi.nlm.nih.gov/compound/C6_ceramide #section= Top.

The ceramide may be encapsulated in a nanoliposome formulation. By way of example, methods of preparation of nanoliposomes and pharmaceutical compositions of liposomes are described at Kester et al. U.S. Pat. No. 8,747,891, incorporated herein by reference in its entirety. The specific composition of the liposome can vary and may include additional beneficial molecules that can aid in the treatment or preventions of cancer or provide other benefits to the subject. The nanoliposome may further include compositions for immunotherapy as discussed herein. In further embodiments the ceramide may be pegylated, conjugated with polyethylene glycol The amount of ceramide encapsulated in the liposome compared to the total lipids can vary, and a person of skill in the art would appreciate the amount in any embodiment will var with the particular application. For example, as disclosed in patent '891, can range from about 1:1 to 1:100.

A person skilled in the art will appreciate that additional ceramides or molecules may be encapsulated in the liposome or may be provided with the liposome in a pharmaceutical composition. The method of preparing the nanoliposome may vary and the methods here are not limited by any specific method of nanoliposome production.

The term "liposome" refers to a bilayer particle of amphipathic lipid molecules enclosing an aqueous interior space. Liposomes are typically produced as small unilamellar vesicles (SUVs), large unilammellar vesicles (LUVs) or multilammellar vesicles (MLVs). The lipid bilayer forms a hydrophobic membrane around an aqueous solution. The size of liposomes can be controlled, in one example, using well known techniques, including but not limited to, filtration through a filter having a defined pore size, extrusion and combinations thereof. Here a nanoliposome is prepared.

In one embodiment the nanoliposome has a diameter of 1 nm to 350 nm. In another embodiment the nanoliposome has a diameter of 20-200 nm, in a further embodiment between 70-90 nm and in a still further embodiment about 90 nm. When referring to "about" 90 nm is included in one embodiment a range of plus or minus 20 nm, in another embodiment plus or minus 15 nm, in a further embodiment plus or minus 10 nm and still further embodiments plus or minus 5 nm.

Any convenient means of preparing the nanoliposome may be utilized and the methods here are not limited by the method of making the nanoliposome. The following examples are for exemplification only and not intended to limit the scope of the invention.

By way of example without limitation, methods for preparation of nanoliposomes is described at Kester et al. (2015) 'preclinical development of a C6-ceramid nanoliposome, a novel sphigolipid therapeutic" Biol. Chem 396(6-7): 737-747 and in the '891 patent supra as well as Kester et al., U.S. Pat. No. 9,326,953, the contents of which are incorporated herein by reference in their entirety.

In one example as provided in the '891 patent, a method includes producing a composition comprising ceramide anionic liposomes which include providing a lipid mixture comprising at least one pegylated neutral lipid. One skilled in the art appreciates this is but one example of the composition comprising the nanoliposome and may vary depending upon the specific application. The example provided by the '891 patent provides the total amount of pegylated neutral lipid is an amount in the range of 5-20 Molar percent, inclusive, and wherein at least half of the amount of included pegylated neutral lipid is N-Octanoyl-Sphingosine-1-succinyl(methoxy(polyethylene)glycol)750; at least one anionic lipid, wherein the total amount of anionic lipid is an amount in the range of 5-15 Molar percent, inclusive; a ceramide which comprises one or more of a C2 to C26 ceramide where the ceramide is provided in an amount in the range of 1-40 Molar percent, inclusive; and cationic or neutral lipids, with the proviso that preferably the resulting lipid mixture has a net negative charge at physiological pH; sonicating the lipid mixture in the presence of an amount of a antineoplastic chemotherapeutic at a temperature in the range of 55-75° Celsius, inclusive, to produce a sonicated mixture; and passing the sonicated mixture through a filter having pores of a desired size to produce liposomes having the desired size, at a temperature in the range of 67-75° Celsius, producing a population of ceramide anionic liposomes, wherein the amount of the ceramide compared to the amount of total lipids in the liposomes is in the range of about 1:1-1:100. The '891 patent further provides in one example that ceramide is included in ceramide anionic liposome compositions in an amount convenient for delivery, and in an example, provided in an amount in the range of about 1-40 Molar percent, inclusive, or any amount in-between, and in further examples in the range of about 5-38 Molar percent, inclusive, or in the range of about 10-35 Molar percent, inclusive.

By way of further example, in the '953 patent is described a method of synthesis for the resorbable nanoparticles and includes a nonionic surfactant, such as poly(oxyethylene) nonylphenyl ether (IGEPAL™ 520 CO), or any other amphiphilic compound containing a polar head group and a non-polar tail, which is combined with water and a hydrophobic nonaqueous solvent, such as cyclohexane or isooctanol in order to form a reverse micelle structure. Growth-arresting, pro-apoptotic, lipid-derived compounds or other gene therapy agents can also be suspended in the aqueous phase as a solution, suspension or micellular mixture of water and drug or water and gene therapeutic agent. The resulting reverse micelle containing the active agent within its core is coated with an inorganic resorbable coating which biodegrades in a physiological, i.e., isotonic, environment. Kester et al. describes a ceramide nanoliposome that comprises multiple lipid components include, in addition to C6-ceramide, 1,2-distaearoyl-sn-glycero-3-phosphocholine; 1,2-dioleoyl-sn-glycero-3-phosphoethanolamine; 1,2-distearoyl-xn-glycerol-3-phosphoethanolaminde-polyethylene glycol. (Kester et al. supra p.740). In the example provided at Kester et al., the pegylated liposomes had a mean hydrodynamic diameter of 85 nm and 30 mol % C6-ceramide within the lipid bilayer. That particular example included C6 and C8-ceramide though the C6-ceramide was the only pharmacologically active ceramide. A skilled person can produce a stable nanoliposome that has a size for optimum efficacy and meets appropriate safety standards. Id.

Methods and compositions are provided according to the present invention for treating cancer. Methods of treatment of a subject having, or at risk of having cancer, and in an embodiment, treatment of a subject having liver (hepatocellular) cancer, are provided according to aspects of the present invention including administration of a pharmaceutically effective amount of a ceramide nanoliposome composition. Methods of treatment of a subject having, or at risk of having, cancer, are provided according to aspects of the present invention including administration of a pharmaceutically effective amount of a ceramide anionic nanoliposome composition. Methods of treatment of a subject having, or at risk of having, cancer, are provided including administration of a pharmaceutically effective amount of ceramide nanoliposome composition.

Still further methods of treatment of a subject having or at risk of having cancer include administering to a subject in need thereof, an animal, such as a human, a ceramide nanoliposome composition in conjunction with immunotherapy. Immunotherapy utilizes the cellular immune response that can recognize and destroy tumor cells. The immune response can be stimulated in various ways, including by ex vivo expansion of antigen-specific effectors and utilization of adoptive transfer or vaccination of the subject and means to overcome immune tolerance using an antagonist of PD-1, to achieve an in vivo immune response.

In the present methods, the immune response elicited by the immunotherapy is increased compared to the immune response when the ceramide nanoliposome is not administered along with the immunotherapy. As described herein, the enhanced immune response can include increased number of T-cells, increased adverse impact on cancer cells by the T-cell or other immune cell, decreased immunotolerance of the T-cell or other immune cell or the like. As discussed more fully below, the methods provide an immune response where tumor associated macrophages (TAM) are converted from type M2 to type M1. As showed below, M1 cytokine production is increase and M2 cytokine production may also be decreased. There is decreased production of M2-like markers in TAMs. Immune response produced by the immunotherapy is increased with the methods described here.

Adoptive Cell Transfer (ACT) is one such immunotherapy. T-cells may be utilized in such therapies. A tumor antigen specific T-cell population is administered to the subject in an embodiment. In one example, adoptive cell transfer uses activated and expanded autologous tumor reactive T-cells, effector cells, which are administered to the subject. Such a T-cell population in an embodiment expresses a T-cell receptor (TCR) having antigenic specificity for a cancer antigen, being able to specifically bind to and recognize the cancer antigen and elicit an immune response. See, e.g. Robbins et al. (2015) "A pilot trial using lymphocytes genetically engineered with an NY-ESO-1-reactive T cell receptor: long term follow up and correlates with response" *Clin. Cancer Res.* 21(5):1019-1027. By way of example, the process can involve obtaining a population comprising T-cells such as cytotoxic CD8+T-cells, from a subject, enriching and then expanding the population for T-cells and administering the cells. ACT can also use TILs, tumor infiltrating lymphocytes, that contain T-cells targeted for a subject cancer neoepitope. (See, e.g., Tran et al. (2016) "T-cell transfer therapy targeting mutant KRAS in cancer" *N. Engl. J. Med.* 375:2255-2262.

Another example of ACT uses Chimeric Antigen Receptors (CAR), in which the T-cells are genetically engineered to produce chimeric antigen receptors. These receptors are fragments or domains of usually synthetic antibodies that recognize or bind the tumor cell antigen. See, e.g., Kochenderfer et al. (2010) "Eradication of B-lineage cells and regression of lymphoma in a patient treated with autologous T cells genetically engineered to recognize CD19" *Blood* 116(2):4099-102; Kochenderfer et al. (2015) "Chemotherapy-refractory diffuse large B-cell lymphoma and indolent B-cell malignancies can be effectively treated with autologous T cells expressing an anti-CD19 chimeric antigen receptor" *J. Clin. Oncol.* 33(6):540-549.

Another approach to cancer immunotherapy utilizes vaccination and provides administration of tumor antigen-expressing cells, a process also referred to herein as immunization. These cells comprise an antigen that is capable of eliciting an enhanced immune response. A cell expressing a tumor specific antigen expresses a protein or other molecule specific to the cancer cell. In one embodiment the protein or other molecule is found only on cancer cells. In another embodiment the cancer cell has more of the protein or other molecule compared to non-cancer cells. Such molecules may be found outside or inside the cancer cell. In an embodiment the tumor specific antigen is one recognizing a carcinoma cell.

Many such antigens and cells expressing the same are known and will become available to one skilled in the art. See, e.g., Vigneron "Human tumor antigens and cancer immunotherapy" BioMed Research Int'l. Vol. 2015, Article ID 948501, 17 pages http://dx.doi.org/10.1155/2015/948501. By way of example, without limitations, HCC antigens include cyclophilin B, squamous cell carcinoma antigen SART2 and SART3, p53, multidrug resistance-associated protein, alpha-fetoprotein and human telomerase reverse transcriptase. (See Mizukoshi et al. (2011) "Comparative analysis of various tumor-associated antigen-specific T-cell responses in patients with hepatocellular carcinoma" *Hepatology* Vol. 53, No. 4, pp. 1206-1216. Still further examples include euykaryotic translation initiation factor 3, subunit I (GenBank No. BC003140), lactate dehydrogenase 1, A chain, (GenBank No. X02152), replication factor C2, 40 kDa (GenBank No. AL560344), and mitrochondrial carrier triple repeat 1 (GenBank No. BP363489). See Chen et al (2008) "Identification of tumor-associated antigens in human hepatocellular carcinoma by autoantibodies" *Oncol. Rep.* 20(4): 979-85. Such antigens may be expressed in any convenient cell that can express the antigen. An embodiment provides the cell may be an animal cells such as a mouse, rat, rabbit, monkey, human or other animal.

Additional cancer therapies provide for administration of an antagonist of a Programmed Death 1 protein (PD-1). For example, see the human PD-1 protein at NCBI No. NP_005009. PD-1, also referred to as a checkpoint protein. It attaches to PD-L1 or PD-L2, ligands expressed in human cancers. It acts to check the action of immune cells such as a T-cell, B-cell or an NKT cell, so that it will not attack non-cancer cells. Cancer cells, however, can have PD-L1 or PD-L2 present, which allows cancer cells to avoid attack from the immune system. By administering PD-1 inhibitors or PD-L1 or PD-L2 inhibitors to a subject, an immunotherapy for cancer is provided. A PD-1 antagonist is a composition that blocks such binding of PD-L1 or PD-L2 to PD-1 in an immune cell. A monoclonal antibody or fragment that binds to PD-1 or the ligand can be used as an antagonist.

Examples of mAbs that bind to human PD-1, and are useful in the treatment methods, medicaments and disclosed uses, are described in U.S. Pat. Nos. 7,488,802, 7,521,051, 8,008,449, 8,354,509, 8,168,757, WO2004/004771, WO2004/072286, WO2004/056875, US 20180092901 and US20110271358. Specific anti-human PD-1 mAbs useful as the PD-1 antagonist include: pembrolizumab (also known as MK-3475), a humanized IgG4 mAb with the structure described in WHO Drug Information, Vol. 27, No. 2, pages 161-162 (2013) and which comprises the heavy and light chain amino acid sequences, nivolumab (BMS-936558), a human IgG4 mAb with the structure described in WHO Drug Information, Vol. 27, No. 1, pages 68-69 (2013) and which comprises the heavy and light chain amino acid sequences, pidilizumab, a humanized monoclonal antibody, AMP-224, and AMP-514; the humanized antibodies h409A11, h409A16 and h409A17, which are described in WO2008/156712, and AMP-514. Examples of mAbs that bind to human PD-L1, and useful in the treatment methods, medicaments and disclosed uses, are described in WO2013/019906, WO2010/077634 A1 and U.S. Pat. No. 8,383,796. Examples of pecific anti-human PD-L1 mAbs useful as the PD-1 antagonist include MPDL3280A, BMS-936559, MEDI4736, MSB0010718C and an antibody which comprises the heavy chain and light chain variable regions of SEQ ID NO:24 and SEQ ID NO:21, respectively, of WO2013/019906. Other PD-1 antagonists include an immunoadhesin that specifically binds to PD-1 or PD-L1, and in a further example preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Examples of specific fusion proteins useful as a PD-1 antagonist include AMP-224 (also known as B7-DCIg), which is a PD-L2-FC fusion protein and binds to human PD-1.

Still further embodiments provide for administration of a composition comprising a ceramide nanoliposome, in an embodiment a C6, C8, C10 and/or C12 ceramide nanoliposome and in still another embodiment, a C6 ceramide nanoliposome (LipC6), and may further include administration of (i) tumor antigen-specific T-cells and/or (ii) administration of tumor antigen expressing cells and/or (iii) administration of a PD-1 antagonist, and any combination of (i)-(iii). The ceramide nanoliposome may be administered at the same time as any one of the therapies of (i)-(iii) or combination thereof, or administered before or after administration of any one of the therapies of (i)-(iii) or combination thereof, or before or after any one of combinations of therapies of (i)-(iii). Further embodiments provide for administration of a composition comprising ceramide nanoliposome as a primer before administration of any one of the therapies of (i)-(iii) or combination thereof. Still further embodiments provide for administration of the ceramide nanoliposome for two weeks every other day, followed by administration of any combination of (i)-(iii).

Cancers treated using methods and compositions described here are characterized by abnormal cell proliferation including, but not limited to, pre-neoplastic hyperproliferation, cancer in-situ, neoplasms and metastasis. Methods and compositions of the methods can be used for prophylaxis as well as amelioration of signs and/or symptoms of cancer. Cancers treated using methods and compositions of the present invention include solid tumors including, but not limited to, cancers of the head and neck, esophagus, rectum, anus, prostate, testicle, lung, pancreas, bladder, ovary, uterus, cervix, thyroid, breast, colon, kidney, liver, brain and skin, as well as non-solid tumors, including, but not limited to, hematological malignancies such as leukemia, lymphoma and multiple myeloma. Methods and compositions of the present invention can be used for prophylaxis as well as amelioration of signs and/or symptoms of cancer.

The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer. Such treatments may include slowing the growth of tumors, reversing the growth of existing tumors, and/or elimination of existing tumors. An embodiment provides that existing tumors after treatment can no longer be detected by MRI. Further embodiments provide for prevention of tumor formation.

A therapeutically effective amount of a composition is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to a composition, a therapeutically effective amount of a composition is effective to ameliorate or prevent one or more signs and/or symptoms of the condition. For example, a therapeutically effective amount of a composition is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to a composition of the present invention.

A pharmaceutical composition generally includes about 0.1-99% ceramide nanoliposomes. Combinations of one or more ceramide nanoliposomes may also be used.

As discussed supra, the ceramide nanoliposome may be administered in single and repeat doses. By way of example, Kester et al. supra, describes use of a single or repeat doses. In further embodiments, the ceramide nanoliposome may be administered in combination with an ACT therapy, immune therapy and/or administration of an antagonist of PD-1.

A therapeutically effective amount of a pharmaceutical composition of ceramide nanoliposomes will vary depending on the particular pharmaceutical composition used, the severity of the condition of the subject to be treated, the species of the subject, the age and sex of the subject and the general physical characteristics of the subject to be treated. One of skill in the art could determine a therapeutically effective amount in view of these and other considerations typical in medical practice. In one example, without intending to be limiting, a therapeutically effective amount would be in the range of about 0.001 mg/kg-100 mg/kg body weight, optionally in the range of about 0.01-10 mg/kg, and further optionally in the range of about 0.1-5 mg/kg. By way of yet further example, dosages in human applications can range from 20 mg/m2 to 400 mg/m2, with a preferred embodiment of 30 mg/m2 to 300 mg/m2. Further, dosage may be adjusted depending on whether treatment is to be acute or continuing.

A subject treated according to methods and using compositions of the present invention can be mammalian or non-mammalian. A mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. A non-mammalian subject can be any non-mammal including, but not limited to, a bird such as a duck, goose, chicken, or turkey. In aspects of methods including administration of a pharmaceutical composition to a subject, the subject is human.

Optionally, methods can additionally include administration of one or more adjunct pharmacologically active agents.

Non-limiting examples of adjunct pharmacologically active agents that can be administered include non-steroidal anti-inflammatory agents, antibiotics, antivirals, analgesics, antipyretics, antidepressants, antipsychotics, anticancer agents, antihistamines, anti-osteoporosis agents, anti-osteonecrosis agents, anti-inflammatory agents, anxiolytics, chemotherapeutic agents, diuretics, growth factors, hormones and vasoactive agents.

Compositions including ceramide anionic nanoliposomes according may be administered directly or may be formulated with one or more additional pharmaceutically acceptable carriers where desired. The term "pharmaceutically acceptable carrier" refers to a carrier which is substantially non-toxic to a subject to which the composition is administered and which is substantially chemically inert with respect to ceramide anionic liposomes and the encapsulated antineoplastic therapeutic of the present invention. Pharmaceutically acceptable carriers and formulation of pharmaceutical compositions are known in the art, illustratively including, but not limited to, as described in Remington: The Science and Practice of Pharmacy, 21st Ed., Lippincott, Williams & Wilkins, Philadelphia, Pa., 2006; and Allen, L. V. et al., Ansel's Pharmaceutical Dosage Forms and Drug Delivery Systems, 8th Ed., Lippincott, Williams & Wilkins, Philadelphia, Pa., 2005.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Such formulations are administered by a suitable route including parenteral and oral administration. Administration may include systemic or local injection, and particularly intravenous administration, such as infusion or injection.

The CNL can be co-administered with an immunotherapy agent, or immunotherapy agent included in the CNL. The composition comprising the CNL can be delivered intravenous administration, or in another example could be prepared and lyophilized/dried for IV use. The CNL can be combined with pharmaceutically acceptable vehicles such as saline, Ringer's solution, dextrose solution, and the like. Examples, without intending to be limiting, of liquid excipients and carriers include water and saline; solvents such as ethanol, glycerol, propylene glycols; stabilizers such as ethylene diamine tetraacetic acid, citric acid; antimicrobial preservatives such as benzyl alcohol, methyl paraben, propyl paraben; buffering agents such as citric acid, sodium citrate, potassium hydrogen tartrate, sodium hydrogen tartrate; tonicity modifiers such as sodium chloride, mannitol and dextrose. The particular dosage regimen, i.e., dose, timing and repetition, will depend on the particular individual and that individual's medical history.

Solid dosage forms for oral administration include capsules, tablets, pills, powders, and granules. In such solid dosage forms, at least one inert customary excipient (or carrier) can be included such as sodium citrate or dicalcium phosphate or (a) fillers or extenders, as for example, starches, lactose, sucrose, glucose, mannitol, and silicic acid, (b) binders, as for example, carboxymethylcellulose, aliginates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents and can also be of such composition that they release the active compound or compounds in a certain part of the intestinal tract in a delayed manner. Examples of embedding compositions which can be used are polymeric substances and waxes.

Suspensions, in addition to a hydrophilic antineoplastic chemotherapeutic encapsulated in ceramide anionic liposomes, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

A topical formulation can be an ointment, lotion, cream or gel in particular aspects. Topical dosage forms such as ointment, lotion, cream or gel bases are described in Remington: The Science and Practice of Pharmacy, 21st Ed., Lippincott Williams & Wilkins, 2006, p. 880-882 and p. 886-888; and in Allen, L. V. et al., Ansel's Pharmaceutical Dosage Forms and Drug Delivery Systems, 8th Ed., Lippincott Williams & Wilkins, 2005, p. 277-297.

A pharmaceutical composition generally includes about 0.1-99% ceramide nanoliposomes. Combinations of one or more of ceramide nanoliposomes may also be used.

Optionally, a method of treating a subject having cancer or at risk of having cancer further includes an adjunct anti-cancer treatment. An adjunct anti-cancer treatment can be administration of one or more additional antineoplastic chemotherapeutic agents, included or not included in liposomes, administered separately or together.

References cited here are incorporated herein by reference in their entirety. The following is provided by way of exemplification and is not intended to limit the scope of the invention.

EXAMPLES

Example 1

Immune competent C57BL/6 mice received intraperitoneal injections of carbon tetrachloride and intra-splenic injections of oncogenic hepatocytes. As a result, tumors, resembling human hepatocellular carcinomas, developed in a fibrotic liver setting. After tumors formed, mice were given injection of LipC6 or vehicle via tail vein every other day for 2 weeks. This was followed by administration, also via tail vein, of tumor antigen-specific (TAS) CD8+ T cells isolated from the spleens of line 416 mice, and subsequent immunization by intraperitoneal injection of tumor antigen-expressing B6/WT-19 cells. Tumor growth was monitored with magnetic resonance imaging. Tumor apoptosis, proliferation, and AKT expression were analyzed using immunohistochemistry and immunoblots. Cytokine production, phenotype, and function of TAS CD8+ T cells and tumor associated macrophages (TAMs) were studied with flow cytometry, real-time PCR, and ELISA. Reactive oxygen species (ROS) in TAMs and bone marrow-derived macrophages, induced by colony stimulating factor 2 (GMCSF or CSF2) or colony stimulating factor 1 (MCSF or CSF1), were detected using a luminescent assay.

Injection of LipC6 slowed tumor growth by reducing tumor cell proliferation and phosphorylation of AKT, and increasing tumor cell apoptosis, compared to vehicle. Tumors grew more slowly in mice given combination of LipC6 injection and TAS CD8+ T cells followed by immunization compared to mice given vehicle, LipC6, the T cells, or immunization alone. LipC6 injection also reduced numbers of TAMs and their production of ROS. LipC6 induced TAMs to differentiate into an M1 phenotype, which reduced immune suppression, and increased activity of CD8+ T cells. These results were validated by experiments with bone marrow-derived macrophages induced by GMCSF or MCSF.

In mice with liver tumors, injection of LipC6 reduces the number of TAMs and the ability of TAMs to suppress the anti-tumor immune response. LipC6 also increases the anti-tumor effects of TAS CD8+ T cells.

Materials and Methods

Mice. Male C57BL/6 mice were purchased from the Jackson Laboratory (Bar Harbor, Me.). Line MTD2 transgenic mice that express full-length SV40 T antigen (TAg) driven by the major urinary protein (MUP) promoter have been previously described[23]. Line 416 mice served as the source of TAg-specific CD8+ T cells (TCR-I T cells) were described previously[24]. All experiments with mice were performed under a protocol approved by the Institutional Animal Care and Use Committee (IACUC). All mice received humane care according to the criteria outlined in the "Guide for the Care and Use of Laboratory Animals".

Peptides, reagent and antibodies. Peptides were synthesized in Penn State Hershey Macromolecular Core Facility and solubilized in DMSO. LipC6 (30 mol % ceramide) and vehicle (no C6-ceramide) were prepared by Dr. Mark Kester as described previously[18]. Unlabeled and fluorochrome-conjugated antibodies against CD16/CD32, CD3, CD8a, CD4, CD25, FoxP3, CD11b, F4/80, CD11c, PDL1, CD80, CD86 and IFN-γ were purchased from eBioscience (San Diego, Calif.).

Cell line and medium. TAg-transformed B6/WT-19 cells have been described previously[24]. The cell line was maintained in DMEM (Cellgro, Manassas, Va.) supplemented with 100 U/mL penicillin, 100 μg/mL streptomycin, 100 μg/mL kanamycin, 2 mM L-glutamine, 10 mM HEPES, 0.075% (w/v) NaHCO$_3$, and 10% FBS at 37° C. in a 5% CO$_2$ humidified atmosphere.

Preparation of clinically relevant murine model of HCC[17]. To model tumor growth in a fibrotic liver, 10% CC14 (v/v) solution in corn oil was IP injected into 6-week-old C57BL/6 mice twice a week at a dose of 8 mL/kg of body weight (BW) for six weeks. Two weeks after the last injection, the mice received intrasplenic innoculation of histologically normal hepatocytes isolated from TAg-transformed young male MTD2 mice at a dose of 5×10$^5$ cells/mouse. At the onset of puberty, the generation of androgens in the recipient mice initiated oncogenic TAg expression under control of a liver-specific promoter. As a result, the transferred hepatocytes become cancer cells and formed tumors in the setting of liver fibrosis/cirrhosis. Small tumors can be detected by MRI two months after hepatocyte inoculation.

LipC6 injection, adoptive cell transfer (ACT), and immunization. LipC6 or vehicle were injected via tail vein every other day for two weeks at dose of 35 mg/kg BW in 200 µl volume. For ACT, TCR-I cells were isolated from the spleens of line 416 mice and enriched by $CD8^+$ magnetic microbeads (Miltenyi Biotech, Auburn, Calif.) according to the manufacturer's instructions. $1 \times 10^6$ TCR-$I^+$ T cells were suspended in 0.2 mL of HBSS and injected into the mice via tail vein. For immunization, $3 \times 10^7$ B6/WT-19 cells suspended in 0.2 mL of PBS were IP injected to mice.

Isolation of leukocytes from liver or tumors. To isolate liver- or tumor-infiltrating leukocytes (TIL), a liver perfusion was first performed via the portal vein with 15 mL collagenase IV (Sigma, Saint Louis, Mo.) solution. The harvested tumor or live tissues were cut to small pieces and incubated in mixed enzymes including collagenase IV, hyaluronidase, and DNase IV (Sigma, Saint Louis, Mo.) at room temperature (RT). 1.5 hours later, lower speed centrifugation, RBC lysis, and the gradient centrifugation were used to isolate leukocytes. These cells were maintained in RPMI 1640 medium (Cellgro, Manassas, Va.) supplemented with 100 U/mL penicillin, 2 mM L-glutamine, 10 mM HEPES, 50 µM 2-mercaptoethanol, and 10% FBS.

Flow cytometry. Ex vivo staining of leucocytes with fluorochrome-labeled antibodies was performed on single-cell suspensions[25]. Stained cells were analyzed using Accuri C6 flow cytometer (BD Biosciences). Data were analyzed using FlowJo software (Tree Star). Staining of intracellular IFN-γ and TNF-α was performed as described previously[25]. Staining of FoxP3 was performed with a buffer set from eBioscience.

Preparation of bone marrow-derived macrophages (BMMs). Bone marrow was harvested from the femurs and tibias of C57BL/6 mice. RBCs were lysed with lyse buffer (eBioscience, San Diego, Calif.). $3 \times 10^6$ single cells were then plated in a 100 mm petri dish and cultured in 10 mL DMEM medium (cellgro, Manassas, Va.) supplemented with 10% FBS, 10 mM HEPES, 1:100 (v/v) non-essential amino acids, 1 mM sodium pyruvate (Sigma, St Louis, Mo.), and 20 ng/mL mouse macrophage colony-stimulating factor (mMCSF) or granulocyte macrophage colony-stimulating factor (mGMCSF) (R&D system, Minneapolis Minn.). 5 mL fresh complete medium containing 20 ng/mL mMCSF or mGMCSF was added to the culture cells on day 4. Adherent cells were harvested on day 7 and used as BMMs. ELISA. The level of IFN-γ in cell culture supernatant was measured with mouse Quantikine ELISA Kits (Cat #DY485, R&D system, Minneapolis Minn.) according to the manufacturer's instructions.

ROS Detection Assay. ROS level was detected and quantified using the ROS-Glo™ $H_2O_2$ Assay (Promega, Madison, Wisc.) according to the manufacturer's protocol. Briefly, cells were grown in 96-well plate until 80% confluence followed by the incubation with LipC6 or vehicle for 6 hours, the $H_2O_2$ substrate was added to each well and incubated in 37° C., 5% $CO_2$ incubator for desired time, then ROS-Glo™ detection solution was added and incubated for 20 minutes at RT. Luminescence intensity w quantified using a microplate reader and normalized to control cells.

Total RNA extraction and real-time PCR. Total RNAs were extracted using Trizol reagent (Invitrogen, Carlsbad, Calif.) according to the manufacturer's instructions. 2 µg of total RNAs were used for cDNA synthesis with High Capacity cDNA Reverse Transcription Kits (Applied Biosystems, CA). Each PCR was performed in a 20 µl reaction mixture containing SYBR Green I (Roche, Basel, Switzerland). Real-time PCR was performed with CFX96 Real-Time PCR Detection System (Bio-Rad, CA). Reactions were run in triplicate in three independent experiments. Expression data were normalized to the geometric mean of housekeeping gene 18S rRNA to control the variability in expression levels and were analyzed using the $2^{\Delta\Delta CT}$ method.

Primers for real-time PCR. Primers were synthesized by Fisher Scientific (Waltham, Mass.). The sequences are shown in Table 1.

TABLE 1

Primers for real time PCR

| Target | Forward primer (5'-3') | Reverse primer (5'-3') |
|---|---|---|
| 18S | AAGTCCCTGCCCTT TGTACACA (SEQ ID NO: 1) | GCCTCACTAAACCAT CCAATCG (SEQ ID NO: 2) |
| iNOS | GACGAGACGGATAG GCAGAG (SEQ ID NO: 3) | GTGGGGTTGTTGCTG AACTT (SEQ ID NO: 4) |
| IFN-γ | GAAAGCCTAGAAAG TCTGAATAACT (SEQ ID NO: 5) | ATCAGCAGCGACTCC TTTTCCGCTT (SEQ ID NO: 6) |
| IL-12 | GAGGACTTGAAGAT GTACCAG (SEQ ID NO: 7) | TTCTATCTGTGTGAG GAGGGC (SEQ ID NO: 8) |
| TNF-α | ACGGCATGGATCTC AAAGAC (SEQ ID NO: 9) | GTGGGTGAGGAGCAC GTAGT (SEQ ID NO: 10) |
| ARG1 | ATGGAAGAGACCTT CAGCTAC (SEQ ID NO: 11) | GCTGTCTTCCCAAGA GTTGGG (SEQ ID NO: 12) |
| IL-4 | ACAGGAGAAGGGAC GCCAT (SEQ ID NO: 13) | GAAGCCCTACAGACG AGCTCA (SEQ ID NO: 14) |
| Fizz1 | TTGCAACTGCCTGT GCTTAC (SEQ ID NO: 15) | CAAGAAGCAGGGTAA ATGGG (SEQ ID NO: 16) |
| YM1 | AGAAGGGAGTTTCA AACCTGT (SEQ ID NO: 17) | GTCTTGCTCATGTGT GTAAGTGA (SEQ ID NO: 18) |
| CD80 | CGACTCGCAACCAC ACCATTAAG (SEQ ID NO: 19) | TCCTGCCCCAAAGAG CACAAG (SEQ ID NO: 20) |
| CD86 | GCCCATTTACAAAG GCTCAA (SEQ ID NO: 21) | TGTTCCTGTCAAAGC TCGTG (SEQ ID NO: 221) |
| PD-L1 | CAGAAGCTGAGGTA ATCTGGA (SEQ ID NO: 23) | TGAGTCCTGTTCTGT GGAGG (SEQ ID NO: 24) |
| CD11c | CTGGATAGCCTTTC TTCTGCTG (SEQ ID NO: 25) | GCACACTGTGTCCGA ACTCA (SEQ ID NO: 26) |

Statistics Analysis. Paired data were analyzed using a 2-tailed paired Student's t test. A P value of less than 0.05 was considered significant.

Study approval. Animal experiments were approved by the IACUC of the Pennsylvania State University College of Medicine, the Medical University of South Carolina, and the University of Missouri.

RESULTS

Figure 1C:
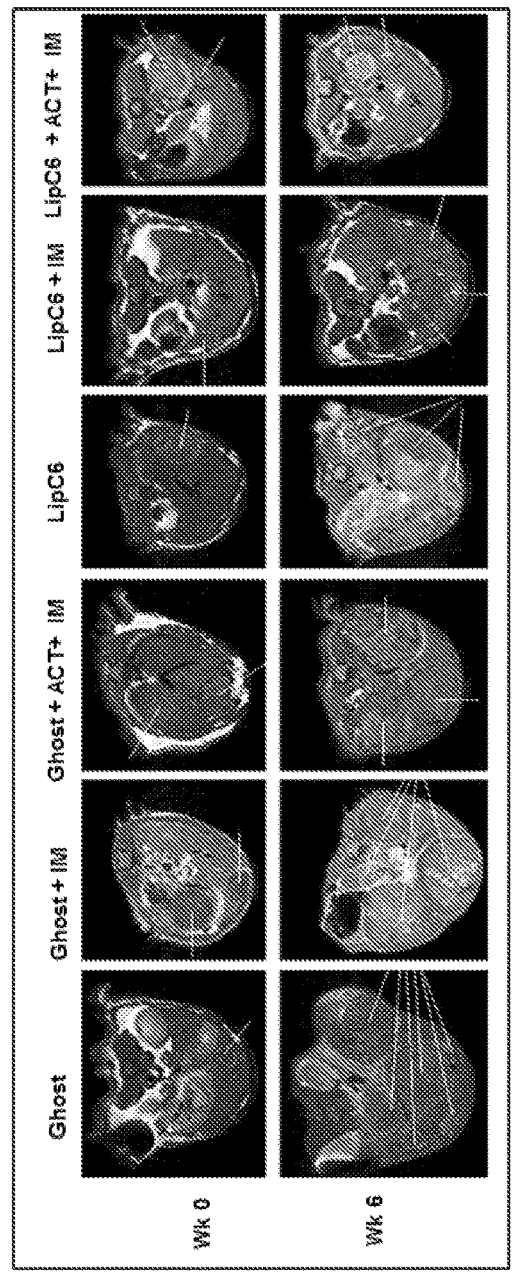
Figure 1B:
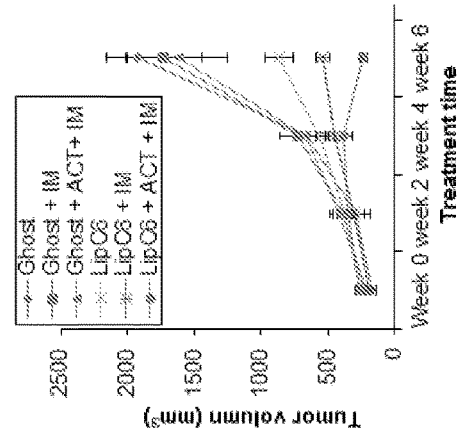
Figure 1D:
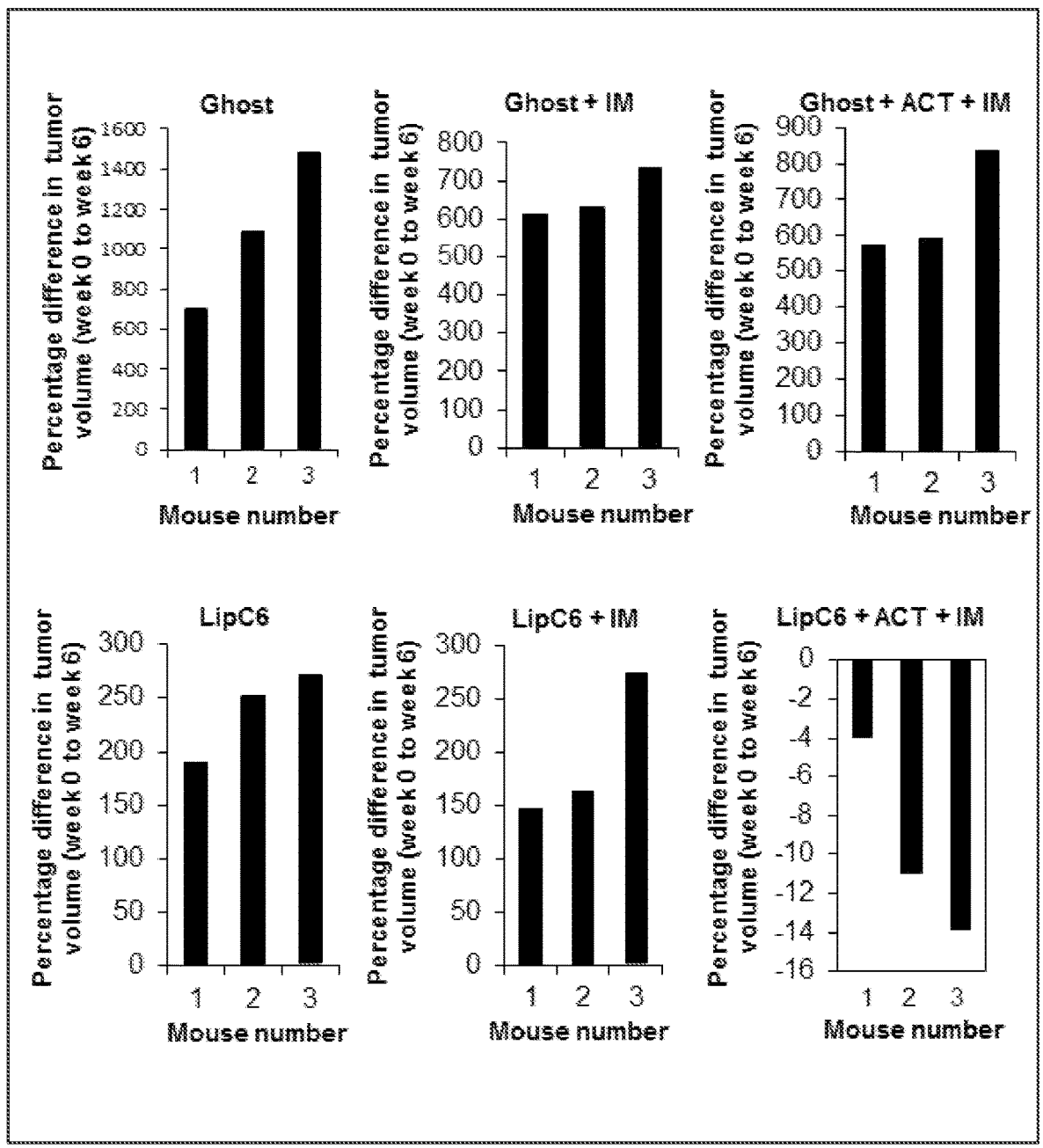
Figure 9A:
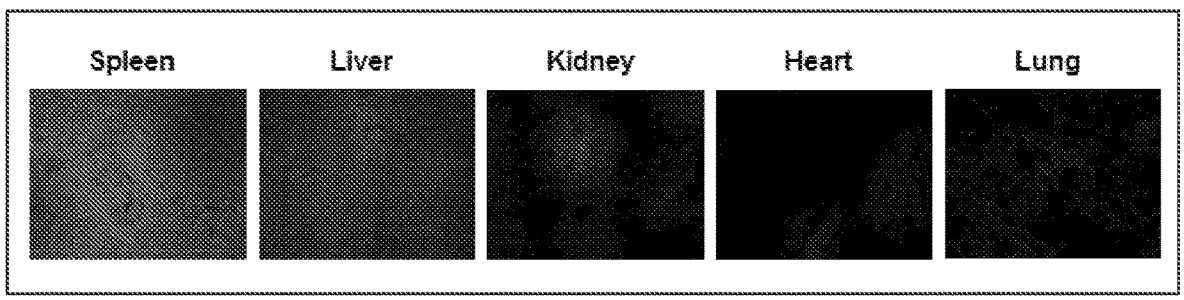
FIG. 9 shows images showing biodistribution of LipC6 in HCC-bearing mice. LipC6 was labeled with Rhodamine, then injected into the TBMs. About 16 hours later, the mice were euthanized, the different organs were harvested to prepare tissue sections. LipC6 biodistribution was monitored under fluorescence microscopy (A). To detect main cells taking up LipC6 particles, LipC6 was administrated into TBMs as the previous description. One day later, the tumors were harvested to make the section. This section was detected under electron microscopy. Arrows show the LipC6 particles in the tumors (B).
Figure 9B:
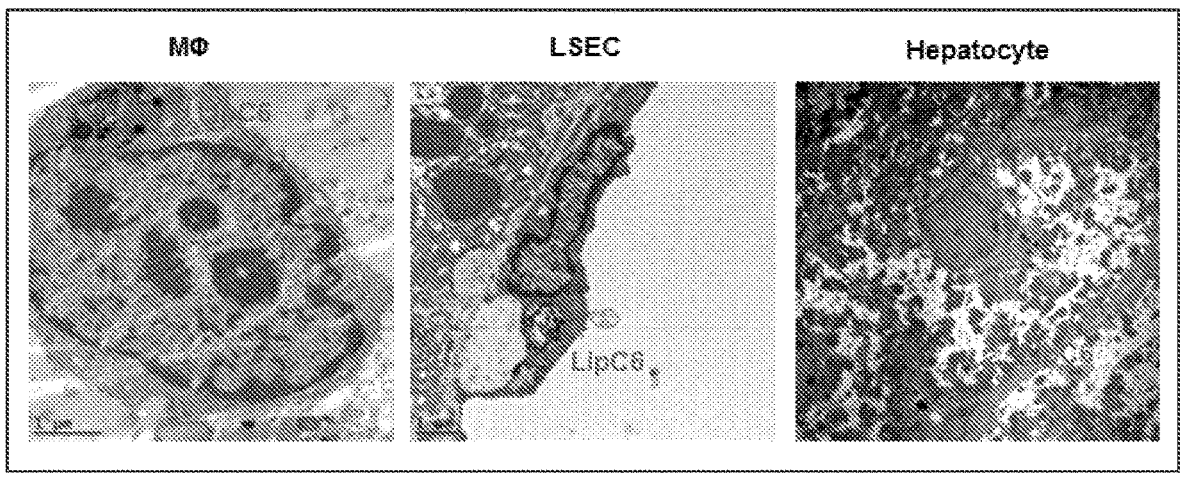
Figure 10A:
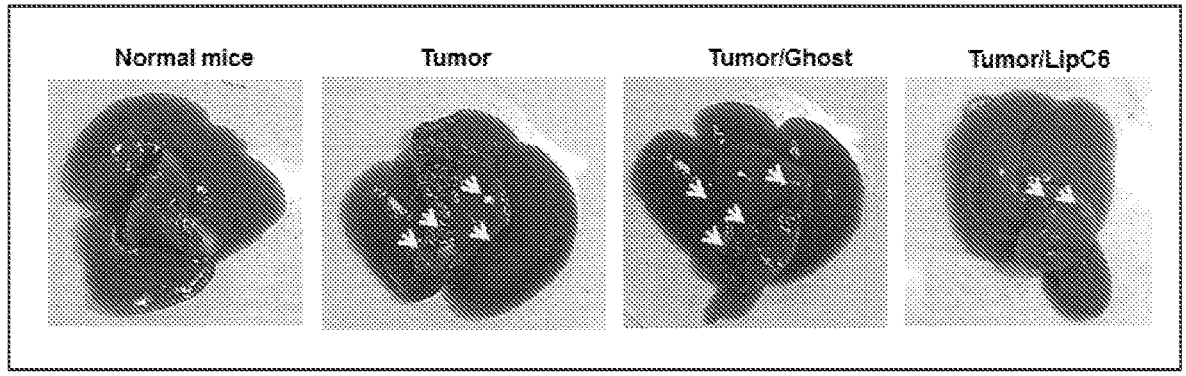
FIG. 10 shows photographs (A), graphs (B, D, F) and images of flow cytometry (C, E) of experimental results showing therapeutic and immunomodulatory effect of LipC6 in DEN-induced murine model of HCC. Two-week-old of C57BL/6 mice received a single IP injection of a mutagenic carcinogenic agent DEN. Six weeks later, the mice were given repeat IP dosing with $CCl_4$ for up to 14 consecutive weeks. Ten weeks after DEN injection, the mice were assigned into three groups and received vehicle, LipC6, or no injection as described in the methods. 24 weeks after DEN injection, all mice were euthanized to evaluate the tumors (A) and measure the tumor volume (B). Liver/tumor-infiltrating leukocytes were isolated and stained with the fluorchrome-conjugated antibodies for different markers. Flow cytometry was conducted to analyze the frequency of CD4⁺ T cells and CD8⁺ T cells in gated CD3⁺lymphocytes (C and D) and F4/80⁺CD11b⁺MΦ in liver/tumor-infiltrating leukocytes (E and F).
Figure 10B:
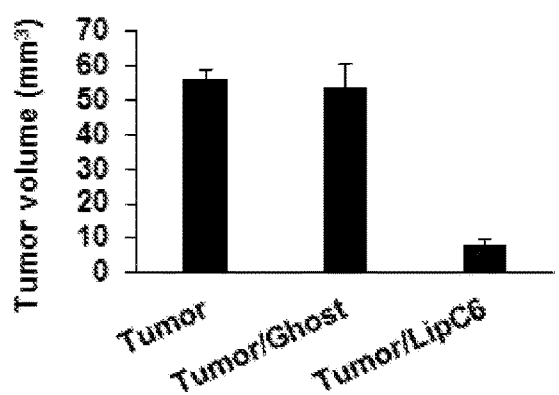
Figure 10C:
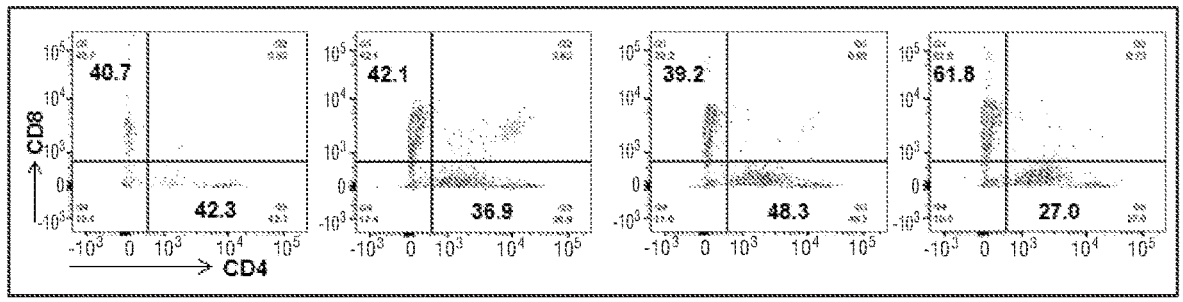
Figure 10D:
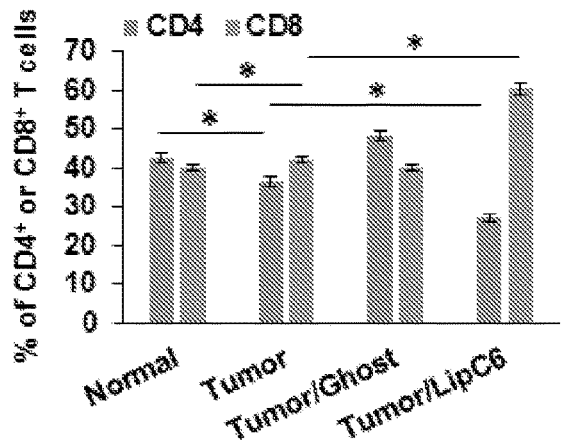
Figure 10E:
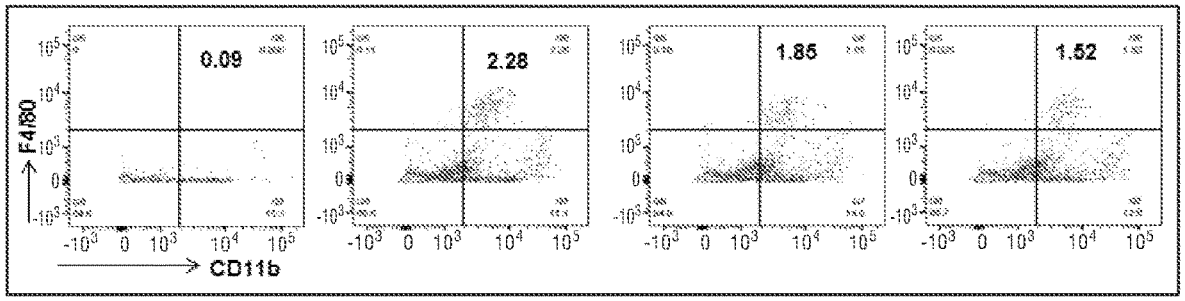
Figure 10F:
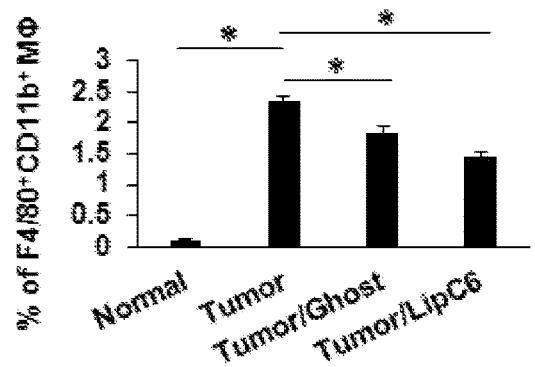

LipC6 Promotes Elimination of Established Tumors in Combination with Tumor Antigen-Specific (TAS) CD8+ T Cells and Immunization We evaluated the therapeutic efficacy of LipC6 monotherapy and its combination with immunotherapy in our clinically relevant HCC model. Naïve TCR-I T-cells isolated from line 416 mice served as TAS CD8+ T cells which specifically recognize TAg-epitope-I. B6/WT-19 cells served as tumor specific antigens that express full-length wild type TAg. Size-matched tumor-bearing mice (TBMs) were randomly assigned to six groups and received the following administrations: LipC6 injection; LipC6 injection followed by immunization; LipC6 followed by ACT and immunization (FIG. 1A). Parallel three control groups of mice were injected with vehicle instead of LipC6. Fluorescence detection indicated that Rhodamine-labeled LipC6 mainly distributed in the spleen and liver (FIG. 9A). Electron micrographs of tumor sections confirmed that LipC6 particles mainly localize to tumor cells, macrophages, and liver sinusoidal endothelial cells (FIG. 9B). These suggest that LipC6 may be specifically appropriate for the therapy of HCC. MRI was used to monitor therapeutic efficacy by assessing initial tumor volume and subsequent tumor growth (FIG. 1B-1C). In three vehicle-related cohorts, tumors continued to progress after initial injection with >700% increase in tumor size by week 6 (FIGS. 1B-D). In contrast, LipC6 monotherapy slowed tumor growth, resulting in <300% increase in tumor size within the 6-week administration period. The combination of LipC6 and immunization was more effective with <180% increase in tumor size over 6 weeks of administration (FIGS. 1B-D). Importantly, LipC6-integrated triple combination therapy not only retarded tumor growth, but eventually led to regression of established tumors (FIGS. 1B-D). Collectively, these data demonstrate that LipC6 synergizes with immunotherapy to powerfully suppress tumor growth which is involved in LipC6's mediated immune activation. LipC6's therapeutic and immunomodulatory effect were also detected in an N-nitrosodiethylamine (DEN)-induced HCC model (FIG. 10).

LipC6 Injection Preserves the TAS Effector T Cell Response

Figure 2A:
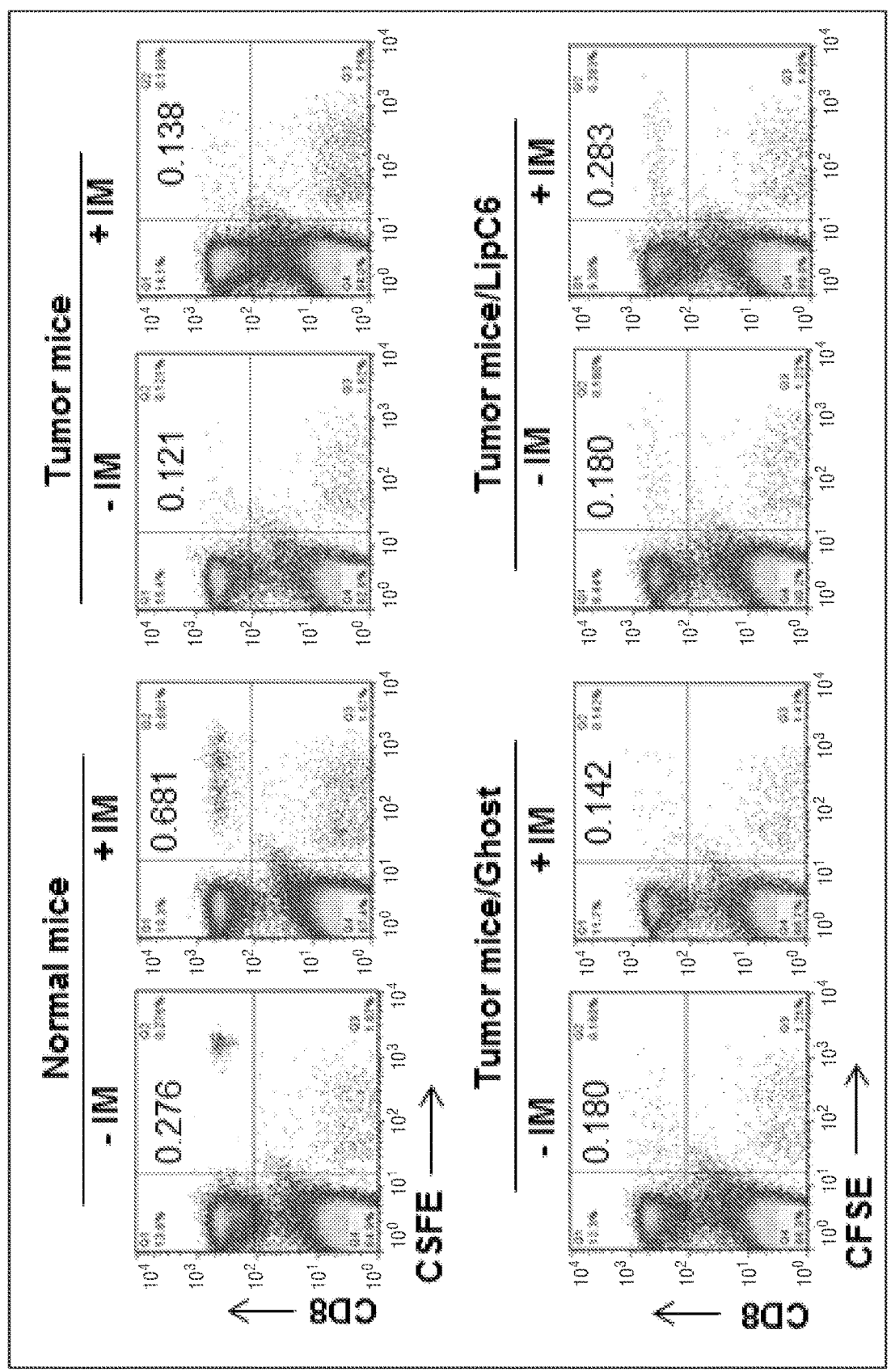
FIG. 2 shows images of flow cytometry (A-D), a graph (E) and cell staining (F) showing LipC6 injection restoring exhausted CD8$^+$ T-cell function in HCC and exerting tumoricidal effect. Size-matched TBMs were randomly assigned into one of three groups: vehicle, LipC6, or no injection. Two weeks after injection, mice received ACT of 1×10$^6$ naïve TAS TCR-I T cells which were labeled by CFSE. On the second day, half of the mice in each group were immunized as in Methods with TAg-transformed B6/WT-19 cells. Seven days after TAS immunization, spleens were harvested and splenic lymphocytes were isolated. Wild type C57BL/6 mice with or without immunization were used as controls. CFSE dilution in TCR-I T cells was detected by flow cytometry after labeling cells with anti-CD8 (A). IFN-γ production in effector CD8$^+$ T cells upon short-term exposure to peptide I was detected by flow cytometry after labeling with anti-CD8 and IFN-γ (B). Expression of PD-1 in CD8$^+$ TILs (C) and CD4$^+$ T TILs (D) was detected after labeling cells anti-CD4, CD8 and PD-1. In vitro incubation with anti-PD1 antibody increases the IFN-γ production in TILs (E). IHC and H&E staining were used to detect the level of Ki67, CD31, cleaved caspase-3 and necrosis in tumors from each mouse with the indicated monotherapies (F). The results implied that in vivo injection with LipC6 suppressed tumor cell proliferation and vascularization, with increased apoptosis and necrosis. Data are representative of three independent analyses.
Figure 2B:
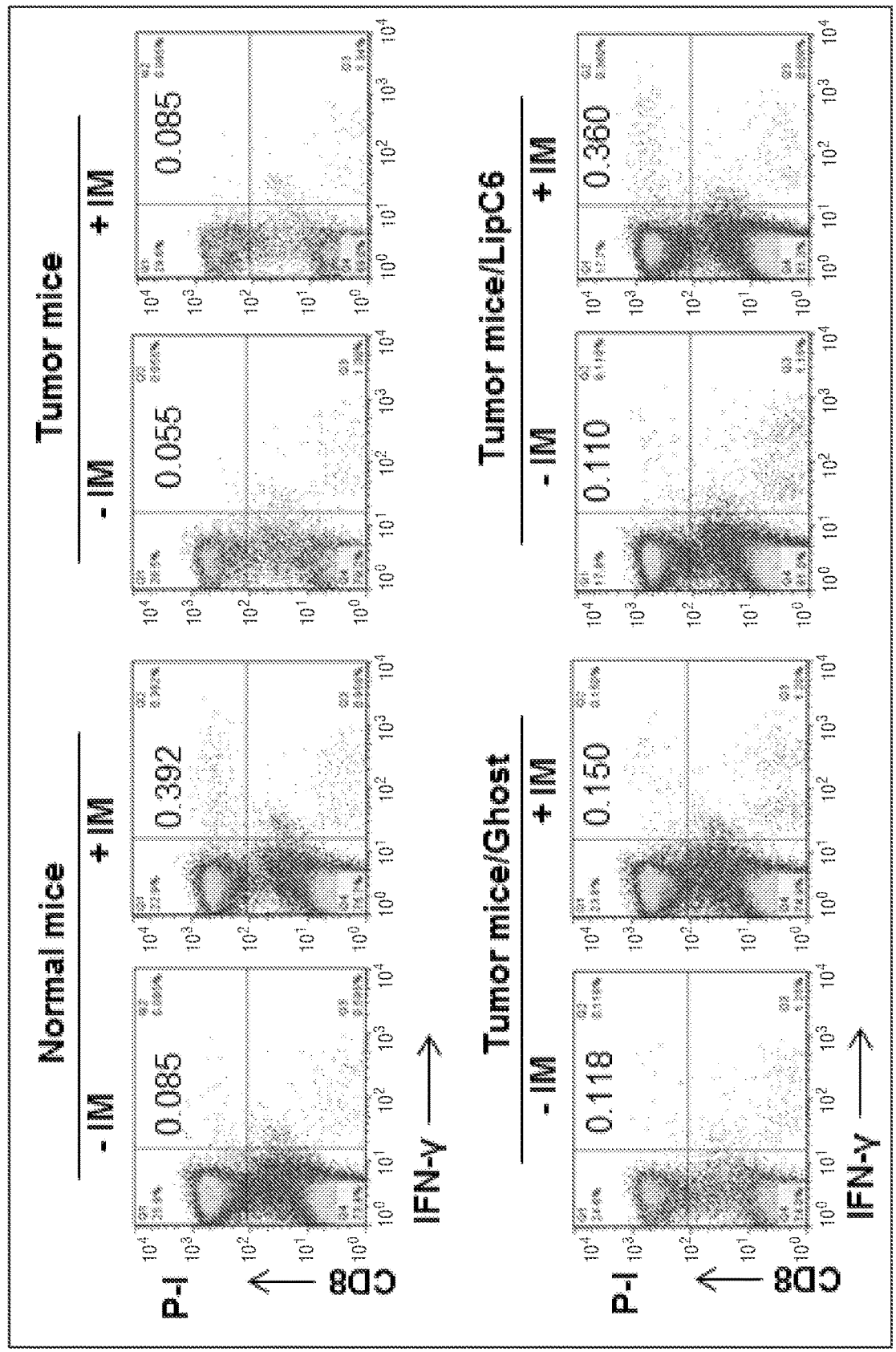
Figure 11A:
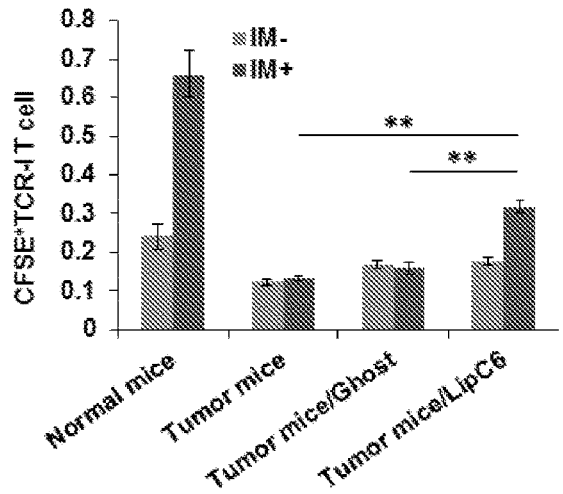
FIG. 11 shows graphs showing accumulated results for FIGS. 2A-2D.
Figure 11B:
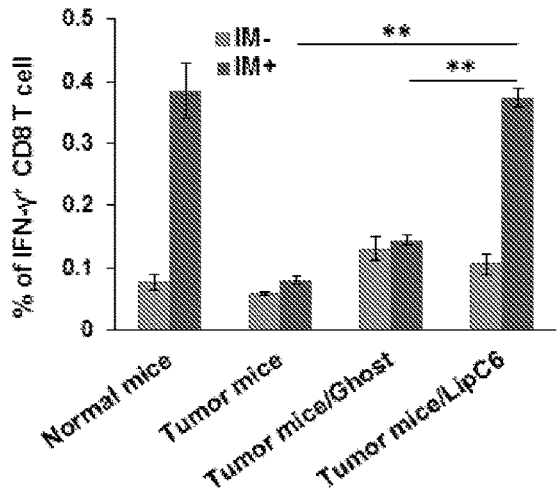

Considering the enhanced tumoricidal effect of LipC6-integrated immunotherapy relative to control monotherapies with LipC6 or immunotherapy alone, we hypothesized that LipC6 may be able to prime therapeutic antitumor immune response. To test this hypothesis, HCC-bearing mice were assigned into three groups: vehicle, LipC6, and no injection. Following the injection, each mouse in the three groups received ACT of naïve TAS TCR-I T cells labeled with CFSE. Half of the mice in each group received TAS immunization with B6/WT-19 cells. Seven days after immunization, CFSE dilution was observed in TCR-I T cells recovered from the spleens of all three groups of TBMs, suggesting that proliferation of naïve TCR-I T cells occurred after initial interaction with tumor antigens without the need for immunization. However, further expansion of TCR-I T cells in response to TAS immunization were only detected in the LipC6-injected TBMs, with 0.28% CSFE$^{+CD}$8+ T cells observed in immunized mice versus 0.18% in unimmunized mice (FIG. 2A and FIG. 11A). In addition, the expansion of TCR-I T cells was accompanied by their differentiation to effector cells. In vitro short term exposure to epitope-I peptide revealed an increase in the frequency of CD8+ T cells producing IFN-γ (0.36% IFN-γ+CD8+T cells) in LipC6-injected and immunized mice, which was equivalent to that observed in immunized normal mice and much higher than that in control HCC-bearing mice without injection (0.085% IFN-γ+CD8+T cells) or vehicle-injected mice (0.15% IFN-γ+CD8+T cells) (FIG. 2B and FIG. 11B). These results indicate that LipC6 injection protects TAS CD8+ T cells in TBMs, maintaining their potential for response to immunization.

Figure 2C:
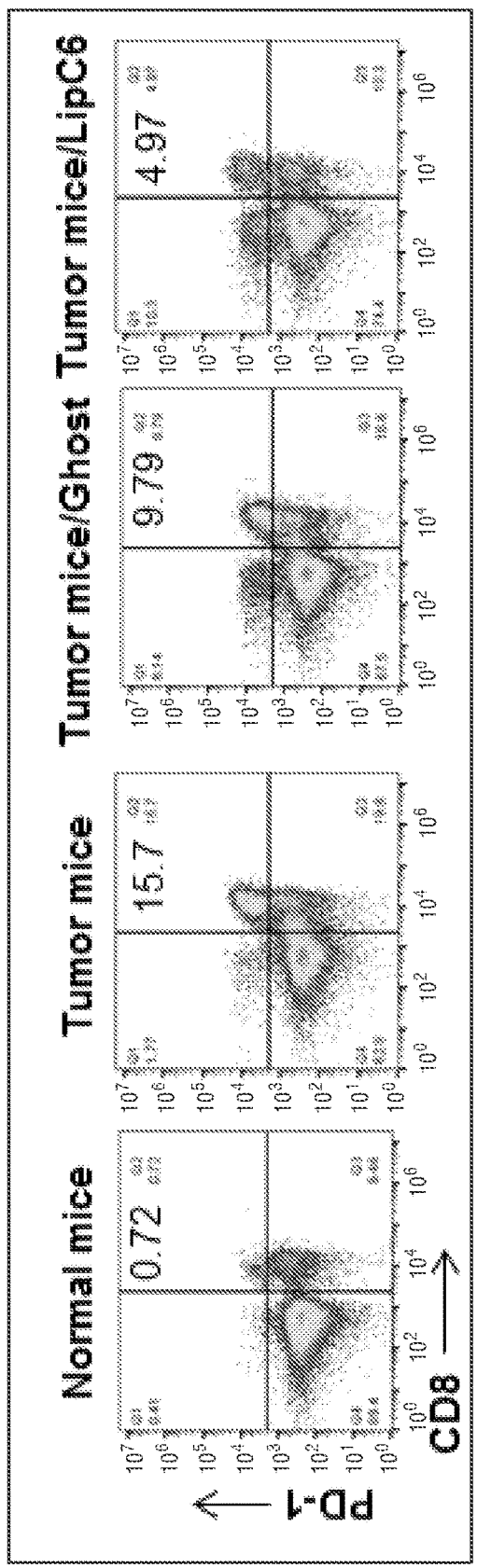
Figure 2D:
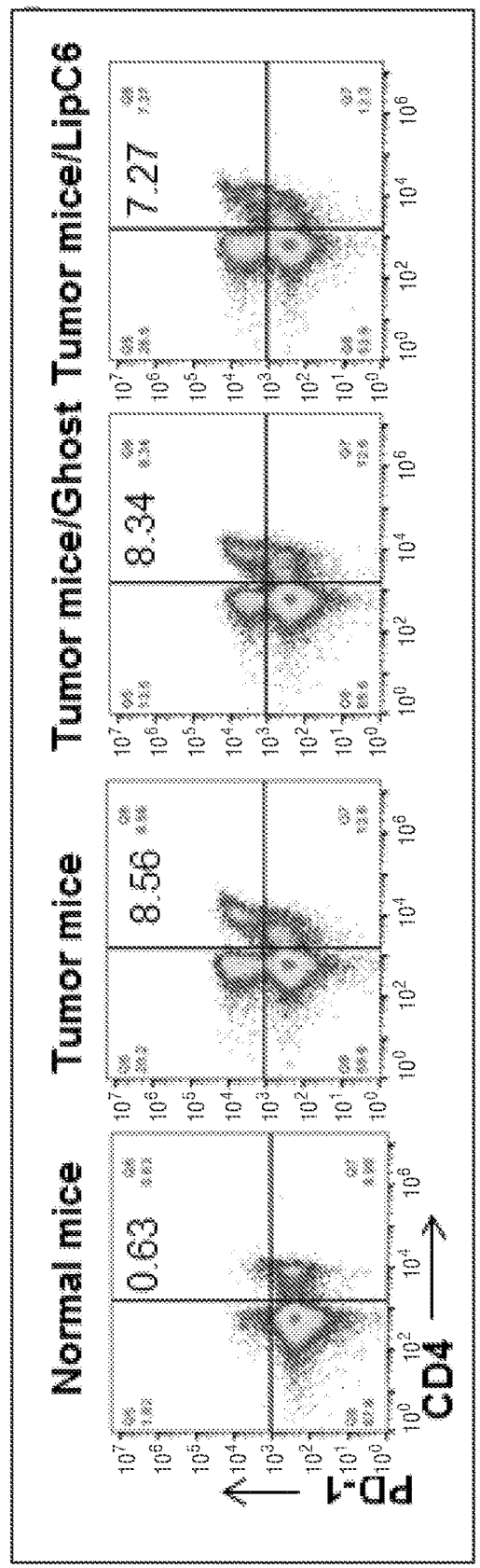
Figure 11C:
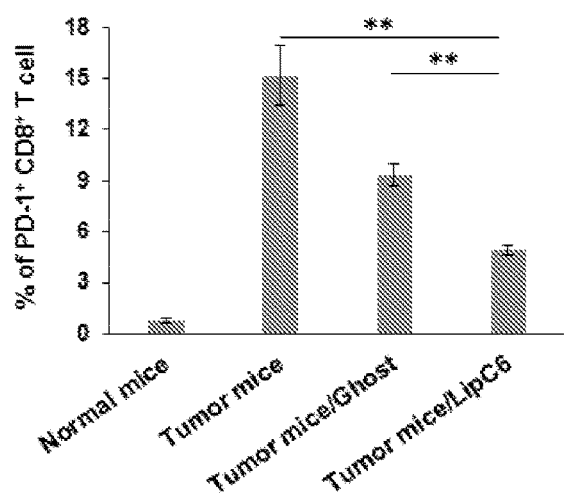
Figure 11D:
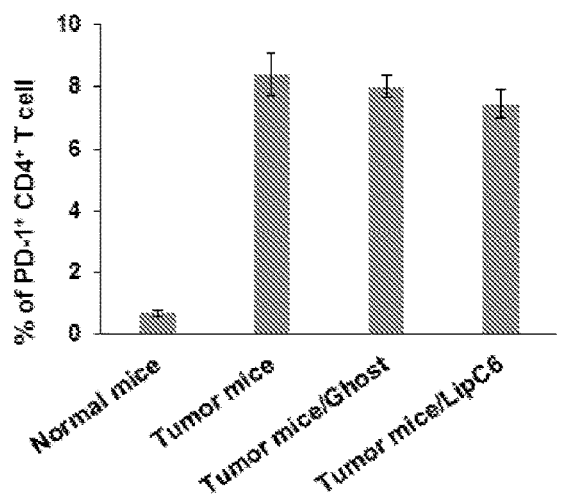

Next, we investigated whether LipC6 injection influences the phenotype of CD8+ TILs. Flow cytometry analysis showed that tumor growth induced noticeable increase in the frequency of CD8+TILs expressing PD-1 (15.7%) compared to that in tumor-free mice (0.72%). In vivo injection of TBMs with LipC6 resulted in remarkable reduction in the frequency of PD-1+CD8+TILs (4.97%) (FIG. 2C and FIG. 11C). However, LipC6 injection did not similarly reduce the frequency CD4+TILs expressing PD-1 (FIG. 2D and FIG. 12D). Collectively, these data suggest that LipC6 injection modulates effector CD8+ T cells phenotypically and functionally.

Figure 2E:
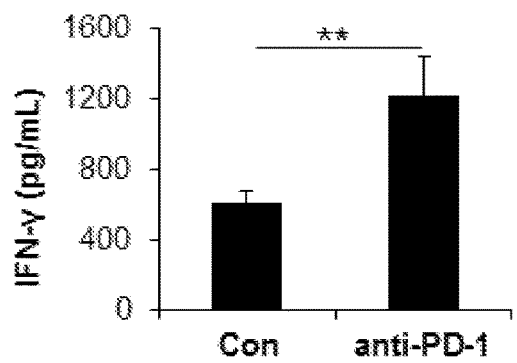

Since LipC6 injection increased the accumulation of functional TAS CD8+ T cells and also reduced the population of PD-1+TILs, we investigated if PD-1 blockade could improve TIL activity. TILs isolated from TBMs were stimulated with anti-CD3 and anti-CD28 for 48 hours in the presence or absence of anti-PD-1 Abs. The supernatant was harvested to measure IFN-γ production by ELISA. The results showed that anti-PD-1 significantly enhanced IFN-γ production in TILs from 500 pg/mL to 1200 pg/mL (FIG. 2E). These data suggest that LipC6 may improve the function of TILs through suppression of PD-1 expression.

LipC6's Inherent Tumoricidal Properties

Figure 2F:
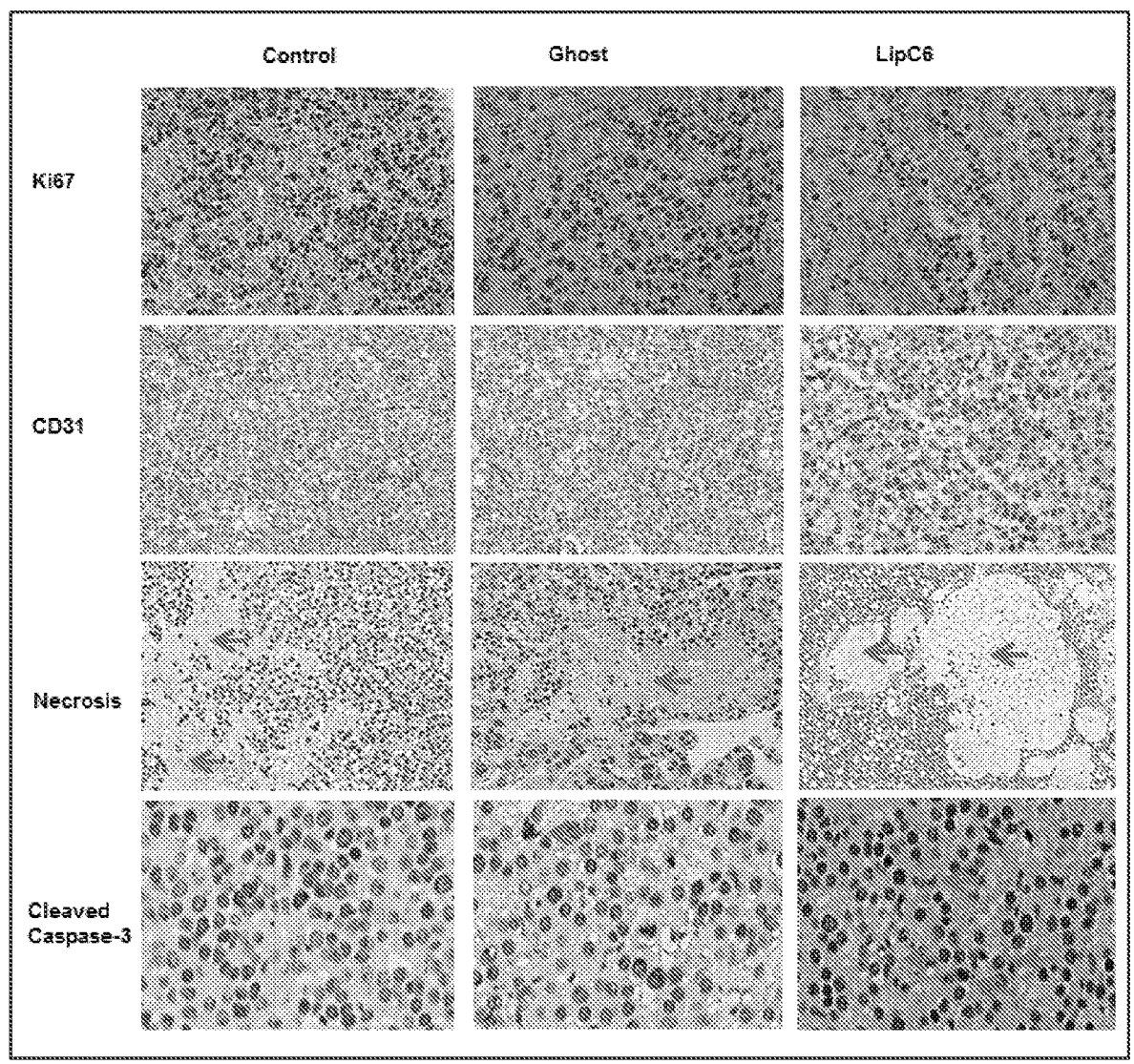
Figure 12:
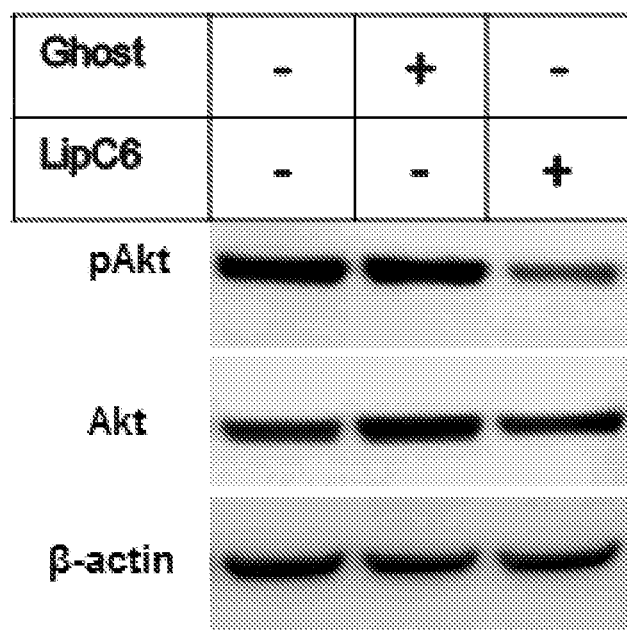
FIG. 12 shows a gel showing immunoblotting to detect pAKT and AKT in tumors. Tumors were harvested from TBMs with or without LipC6 injection and used to prepare cell lysates. The expression level of pAKT and AKT in tumors in the indicated TBMs were detected by western blotting.

Our previous in vitro studies indicated that AKT phosphorylation mediates the resistance of HCC cells to apoptosis[16]. We found that HCCs also express high levels of phosphorylated AKT which could be downregulated by LipC6 injection (FIG. 12). In addition, LipC6 injection was found to decrease levels of Ki67 and CD31 but increase levels of cleaved caspase 3 and necrosis (FIG. 2F). These results indicate that LipC6 monotherapy suppresses tumor cell proliferation and vascularization but increases apoptosis and necrosis. Together, the in vitro and in vivo findings suggest LipC6's inherent tumoricidal effect on HCCs is due, at least in part, to its suppression of Akt signaling.

LipC6 Injection Modulates the Frequency and Function of TAMs in TBMs

Figure 3D:
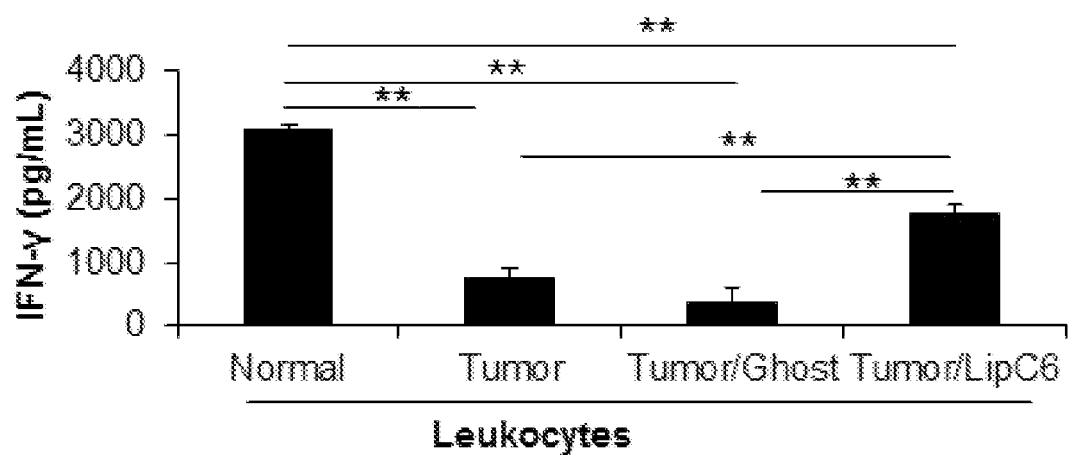
FIG. 3 shows images of flow cytometry (A-C) and graphs (D-E) of experiments showing LipC6 injection reduces suppressive function of TAMs. Size-matched TBMs were randomly assigned to one of three groups and received vehicle, LipC6, or no injection for two weeks. Normal mice served as a control. TILs in tumors and liver-resident lymphocytes (LRLs) in livers were harvested after liver perfusion and used to perform the following studies. A portion of TILs and LRLs were labeled with antibodies against CD4, CD25, FoxP3, F4/80, and CD11b, followed by performance of flow cytometry. (A) Quantitated Gr-1$^+$CD11b$^+$MDSCs are shown. (B) Quantitated CD4$^+$CD25$^+$FoxP3$^+$Tregs in CD4$^+$ T cells are shown. (C) Quantitated CD11b$^{+F}$4/80$^+$ MΦs in TILs and LRLs are shown. (D) 1×10$^5$ TILs were seeded in 96-well plates and cultured for 48 hours in the presence of anti-CD3 (1 µg/ml) and anti-CD28 (1 µg/ml). IFN-γ concentration in the cultured supernatant was measured by ELISA. Quantitative data for IFN-γ production in TILs are shown. (E) LipC6 injection results in the reduction of macrophage suppressive function. TILs were prepared from mice as indicated and used to isolate TAMs by plastic adherence. Prepared TILs suspended in tissue culture media were seeded in cell culture plates at a concentration of 1×10$^6$ cells/cm$^2$ surface area. Cultures were incubated for 45 mins at 37° C., then washed three times with media, the remaining adherent cells that was >90% CD11b$^+$ and used as macrophages. 3×10⁴ macrophages from each mouse with the indicated injection were co-cultured with 1×10⁵ RCs from splenocytes of wild type C57BL/6 mice by depleting adherent cells with plastic adherence. After stimulation with 1 µg/ml of anti-CD3 Ab and 1 µg/ml of anti-CD28 Ab for 48 hours, IFN-γ level in the culture supernatants was measured by ELISA. n=3; error bars represent means±SD. Asterisk represents significant difference (p<0.05).
Figure 3E:
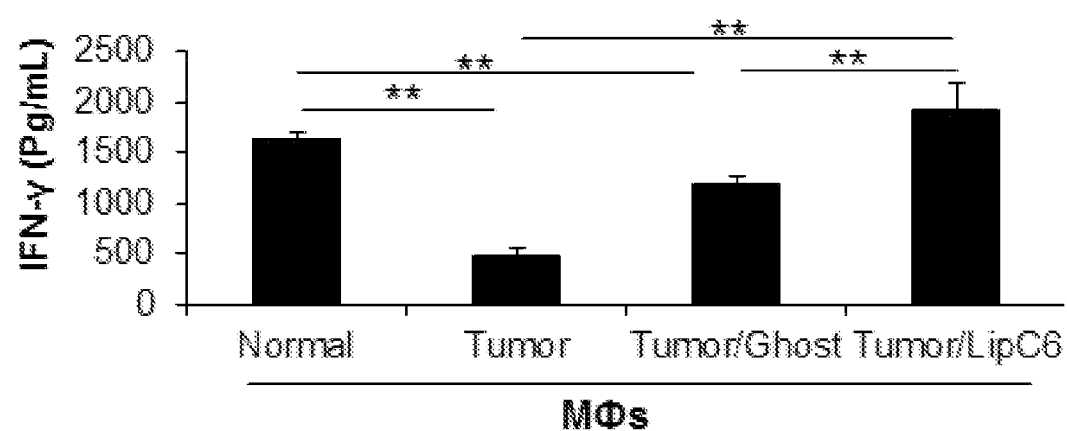
Figure 13A:
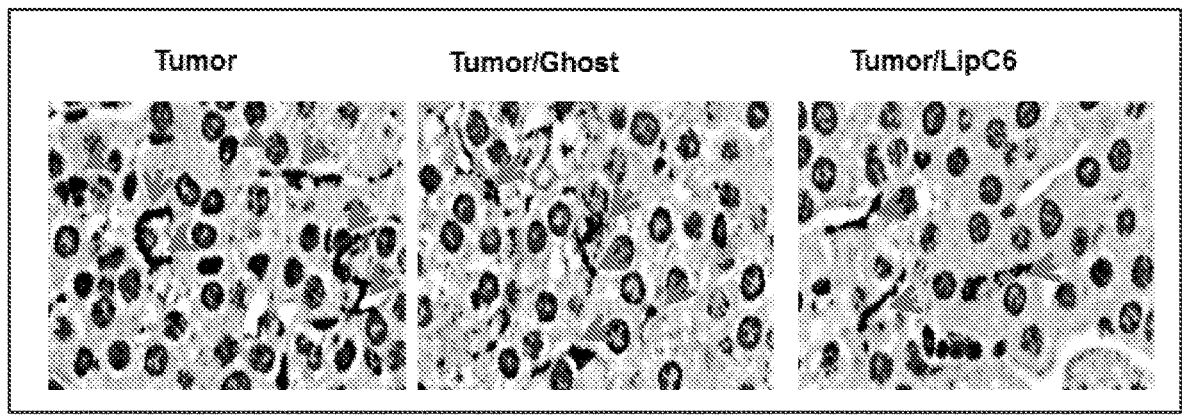
FIG. 13 is an image (A) of immunohistochemistry (IHC) images comparing F4/80 positive cells and DAPI positive cells and graph (B). Immunohistochemical staining of F4/80 and of the nucleus was performed in tumor tissues from HCC-bearing mice with vehicle, LipC6, or no injection. Representative images (A) and accumulated results (B) were shown. More F4/80⁺ macrophages were detected in tumors from HCC-baring mice without injection. Both LipC6 and vehicle injection led to reduction of F4/80⁺ macrophages in tumors with more reduction found in LipC6 injection (A). The average F4/80⁺ macrophages per 100 fields in tumor sections from the indicated HCC-bearing mice were calculated (B). 100× magnification, n=3, *p<0.05, **p<0.01, error bars represent mean±SDs.
Figure 13B:
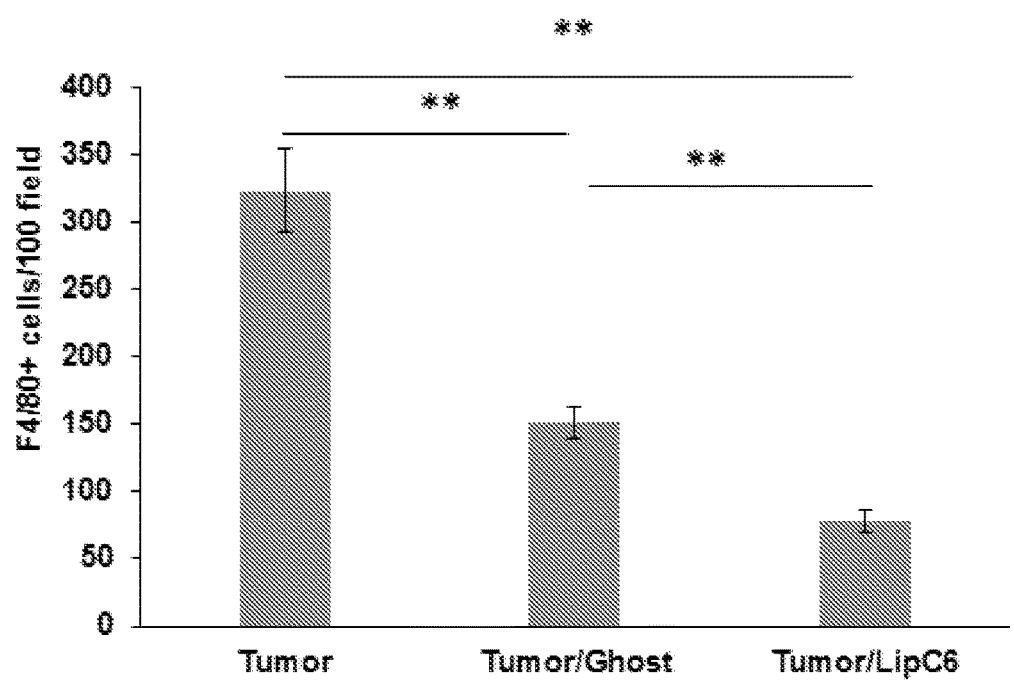
Figure 14A:
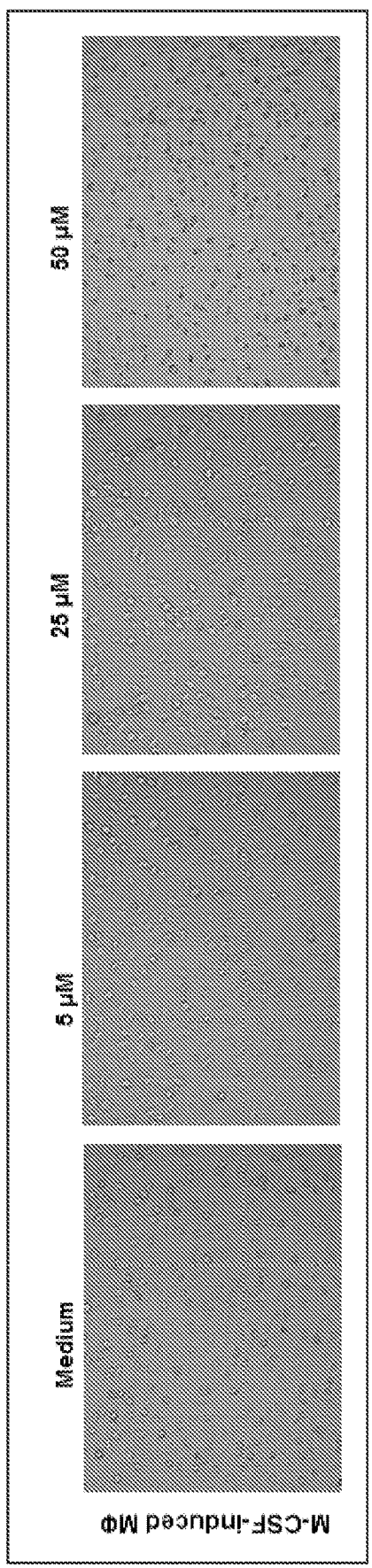
FIG. 14 shows images (A, B) and graphs (C) of experimental results showing in vitro study for LipC6 dose optimization. BMMs were prepared in vitro by stimulating bone marrow cells from wild-type C57BL/6 mice with GMCSF and MCSF for 6 days. G-BMMs or M-BMMs were incubated with LipC6 at different doses. Cell morphology was monitored microscopically to assess cellular physiology. Representative morphology of M-BMMs (A) and G-BMMs (B) 48 hours post incubation with the indicated dose of LipC6 are shown. Cell viability was determined with trypan blue exclusion. The accumulated percentage of surviving M-BMMs (C) and G-BMMs (D) was evaluated post-incubation with the indicated dose of LipC6. n=3; error bars represent±SD. *p<0.05, **p<0.01.
Figure 14B:
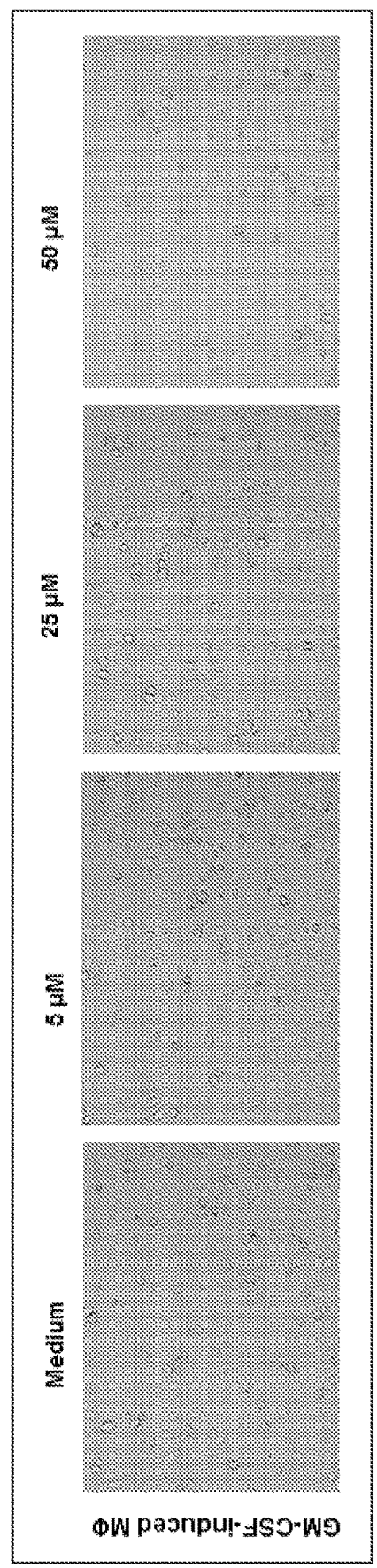
Figure 14C:
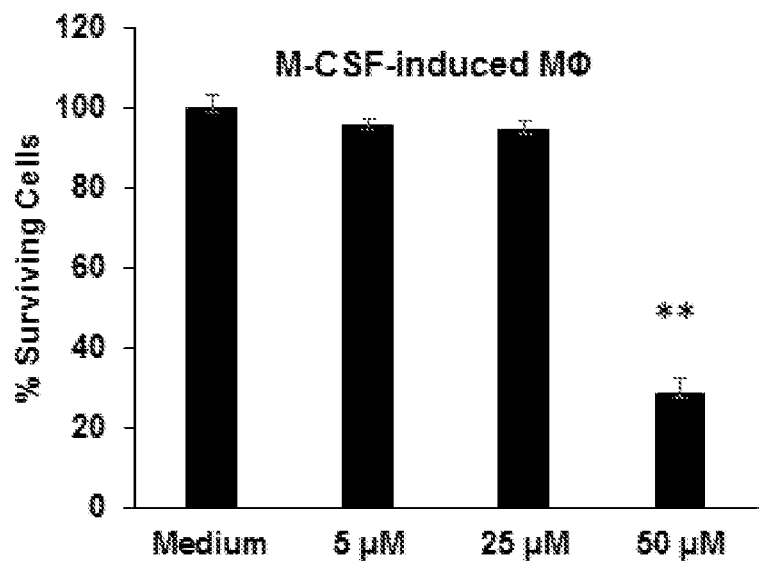
Figure 14D:
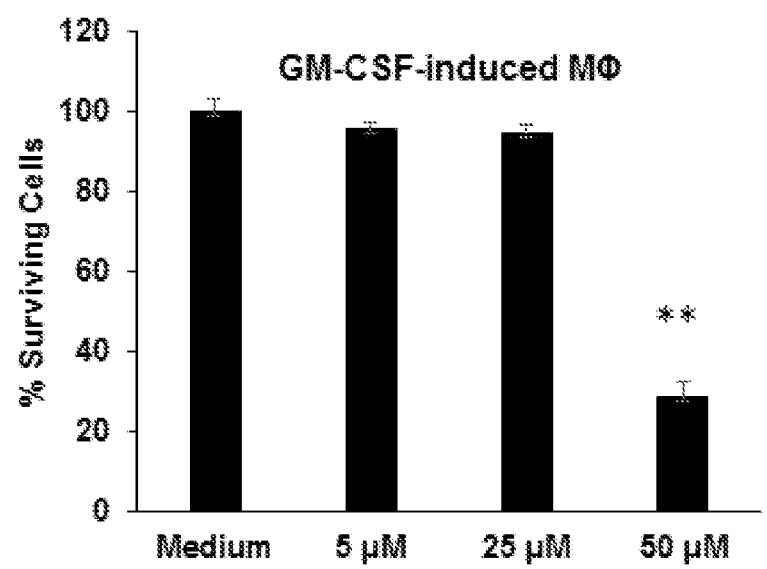
Figure 15A:
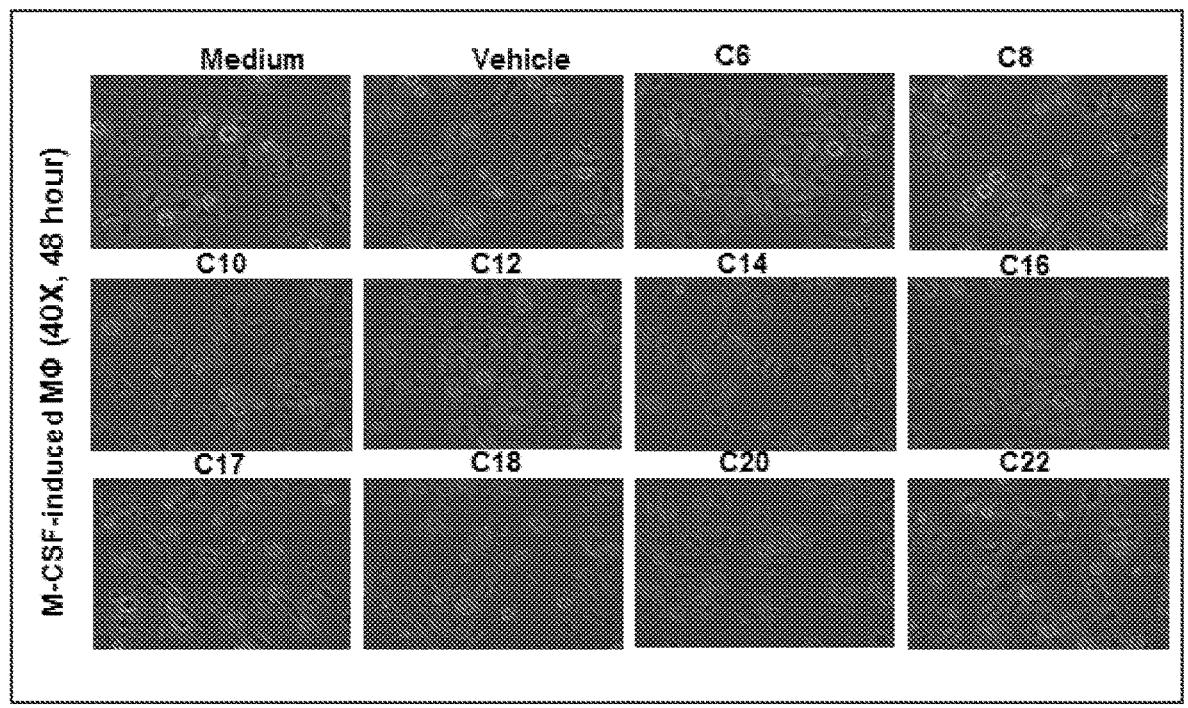
FIG. 15 shows images (A, B) and graphs (C, D) of experimental results showing functional comparison of ceramides with different chain lengths on suppression of $O^{2-}$ generation in BMMs. G-BMMs (A) and M-BMMs (B) were prepared in vitro by stimulating bone marrow cells from wild type C57BL/6 mice with GMCSF and MCSF for 6 days. After incubation with the ceramides of different carbon-chain lengths varying from 6 to 22 overnight, the relative ROS level in G-BMMs (C) and M-BMMs (D) was measured with a luminescence assay in accordance with the manufacturer's instruction. n=3; error bars represent±SD. * p<0.05.
Figure 15B:
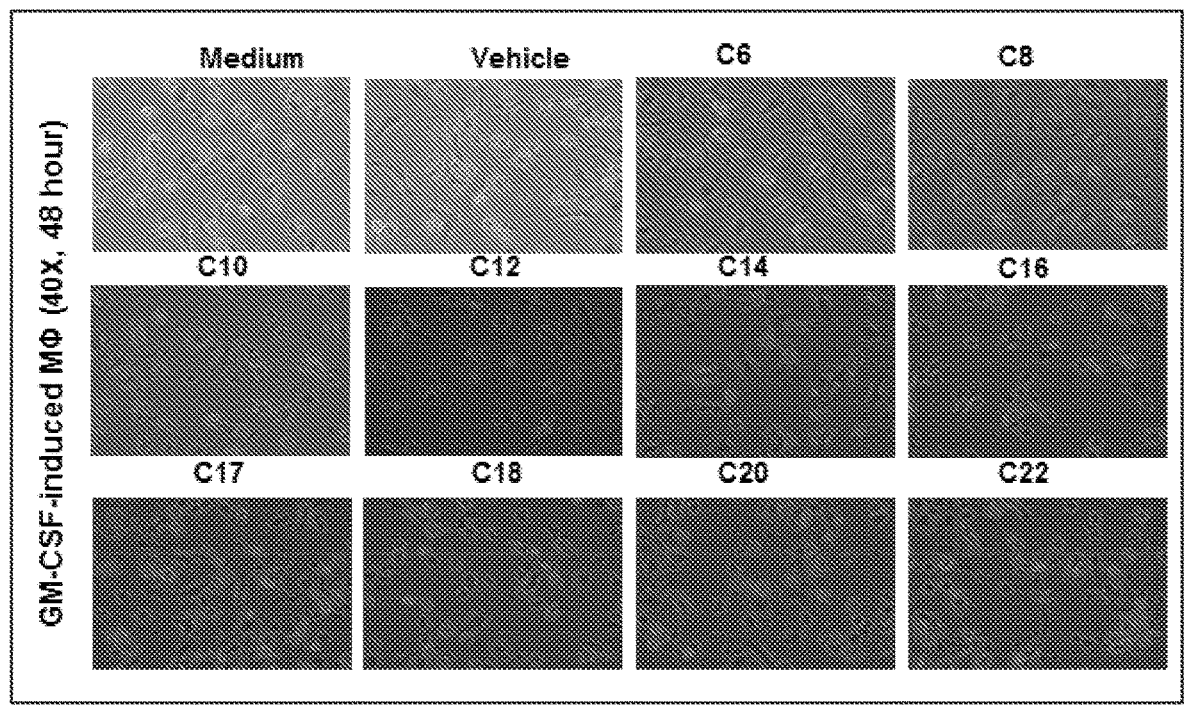
Figure 15C:
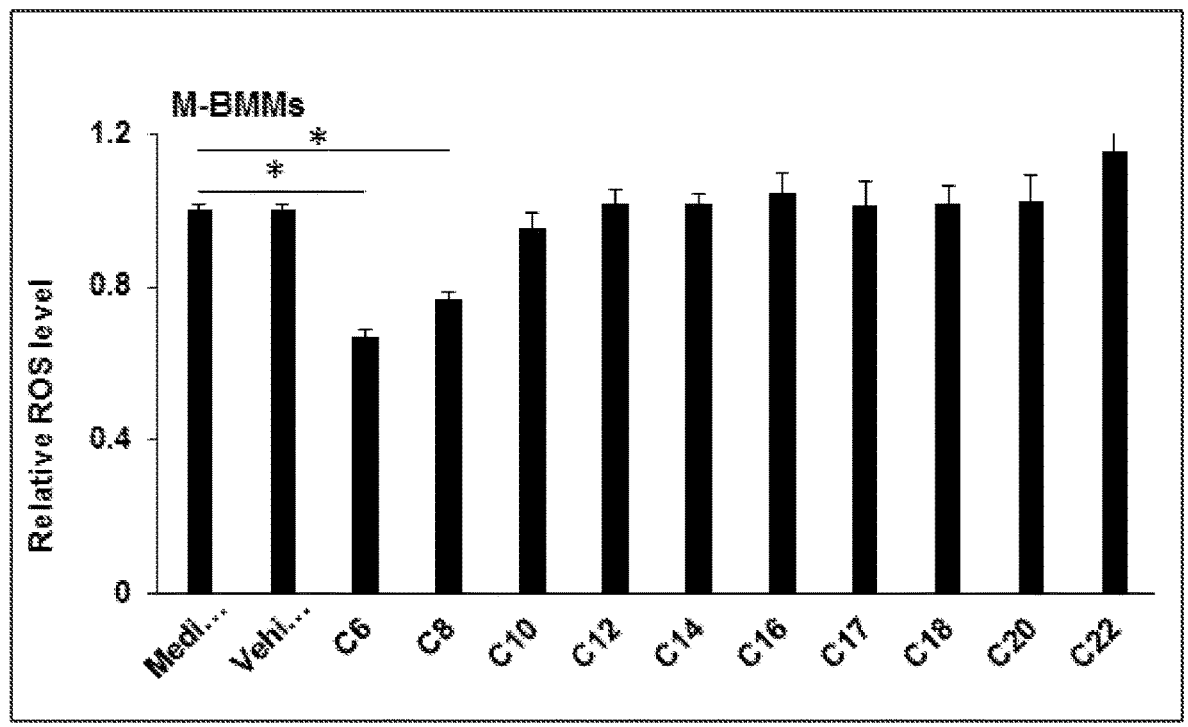
Figure 15D:
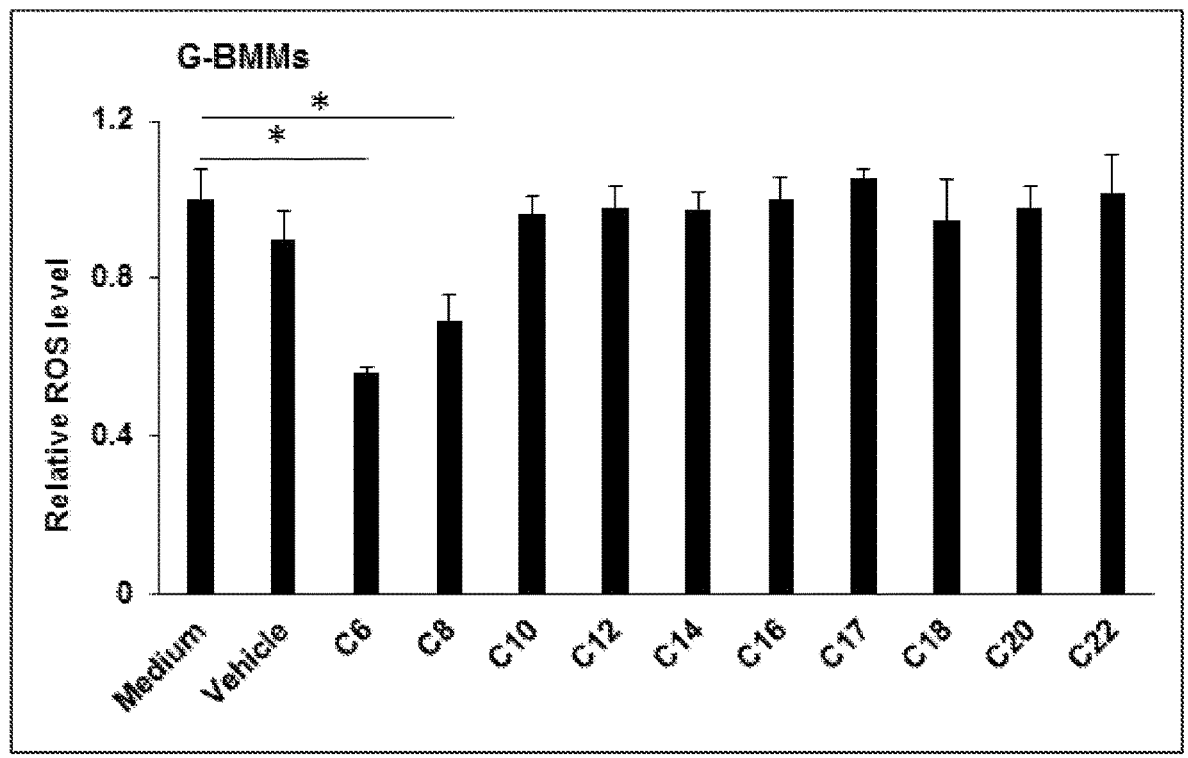

We next investigated the impact of LipC6 injection on immunosuppressive cell subsets in TBMs including typically recognized CD11b+Gr-1+ myeloid derived suppressor cells (MDSCs), CD4+CD25+FoxP3+ regulatory T cells (Tregs), and CD11b$^{+F}$4/80+ TAMs[26,27]. Flow cytometry analysis indicated that tumor progression led to a significant increase in the frequency of MDSCs (FIG. 3A), Tregs (FIG. 3B), and TAMs (FIG. 3C) in TILs compared to normal mice. LipC6 injection significantly reduced the magnitude of TAMs from 15% to 4% (FIG. 3B, FIG. 13), but has little impact on the frequency of MDSCs (FIG. 3A) and Tregs (FIG. 3B). ELISA analysis suggested that anti-CD3 and anti-CD28 were unable to effectively stimulate IFN-γ secretion in the mixed TILs from mice without LipC6 injection (700 pg/mL) or vehicle injection (400 pg/mL) (FIG. 3D). In contrast, LipC6 injection resulted in a significant increase in IFN-γ production (1700 pg/mL) in TILs. Next, TAMs were isolated from TILs (>90% isolated cells expressed CD11b+). Isolated TAMs were co-cultured with responder cells (RCs) from macrophage-depleted splenocytes of wild type mice. In response to stimulation with anti-CD3 and anti-CD28, TAMs from mice with vehicle or no injection largely suppressed IFN-γ production in RCs (FIG. 3E). In contrast, LipC6 injection blocked TAMs' suppressive effect and enabled RCs to produce 1800 pg/mL IFN-γ, equivalent to 1700 pg/mL produced in the presence of macrophages from normal mice (FIG. 3E). These results suggest that LipC6 injection reduces not only TAM frequency but also its suppressive function.

LipC6 Injection Results in Reduced Expression of M2-Like Markers in TAMs

Figures 4A, 4B:
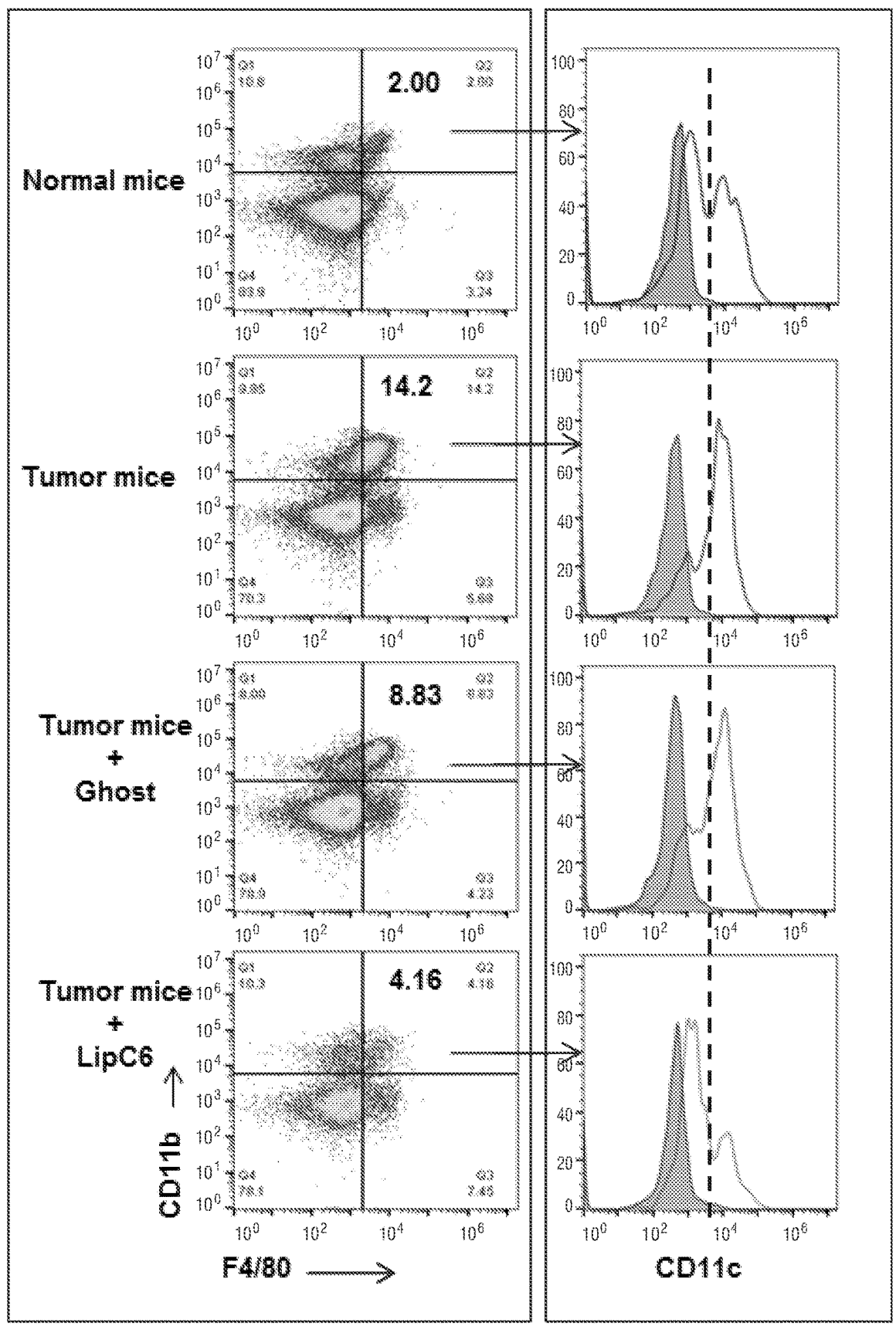
FIG. 4 shows images of flow cytometry (A) and graphs (B-F) of experiments showing LipC6 injection blocks upregulation of M2 macrophage markers. Size-matched TBMs were randomly assigned to one of three groups: vehicle, LipC6, or no injection. Normal mice served as additional controls. Two weeks after injection, TILs were isolated from the perfused tumors with PBS and stained with rat IgG isotype control, CD11b, F4/80, CD80, PD-L1. Flow cytometry was conducted to define the frequency of TAMs positive for both F4/80 and CD11b (A). In gated F4/80⁺ CD11b⁺TAMs, the expression of CD11c (B), PD-L1 (C), CD80 (D), and CD86 (E) was determined. Part of TILs were also used to isolate TAMs with anti-F4/80 MicroBeads. The total RNAs in the isolated TAMs were extracted and used to conduct real-time PCR for detecting the mRNA level of CD11c, PD-L1, CD80, and CD86 (F).
Figures 4C, 4D:
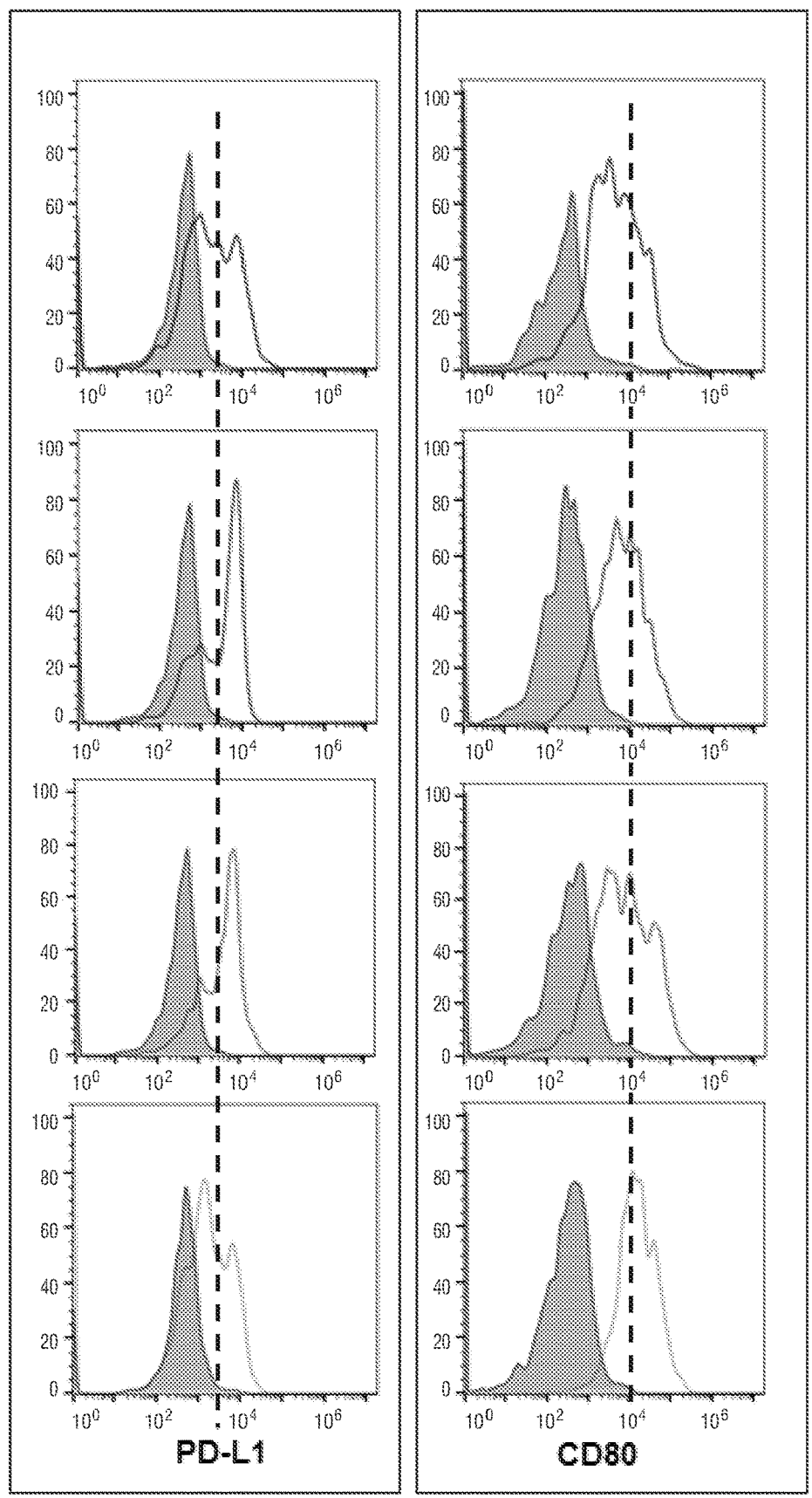
Figure 4E:
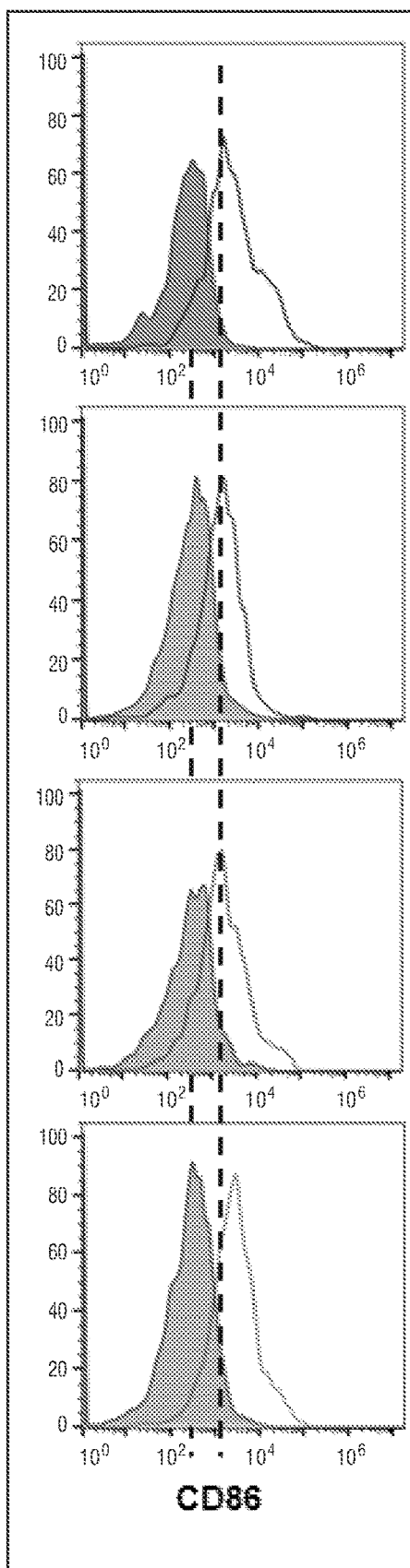
Figure 4F:
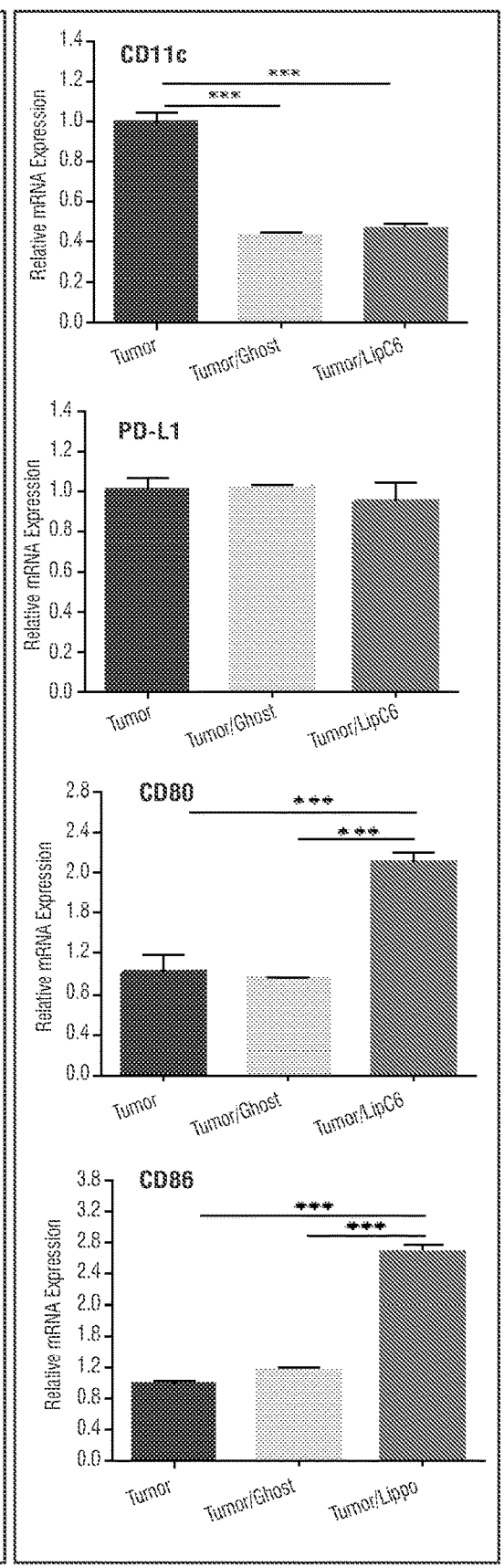

To document whether LipC6-induced alteration in TAMs may be accompanied by a shift in TAM phenotype, TILs were isolated from TBMs that received vehicle, LipC6, or no injection, then labeled with markers associated with classically activated (M1) or alternatively activated (M2) macrophages to conduct flow cytometry. Compared to normal mice, tumor growth induced an increase in the frequency of CD11b+F4/80+ macrophages (FIG. 4A) which contains a higher proportion of cells expressing M2 macrophage markers, including CD11c (FIG. 4B) and PD-L1 (FIG. 4C), while there was slight alteration in the expression of the M1 marker CD80 (FIG. 4D) and CD86 (FIG. 4E). LipC6 injection remarkably reduced the expression of CD11c (FIG. 4B) and PD-L1 (FIG. 4C) in CD11b+F4/80+ macrophages to the level seen in normal mice, but minimally altered the expression of CD80 (FIG. 4D) and CD86 (FIG. 4E). These data suggest that LipC6 injection suppresses the expression of M2-like markers in TAMs. Real-time PCRs suggest that LipC6 injection led to an increased mRNA expression of CD80 and CD86, reduced mRNA expression of CD11c, but no change was detected in PD-1 mRNA expression in TAMs (FIG. 4F). These results are not entirely consistent with the levels of protein expression, suggesting the likely translational regulation of PD-L1, CD80, and CD86.

LipC6 Injection Results in Reduced ROS Production by TAMs

Figure 5B:
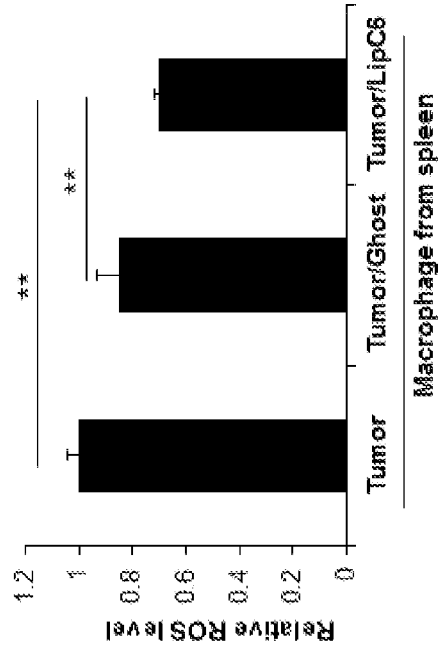
FIG. 5 shows graphs of experimental results showing LipC6 administration suppresses $O^{2-}$ generation in TAMs and BMMs. Size-matched TBMs were randomly assigned to one of three groups: vehicle, LipC6, or no injection. Two weeks after injection, splenic leukocytes and TILs were prepared from the spleen and the perfused tumors. The cells were incubated for 45 mins at 37° C., then washed three times with media, with the remaining adherent cells being >90% CD11b positive (macrophages). Intracellular ROS were measured with Glo™ $H_2O_2$ assay. Briefly, $H_2O_2$ substrate was added to each well followed by addition of ROS-Glo™ detection solution. After incubation for 20 minutes at RT, relative luminescence was measured to assess ROS level in TAMs (A) and splenic macrophages (B). Similarly, bone marrow-derived macrophages (BMMs) were prepared in vitro by stimulating bone marrow cells from wild type C57BL/6 mice with GMCSF (G-BMMs) and MCSF (M-BMMs) for 6 days. After incubation with LipC6 or vehicle overnight, the relative ROS level in G-BMMs (C) and M-BMMs (D) were measured. n=3; error bars represent±SD. *p<0.05, **p<0.01.

To elucidate the mechanism by which LipC6 phenotypically and functionally modulates TAMs, we investigated the injection of LipC6 on ROS production, a critical factor in modulation of TAMs[22]. Using a luminescent assay, we found a 60% decrease in ROS production in TAMs from LipC6-injected TBMs (FIG. 5A) and a 30% reduction in vehicle-injected mice relative to control mice without injection. A similar reduction in ROS was observed in macrophages isolated from the spleen of TBMs with LipC6 injection (FIG. 5B).

Figure 5D:
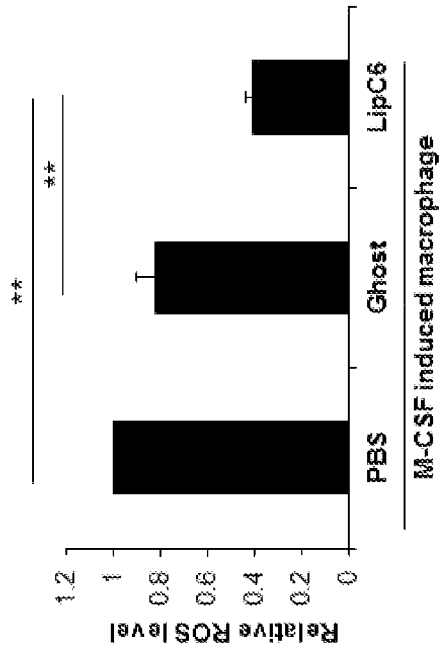
Figure 5A:
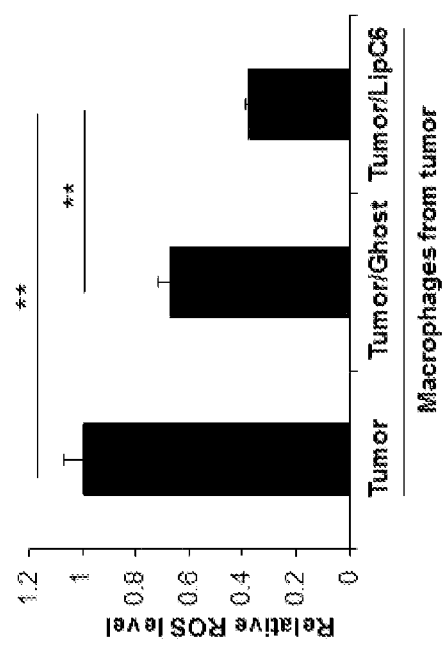
Figure 5C:
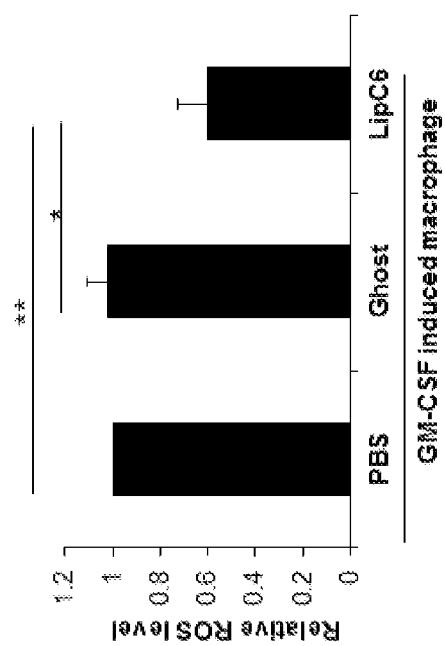
Figure 16A:
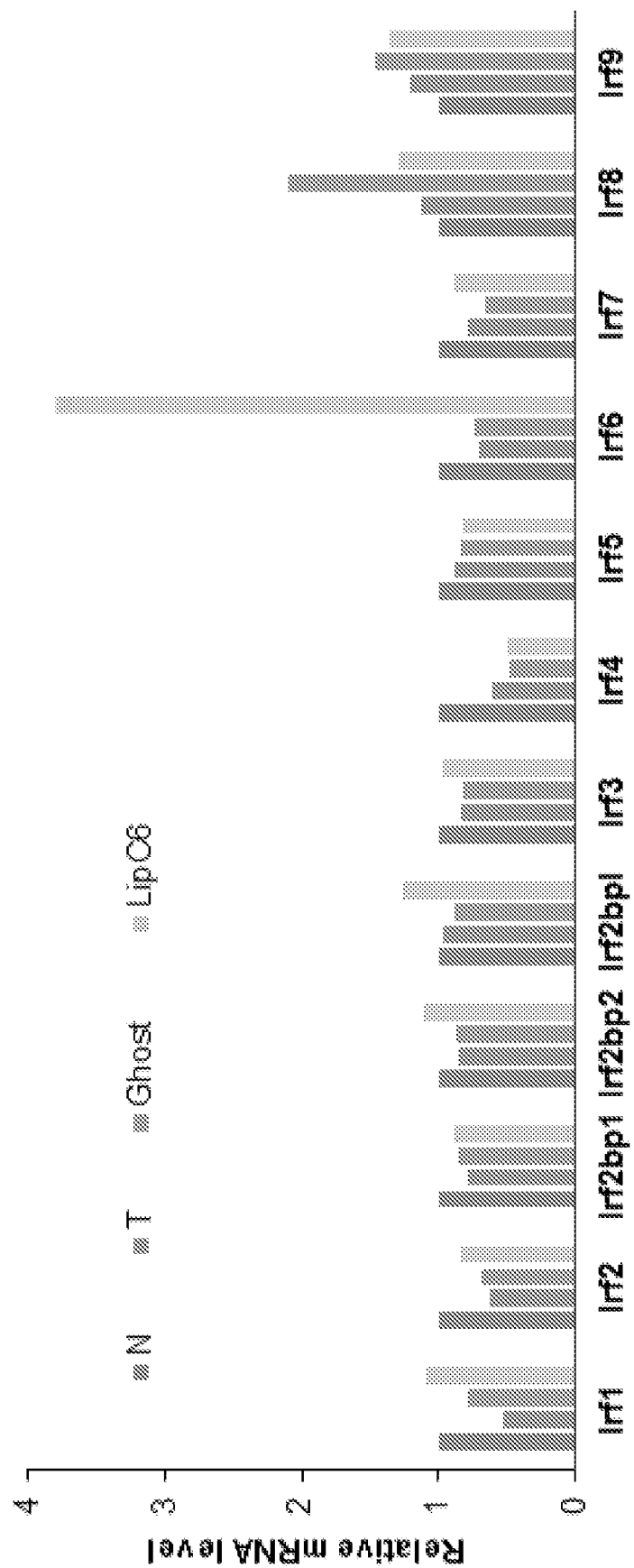
FIG. 16 shows graphs of experimental results showing LipC6 injection leads to alteration in expression of IRF family genes in TAMs. (A) RNA-seq assay. TBMs received vehicle, LipC6, or no injection as described previously. TAMs were isolated from each mouse to extract mRNA to perform RNA-seq in UCLA clinical microarray core with macrophages from wild-type mice as control. (B) Real time PCR assay. TAMs were purified from TBMs and incubated with LipC6 and vehicle for 24 hours prior to RNA isolation. Real-time PCR assays demonstrated the alteration in the expression of IRF family genes.
Figure 16B:
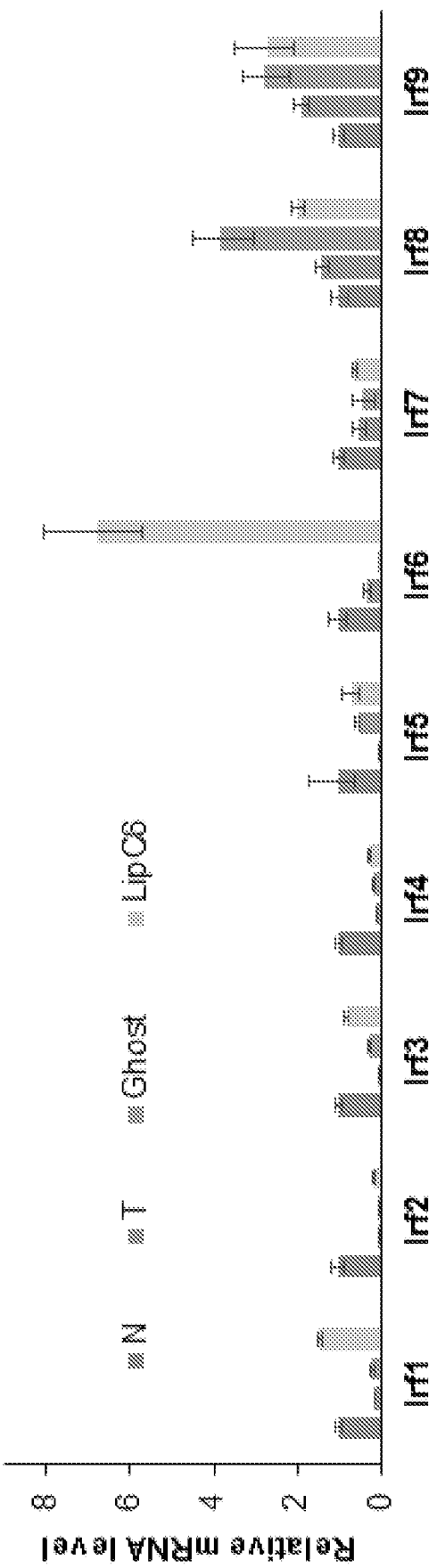
Figure 17A:
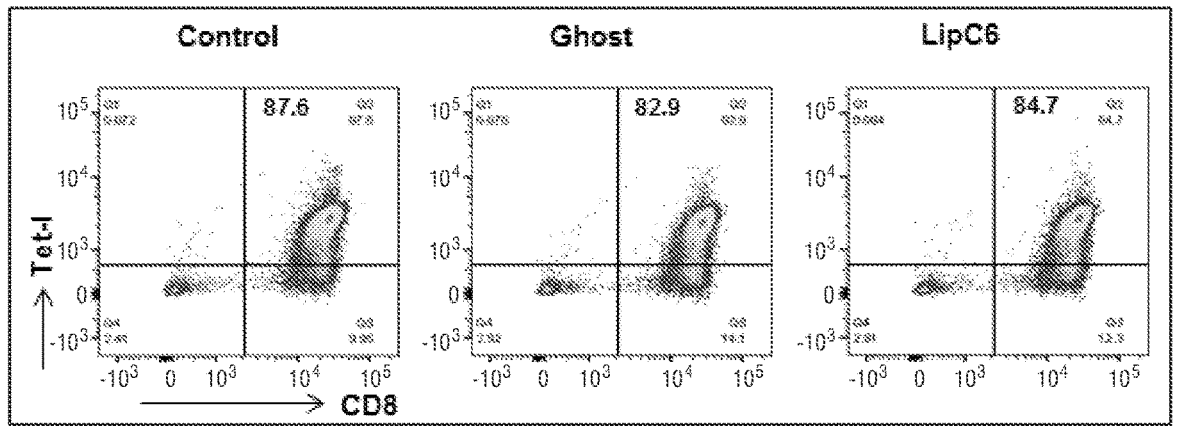
FIG. 17 shows images (A, C, E) and graphs (B, D, F) of experimental results showing LipC6 does not directly impact TAS CD8+ T cells. TAS CD8+ T cells were isolated from the spleen of line 416 mice, which transgenically expresses TCR for tumor specific antigen epitope-I. The isolated TCR-I+ T cells were incubated with vehicle, or LipC6. The second day, these cells were washed with medium, then incubated with DCs and stimulated with TAS peptide-I in the absence or presence of Brefeldin A. The cells in the absence of Brefeldin A were used to detect Ki67 expression and proliferation of Tet-I+ T cells after a 24-hour stimulation. The cells in the presence of Brefeldin A were used to detect IFN-γ production 5 hours post stimulation. Flow cytometry was conducted to analyze these cells after staining with fluorochrome-conjugated antibodies for Ki67, Tetramer-I, or IFN-γ. The results showed that no significant difference for Ki67+CD8+ T cells, Tetramer-I+CD8+ T cells and IFN-γ+CD8+ T cells was detected in the cells with or without LipC6 incubation. These results suggest that LipC6 may not directly impact TAS CD8+ T cells. However, in vivo injection of TBMs with LipC6 activates TAS CD8+ T cells which is involved in LipC6-mediated polarization of TAMs by the ROS signaling pathway. Together, LipC6 would indirectly function on TAS CD8+ T cells through modulating TAMs via the ROS signaling pathway.
Figure 17B:
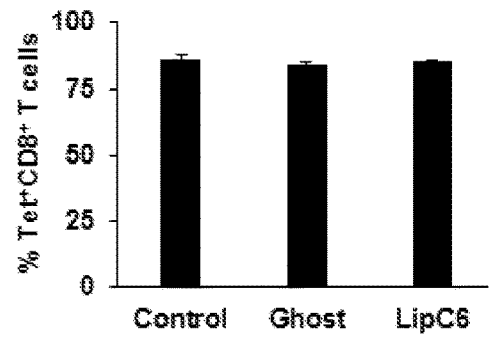
Figure 17C:
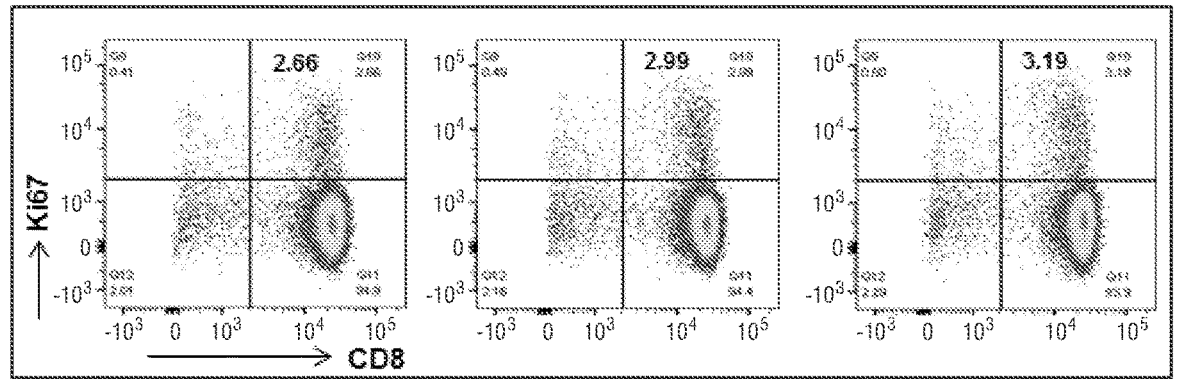
Figure 17D:
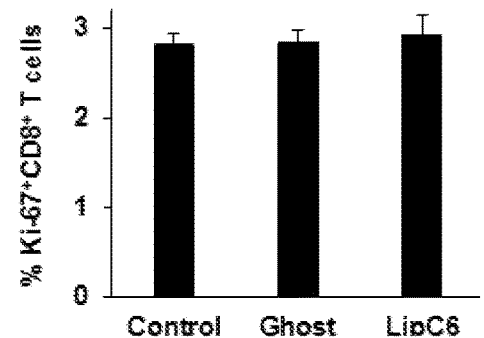
Figure 17E:
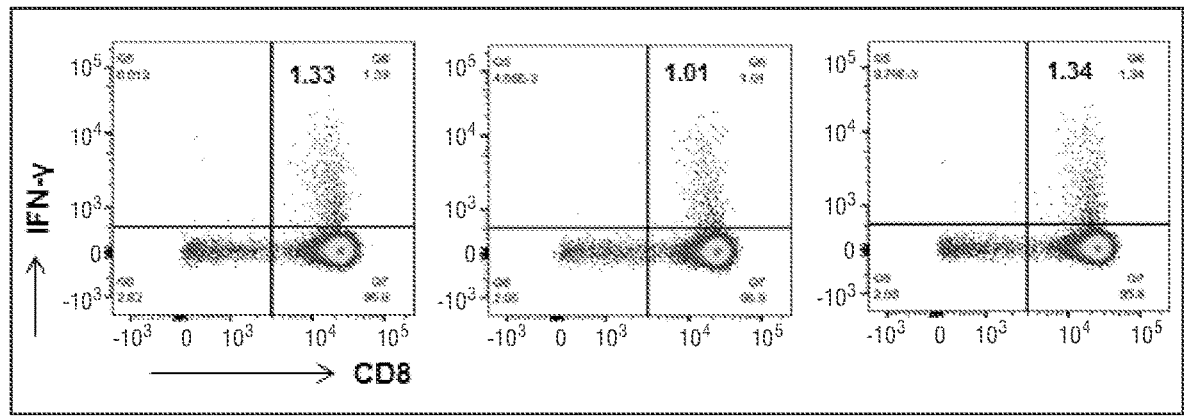
Figure 17F:
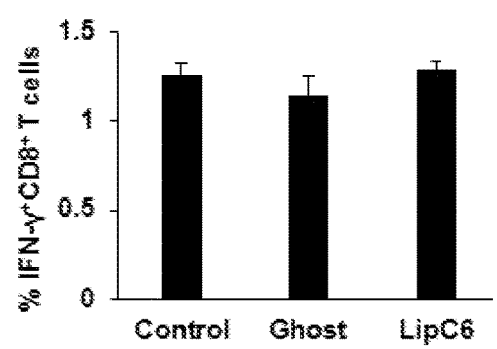
Figure 18A:
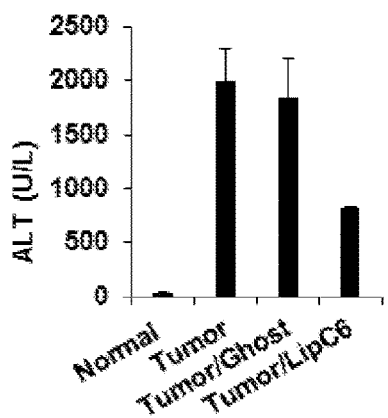
FIG. 18 shows graphs of experimental results showing toxicity of LipC6 in TBMs. Size-matched TBMs were assigned into one of three groups: vehicle, LipC6, or no injection. Two weeks after injection, mice were examined and then anesthetized to harvest whole blood, plasma, and pathologic specimens. Normal mice were used for control. Clinical assessment, blood analysis, and pathologic evaluation were carried out in the Veterinary Medical Diagnostic Laboratory at the University of Missouri College of Veterinary Medicine. Liver toxicity was assessed by measurement of (A) alanine aminotransferase (ALT), (B) aspartate aminotransferase (AST), (C) alkaline phosphatase (ALP), (D) albumin, (E) total protein, (F) glucose, and bilirubin (data not shown); renal toxicity was assessed by measuring (G) blood urea nitrogen (BUN) and (H) creatinine, which indicate the glomerular filtration rate (GFR); hematologic toxicity was evaluated by measuring (I) white blood corpuscles (WBC), (J) red blood corpuscles (RBC), (K) hemoglobin (HGB), (L) hematocrit (HCT), (M) mean corpuscular volume (MCV), (N) mean corpuscular hemoglobin (MCH), (O) mean corpuscular hemoglobin concentration (MCHC), (P) minimum platelet count (MPC) and (Q) reticulocyte count; cardiac toxicity was evaluated by measuring troponin I. There was no detectable alteration among all TBMs (data not shown).
Figure 18B:
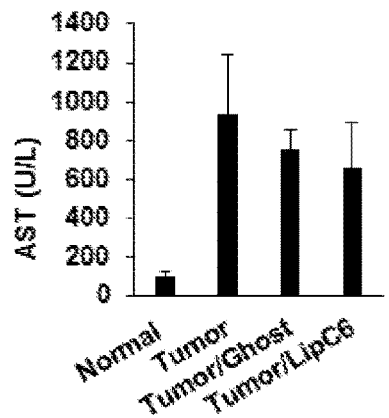
Figure 18C:
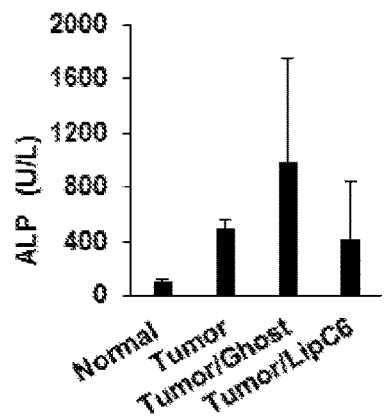
Figure 18D:
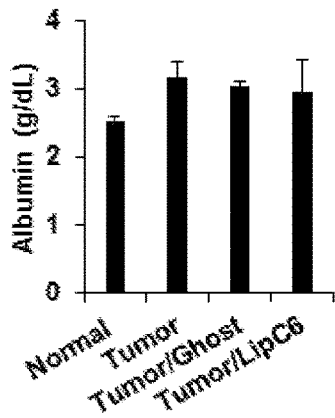
Figure 18E:
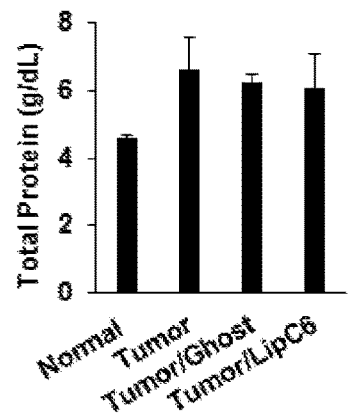
Figure 18F:
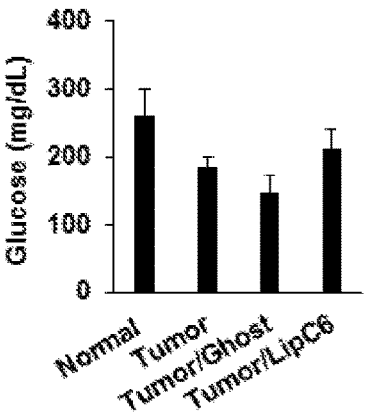
Figure 18G:
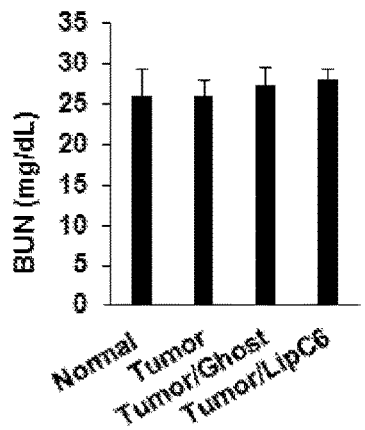
Figure 18H:
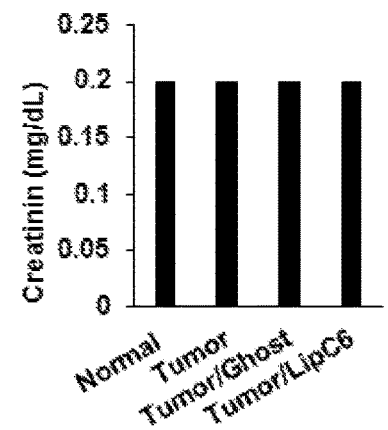
Figure 18I:
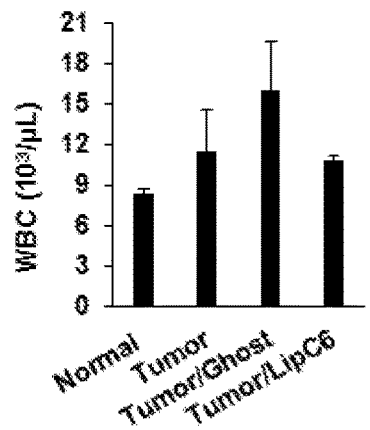
Figure 18J:
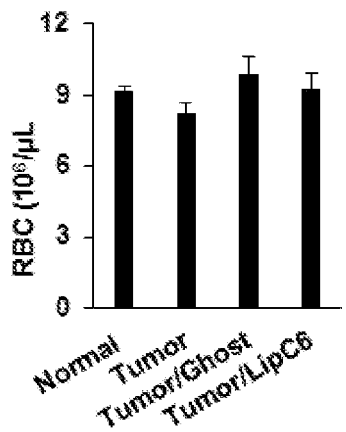
Figure 18K:
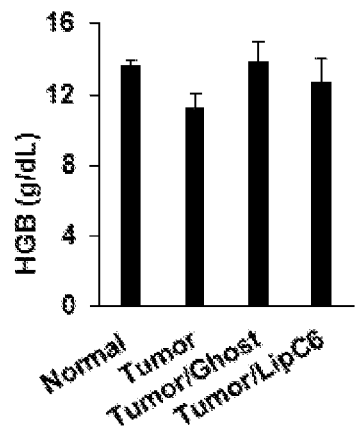
Figure 18L:
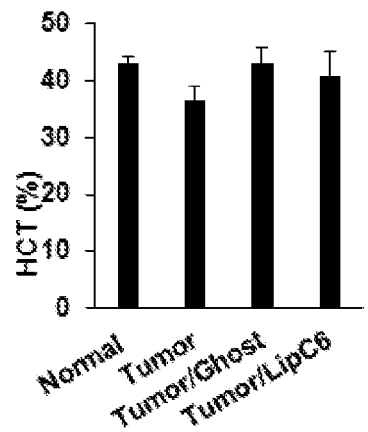
Figure 18M:
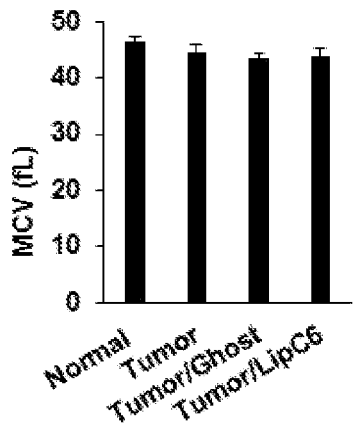
Figure 18N:
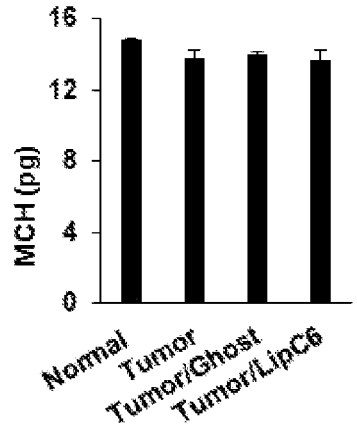
Figure 18O:
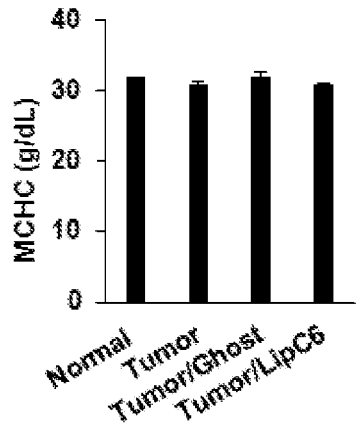
Figure 18P:
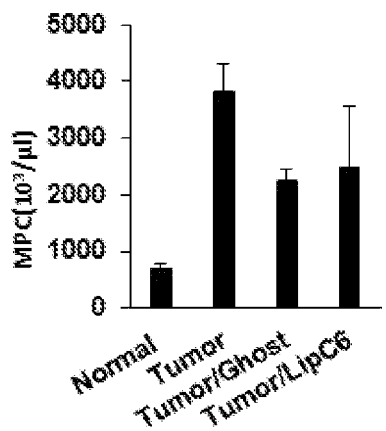
Figure 18Q:
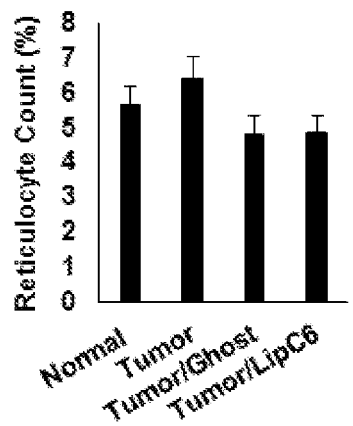

To investigate whether LipC6 similarly modulates ROS production in M1 macrophages and M2 macrophages, we generated M1-like or M2-like bone marrow-derived macrophages (BMMs) by stimulating bone marrow cells from wild type C57BL/6 mice with GMCSF or MCSF[28,29]. Subsequently, BMMs were incubated with LipC6 for 24 hours at a selected dose of 25 μM (FIG. 14), then ROS levels in M1 or M2 BMMs was measured. We found that LipC6 incubation significantly blocked ROS production in both GMCSF-induced M1 BMMs (FIG. 5C) and MCSF-induced M2 BMMs (FIG. 5D). This suppressive effect on ROS production was only detected in C6- and C8-ceramides in contrast to the longer chain ceramide species (FIG. 15). We speculate that exogenous chain species have optimal biophysical properties to intercalate into macrophages and induce structured membrane micro domains. Thus, both in vivo and in vitro data suggest that LipC6 significantly suppresses ROS production independent of macrophage phenotypes. The further studies indicate that interferon-regulatory factors (IRFs) may represent an underlying molecular mechanism. We found that LipC6 injection significantly regulate IRF1, 2, 3, and 6 in TAMs; furthermore, these results were validated by ex vivo incubation of TAMs with LipC6 (FIG. 16).

Figure 6A:
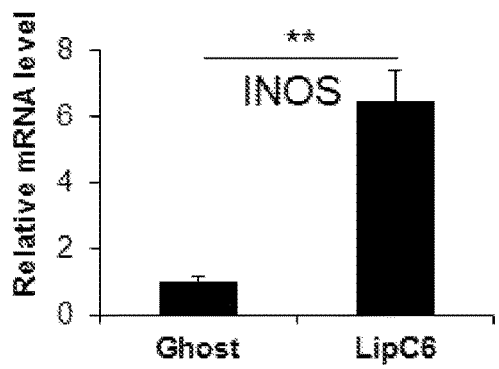
FIG. 6 shows graphs of experimental results showing LipC6 enhances M1 cytokine production and inhibits M2 cytokine production in mouse G-BMMs and M-BMMs. G-BMMs and M-BMMs were prepared in vitro by stimulating bone marrow monocytes from wild type C57BL/6 mice with GMCSF and MCSF respectively for 6 days. The prepared G-BMMs or M-BMMs were subsequently incubated with 25 µM LipC6 or vehicle for 24 hours, the total RNAs are isolated and subjected to real-time PCRs for quantitating enzyme INOS (A) and M1 cytokines in G-BMMs including IL-12 (B), IFN-γ (C), TNF-α (D); enzyme ARG1 and M2 cytokines in M-BMMs including, IL-4 (E), FIZZ (F) and YM1 (G). n=3; error bars represent±SD. *p<0.05, **p<0.01.
Figure 6B:
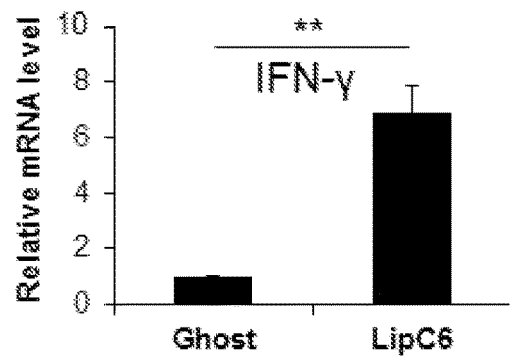
Figure 6C:
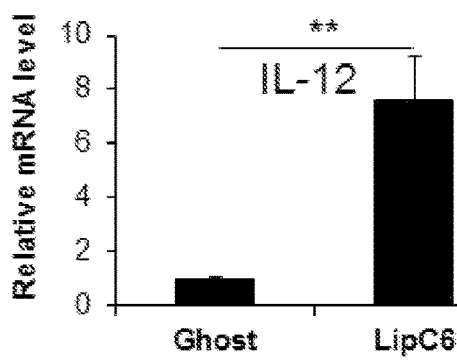
Figure 6D:
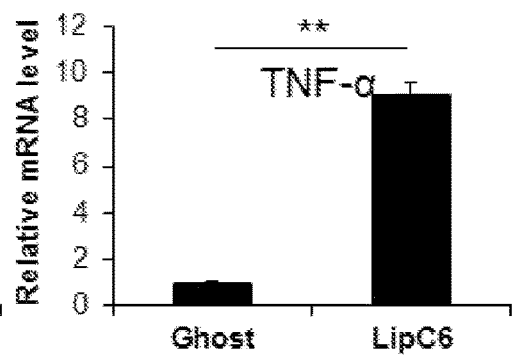
Figure 6E:
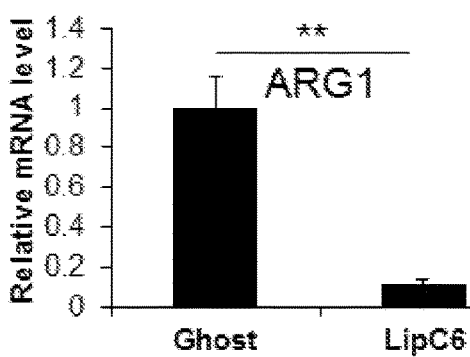
Figure 6F:
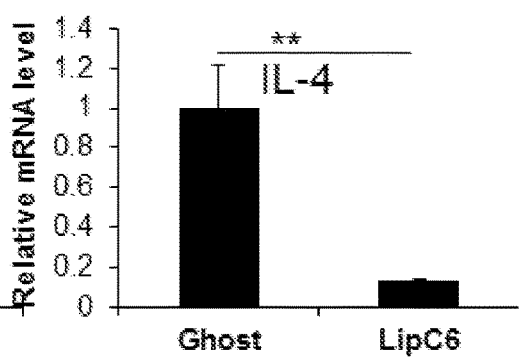
Figure 6G:
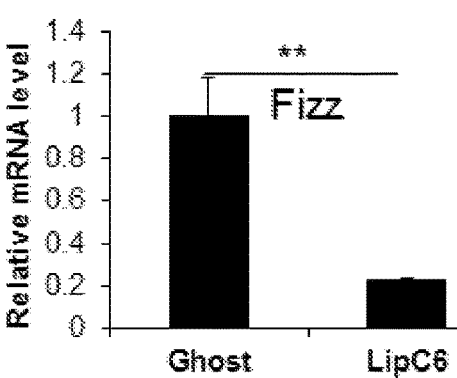
Figure 6H:
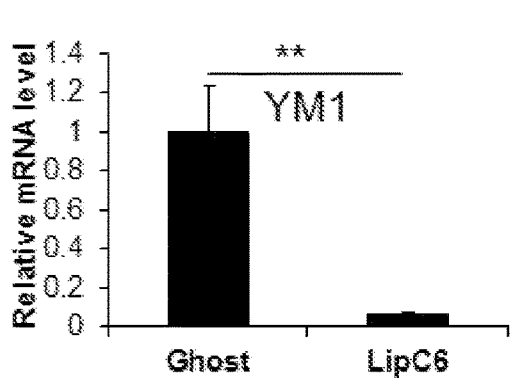

LipC6 Enhances M1 Cytokine Production and Inhibits M2 Cytokine Production in Mouse BMMs To investigate whether LipC6 incubation differentially regulates enzyme and cytokine production in GMCSF-induced M1 and MCSF-induced M2 BMMs, M1 and M2 BMMs were incubated with LipC6 or vehicle for 24 hours. Real-time PCRs indicated that LipC6 incubation significantly promoted production of enzyme iNOS (FIG. 6A) and M1 cytokines in M1 BMMs including, IL-12 (FIG. 6B), IFN-γ (FIG. 6C), and TNF-α (FIG. 6D). Conversely, LipC6 incubation significantly suppressed the production of enzyme Argl (FIG. 6E) and M2 cytokine in M2 BMMs including, IL-4 (FIG. 6F), Fizz (FIG. 6G), and Ym1 (FIG. 6H). These data suggest that LipC6 promoted M1 activation in GMCSF-induced BMMs but suppressed M2 activation in MCSF-induced M2 BMMs.

ROS are required for LipC6-mediated modulation of macrophages

Figure 7A:
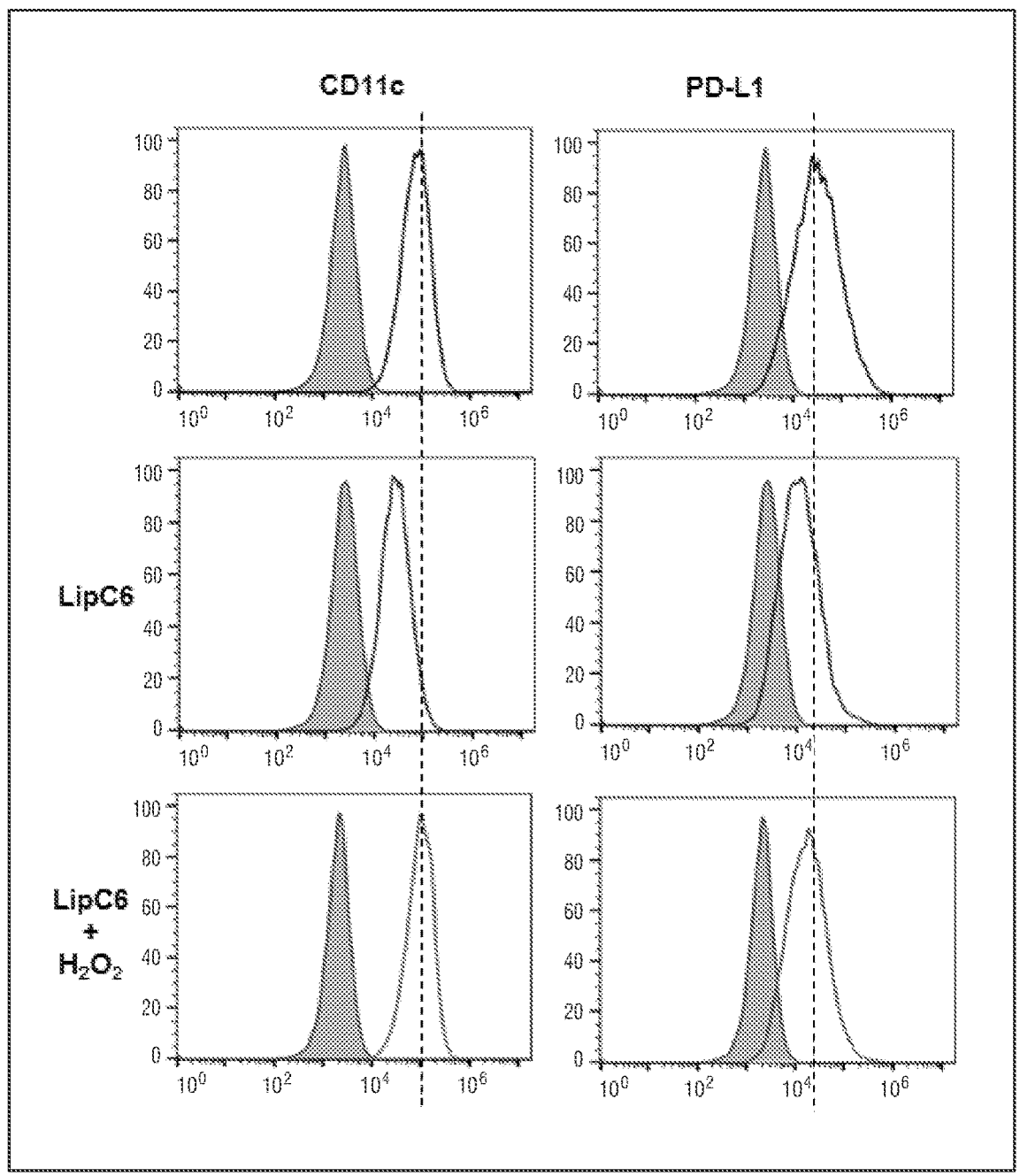
FIG. 7 shows graphs of experimental results showing impact of LipC6 on phenotype and cytokine production in bone marrow-derived macrophages. Bone marrow derived monocytes were stimulated with MCSF for 6 hours followed by incubation with LipC6 for 2 hours in the presence or absence of $H_2O_2$. Cells were subjected to flow cytometry after labeling with antibodies for F4/80, CD11b. CD11c, and PD-1. CD11c or PD-L1 positive cells in the gated F4/80⁺ CD11b⁺ macrophage population is shown (A). GM-BMMs were prepared in vitro by stimulating bone marrow derived monocytes from wild type C57BL/6 mice with 50 ng/mL GMCSF for 6 days. GM-BMMs were incubated for 24 hours with 25 µM vehicle, 25 µM LipC6, 50 µM NAC or LipC6 plus NAC. Total RNA was extracted and subjected to RT-PCR to quantitate M1 cytokines including iNOS (B), IL-12 (C), IFN-γ (D) and TNF-α (E). n=3, *=p<0.05 and **=p<0.001 using Student's t-test.
Figure 7B:
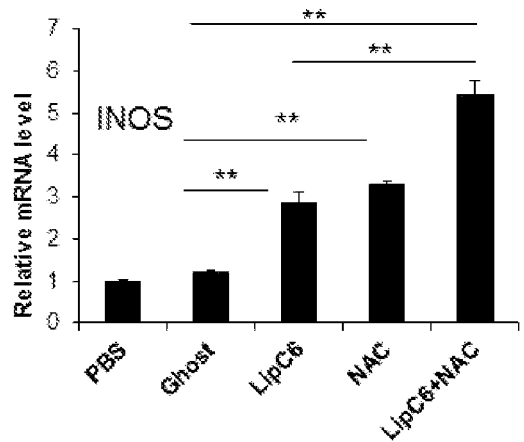
Figure 7C:
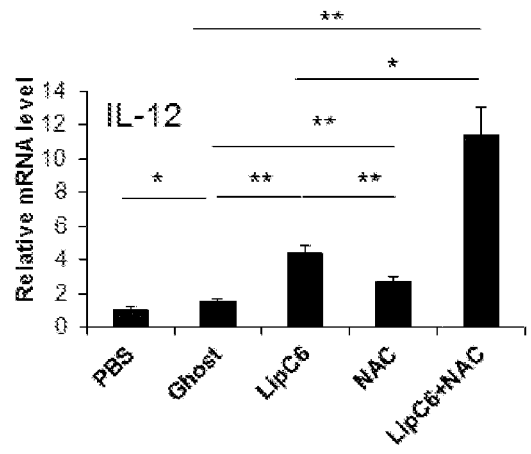
Figure 7D:
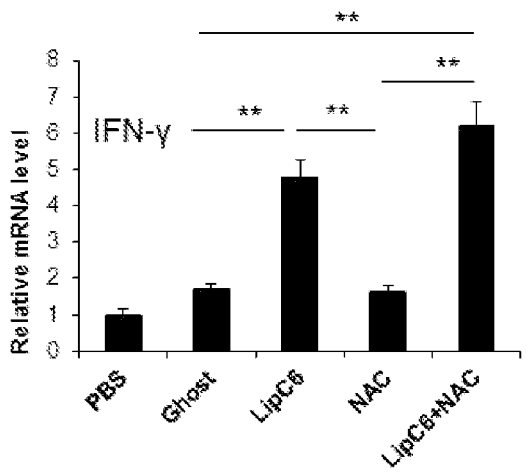
Figure 7E:
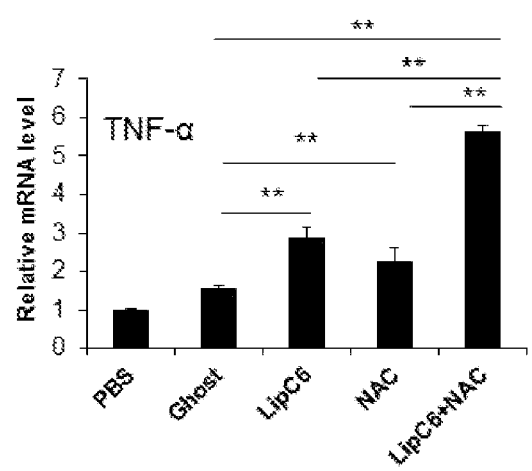

To further investigate whether ROS are a critical regulator in LipC6-mediated modulation of macrophages, bone marrow-derived monocytes were stimulated with MCSF for six hours followed by incubation with LipC6 for two hours in the presence or absence of $H_2O_2$. Flow cytometric analysis demonstrated that the addition of $H_2O_2$ compensated LipC6-mediated reduction in the expression of PD-L1 and CD11c (FIG. 7A) in the resultant cells. To further study if ROS signaling is required for LipC6-mediated modulation of macrophages, we compared the function of LipC6 and the ROS specific inhibitor N-acetyl-L-cysteine (NAC) in modulating M1 cytokine production in GMCSF-induced macrophages. Detection of different cytokine mRNAs with real-time PCR showed that LipC6 incubation resulted in increased M1 cytokine production including iNOS, IL-12, IFN-γ and TNF-α (FIGS. 7B-6E). This profile was similar to that induced by NAC incubation. In addition, the combination of LipC6 and NAC had a greater effect than either compound alone. Taken together, these results suggest LipC6 modulates BMMs by inhibiting ROS signaling.

DISCUSSION

The present studies reveal a novel role of ceramide nanoliposomes such as LipC6 in breaking tumor-induced immunotolerance in cancer such as HCC, which is confirmed by eradication of established tumors via its combination with an ACT and immunization approach. The inherent p-AKT-dependent tumoricidal activity of ceramide together with the ability to reverse tumor-induced immunotolerance offers the promise of utilizing LipC6 as a significant anticancer therapeutic component that can be integrated into cancer immunotherapy.

Our data show that LipC6 has immunomodulatory effects in addition to its inherent tumoricidal properties. This result is consistent with a previous report indicating that the antitumor activity of some conventional drugs is, in part, associated with their ability to re-activate the anti-tumor immune response[30]. Our current findings suggest that development of LipC6-combined strategy, which both maximizes tumor control and facilitates antitumor immune activity, are expected to achieve long-term clinical benefit in HCC[31-33]. As shown in our current studies, LipC6 monotherapy decreases tumor growth but was unable to eliminate tumors or block further progression. Integration of LipC6 with TAS ACT and immunization resulted in the regression of established tumors (FIGS. 1A-1D). These results suggest that LipC6 injection effectively blocks anergy of effector CD8+ T cells, allowing the response to immunization to exert cytotoxic function against established tumors. This immunomodulatory function on TAS CD8+ T cells may be generated by LipC6's indirect effect, as no direct activation was detected in LipC6-administrated TAS TCR-I T cells (FIG. 17). Therefore, LipC6 is not only a tumoricidal reagent but also a strong immunomodulatory factor. These synergistic anti-tumor activities plus the clinically feasible delivery of nanolipsomes highlight the considerable potential for LipC6-intergrated immunotherapies to translate into therapy for HCC and other cancers.

Ceramide plays important roles in both cell structure and signaling in multiple cell types including immune cells[34]. Our group has shown that LipC6 exerts tumoricidal activity in HCC[16] and other cancers[19,35,36]. Extensive preclinical evaluation of LipC6 has been led to the very recent approval of the IND application regarding its safety in patients with solid tumors (109471). Also, no toxicity was detected in LipC6-administrated HCC-bearing mice by evaluating liver enzymes, kidney function, hematological toxicity (FIG. 18) and cardiac toxicity (data not shown). However, very little is known about the function of ceramide in antitumor immunity. We found that LipC6 injection blocks the onset of tolerance of TAS CD8+ T cell in the setting of HCC and facilitates increased proliferation and IFN-γ production in response to tumor antigen stimulation (FIG. 2). Consistent with our finding, a recent publication reports that conditioning of LCMV-infected mice with C8 ceramide enhances the T cell response to virus infection by promoting the expansion of virus-specific CD8+ T cells[37]. A previous study suggested that the ceramide-metabolizing enzyme acid sphingomyelinase plays an important role in T cell degranulation by increasing ceramide[38]. In contrast to this immune stimulatory activity, one group reported that exogenous addition of ceramide was reported to inhibit antigen uptake by dendritic cells (DCs) and impair their capability to stimulate Ag-specific T cells[39]. However, the DCs used in the study were prepared from healthy donors. These contradictory effects suggest that ceramides may differently impact immune response in healthy subjects and cancer patients.

Our data indicate that LipC6 activates antitumor immunity by targeting TAM through regulating ROS signaling. Our in vivo studies suggest that injection of TBMs with LipC6 results in the reduction of both the frequency of TAMs (FIGS. 3B-3D) and the expression of M2-like markers (FIG. 4) as well as the immunosuppressive function (FIG. 3). In vitro studies with BMMs validate that LipC6 can phenotypically (FIG. 7) and functionally (FIG. 6) modulate BMMs. Furthermore, addition of $H_2O_2$ blocks the LipC6-induced shift in macrophage phenotype from M2 to M1 (FIG. 7A); incubation of BMMs with LipC6 and NAC, a ROS-specific inhibitor, generates similar response profiles (FIG. 7B). These data suggest that macrophages are an important target of LipC6 and that ROS is a critical signal that is neutralized to overcome the effect of tumor-induced immunotolerance. Consistent with our findings, a recent report demonstrates that the continuous injection of the ROS inhibitor butylated hydroxyanisole (BHA) efficiently blocks the accumulation of TAMs and markedly suppresses tumorigenesis in lung cancer mouse models[22]. In particular, ROS production was shown to be important in M2 but not M1 macrophage differentiation. It also has been reported that ROS is a critical trigger of Cox-2-mediated macrophage differentiation from monocytes. Studies on oxidative stress-linked endotoxic shock suggest that NAC injection provides a therapeutic effect by modulating the function of macrophages and decreasing the production of ROS. Collectively, these results indicate that LipC6 functions as a ROS scavenger to alter macrophage functionality in the TME. In the present study, we noted a small but significant ROS change in TAMs from vehicle-injected TBMs. Vehicle contains an equal amount of lipid components in the same ratio as LipC6, except without ceramide. This finding is consistent with previous reports regarding the effect of liposomes on mouse liver macrophages[40]. However, it should be noted that in all circumstances this effect is less than LipC6 and not statistically significant. In fact, vehicle formulations did not change any of the other parameters measured in the current study.

Our present studies also showed that LipC6 reduced PD-L1 expression in TAMs, and neutralization of PD-1 in TILs with anti-PD-1 Abs increased IFN-γ production in TILs, suggesting PD-1 signaling may represent another mechanism through which LipC6 overcomes tumor-induced immune suppression. We recently demonstrated that a chemoimmunotherapy modality with combination of anti-PD-1 and a FDA-approved sunitinib, a tyrosine kinase inhibitor, strongly suppressed HCC growth[17]. Therefore, integration of LipC6 with anti-PD-1 or other kinds of immunotherapies is deserving of further evaluation for development of a clinically available therapeutic modality in HCC treatment.

REFERENCES

1. Forner A, Llovet J M, Bruix J. Hepatocellular carcinoma. Lancet 2012; 379:1245-55.
2. Gajewski T F, Schreiber H, Fu Y X. Innate and adaptive immune cells in the tumor microenvironment. Nat Immunol 2013; 14:1014-22.
3. Mueller K L. Cancer immunology and immunotherapy. Realizing the promise. Introduction. Science 2015; 348: 54-5.
4. Niu L Z, Li J L, Zeng J Y, et al. Combination treatment with comprehensive cryoablation and immunotherapy in metastatic hepatocellular cancer. World J Gastroenterol 2013; 19:3473-80.
5. Gajewski T F, Schumacher T. Cancer immunotherapy. Curr Opin Immunol 2013; 25:259-60.
6. Ribas A, Wolchok J D. Combining cancer immunotherapy and targeted therapy. Curr Opin Immunol 2013; 25:291-6.
7. Pembrolizumab superior to ipilimumab in melanoma. Cancer Discov 2015; 5:568.
8. Breous E, Thimme R. Potential of immunotherapy for hepatocellular carcinoma. J Hepatol 2011; 54:830-4.
9. Liu D, Staveley-O'Carroll K F, Li G. Immune-based Therapy Clinical Trials in Hepatocellular Carcinoma. J Clin Cell Immunol 2015; 6.
10. Schneider C, Teufel A, Yevsa T, et al. Adaptive immunity suppresses formation and progression of diethylnitrosamine-induced liver cancer. Gut 2012; 61:1733-43.
11. Greten T F, Wang X W, Korangy F. Current concepts of immune based treatments for patients with HCC: from basic science to novel treatment approaches. Gut 2015; 64:842-848.
12. Morad S A, Cabot M C. Ceramide-orchestrated signalling in cancer cells. Nat Rev Cancer 2013; 13:51-65.
13. Morales A, Lee H, Goni F M, et al. Sphingolipids and cell death. Apoptosis 2007; 12:923-39.
14. Pettus B J, Chalfant C E, Hannun Y A. Ceramide in apoptosis: an overview and current perspectives. Biochim Biophys Acta 2002; 1585:114-25.

15. Stoffel B, Bauer P, Nix M, et al. Ceramide-independent CD28 and TCR signaling but reduced IL-2 secretion in T cells of acid sphingomyelinase-deficient mice. Eur J Immunol 1998; 28:874-80.
16. Tagaram H R, Divittore N A, Barth B M, et al. Nanoliposomal ceramide prevents in vivo growth of hepatocellular carcinoma. Gut 2011; 60:695-701.
17. Li G, Liu D, Cooper T K, et al. Successful chemoimmunotherapy against hepatocellular cancer in a novel murine model. J Hepatol 2016.
18. Kester M, Bassler J, Fox T E, et al. Preclinical development of a C6-ceramide NanoLiposome, a novel sphingolipid therapeutic. Biol Chem 2015; 396:737-47.
19. Liu X, Ryland L, Yang J, et al. Targeting of survivin by nanoliposomal ceramide induces complete remission in a rat model of NK-LGL leukemia. Blood 2010; 116:4192-201.
20. Zolnik B S, Stern S T, Kaiser J M, et al. Rapid distribution of liposomal short-chain ceramide in vitro and in vivo. Drug Metab Dispos 2008; 36:1709-15.
21. Sica A, Invernizzi P, Mantovani A. Macrophage plasticity and polarization in liver homeostasis and pathology. Hepatology 2014; 59:2034-42.
22. Zhang Y, Choksi S, Chen K, et al. ROS play a critical role in the differentiation of alternatively activated macrophages and the occurrence of tumor-associated macrophages. Cell Res 2013; 23:898-914.
23. Held W A, Mullins J J, Kuhn N J, et al. T antigen expression and tumorigenesis in transgenic mice containing a mouse major urinary protein/SV40 T antigen hybrid gene. EMBO J 1989; 8:183-91.
24. Staveley-O'Carroll K, Schell T D, Jimenez M, et al. In vivo ligation of CD40 enhances priming against the endogenous tumor antigen and promotes CD8+ T cell effector function in SV40 T antigen transgenic mice. J Immunol 2003; 171:697-707.
25. Avella D M, Li G, Schell T D, et al. Regression of established hepatocellular carcinoma is induced by chemoimmunotherapy in an orthotopic murine model. Hepatology 2012; 55:141-52.
26. Duluc D, Delneste Y, Tan F, et al. Tumor-associated leukemia inhibitory factor and IL-6 skew monocyte differentiation into tumor-associated macrophage-like cells. Blood 2007; 110:4319-30.
27. Zou W. Immunosuppressive networks in the tumour environment and their therapeutic relevance. Nat Rev Cancer 2005; 5:263-74.
28. Fleetwood A J, Dinh H, Cook A D, et al. GM-CSF- and M-CSF-dependent macrophage phenotypes display differential dependence on type I interferon signaling. J Leukoc Biol 2009; 86:411-21.
29. Martinez F O, Gordon S, Locati M, et al. Transcriptional profiling of the human monocyte-to-macrophage differentiation and polarization: new molecules and patterns of gene expression. J Immunol 2006; 177:7303-11.
30. Emens L A. Chemoimmunotherapy. Cancer J 2010; 16:295-303.
31. Mapara M Y, Sykes M. Tolerance and cancer: mechanisms of tumor evasion and strategies for breaking tolerance. J Clin Oncol 2004; 22:1136-51.
32. Melief C J, Toes R E, Medema J P, et al. Strategies for immunotherapy of cancer. Adv Immunol 2000; 75:235-82.
33. Sharma P, Wagner K, Wolchok J D, et al. Novel cancer immunotherapy agents with survival benefit: recent successes and next steps. Nat Rev Cancer 2011; 11:805-12.
34. Spiegel S, Milstien S. The outs and the ins of sphingosine-1-phosphate in immunity. Nat Rev Immunol 2011; 11:403-15.
35. Watters R J, Fox T E, Tan S F, et al. Targeting glucosylceramide synthase synergizes with C6-ceramide nanoliposomes to induce apoptosis in natural killer cell leukemia. Leuk Lymphoma 2013; 54:1288-96.
36. Jiang Y, DiVittore N A, Kaiser J M, et al. Combinatorial therapies improve the therapeutic efficacy of nanoliposomal ceramide for pancreatic cancer. Cancer Biol Ther 2011; 12:574-85.
37. Pritzl C J, Seo Y J, Xia C, et al. A ceramide analogue stimulates dendritic cells to promote T cell responses upon virus infections. J Immunol 2015; 194:4339-49.
38. Herz J, Pardo J, Kashkar H, et al. Acid sphingomyelinase is a key regulator of cytotoxic granule secretion by primary T lymphocytes. Nat Immunol 2009; 10:761-8.
39. Sallusto F, Nicolo C, De Maria R, et al. Ceramide inhibits antigen uptake and presentation by dendritic cells. J Exp Med 1996; 184:2411-6.
40. Moghimi S M, Patel H M. Modulation of murine liver macrophage clearance of liposomes by diethylstilbestrol. The effect of vesicle surface charge and a role for the complement receptor Mac-1 (CD11b/CD18) of newly recruited macrophages in liposome recognition. J Control Release 2002; 78:55-65.

LIST OF ABBREVIATIONS

ACT Adoptive cell transfer
BMM Bone marrow-derived macrophage
BW Body weight
CFSE Carboxyfluorescein succinimidyl ester
CTLA-4 Cytotoxic T-lymphocyte-associated protein 4
DC Dendritic cell
FDA Food and Drug Administration
G-BMM GMCSF-induced bone marrow-derived macrophage
HCC Hepatocellular cancer
IL Interleukin
IND Investigational new drug
LipC6 Liposome-loaded C6-ceramide
LRL Liver-resident lymphocyte
M-BMM MCSF-induced bone marrow-derived macrophage
MDSC Myeloid derived suppressor cell
PD-1 Programmed death-1
RC Responder cell
ROS Reactive oxygen species
RT Room temperature
TAg SV40 T antigen
TBM Tumor-bearing mice
TAS Tumor antigen-specific
TCR T cell receptor
TILs Tumor-infiltrating leukocytes
Treg Regulatory T cell

What is claimed is:

1. A method of treating cancer, the method comprising administering to a subject in need of treatment of cancer, a) a composition comprising ceramide nanoliposome, wherein said ceramide nanoliposome comprises a C6, C8, C10 or C12 ceramide nanoliposome or a combination thereof;

b) a composition selected from the group consisting of:
  (i) a composition comprising tumor antigen specific T-cells;
  (ii) a composition comprising tumor antigen expressing cells;
  (iii) a composition comprising an antagonist of a Programmed Death 1 protein (PD-1); and
  (iv) any combination of (i)-(iii), wherein said compositions of (a) and (b) are administered such that tumor associated macrophages are converted from type M2 to type M1, and wherein immune response in said subject is increased compared to a subject not administered said composition,
thereby treating said cancer.

2. The method of claim 1, wherein said composition comprising said ceramide nanoliposome is administered prior to administering any one of said compositions of (i)-(iii) or combination thereof.

3. The method of claim 1, further comprising administering said composition comprising said ceramide nanoliposome more than once prior to administering one or more of said compositions of (i)-(iii) or combination thereof.

4. The method of claim 1, further comprising administering said composition comprising tumor antigen expressing cells more than once.

5. The method of claim 1, comprising administering said ceramide nanoliposome, administering said composition comprising tumor antigen specific T-cells, and administering a composition comprising tumor antigen expressing cells.

6. The method of claim 1, wherein said composition comprising tumor antigen expressing cells comprises cells expressing chimeric antigen receptor T cells (CAR-Ts).

7. The method of claim 1, wherein said cancer comprises hepatocellular cancer.

8. The method of claim 1, wherein said ceramide nanoliposome comprises C6 ceramide nanoliposome.

9. A kit comprising
a) a composition comprising ceramide nanoliposome, wherein said ceramide nanoliposome comprises a C6, C8, C10 or C12 ceramide nanoliposome or a combination thereof;
b) a composition selected from the group consisting of:
(i) a composition comprising tumor antigen specific T-cells;
(ii) a composition comprising tumor antigen expressing cells;
(iii) a composition comprising an antagonist of a Programmed Death 1 protein (PD-1); and
(iv) any combination of (i)-(iii);
wherein said kit is administered to a subject in need of treatment of cancer such that tumor associated macrophages are converted from type M2 to type M1, and wherein immune response in said subject is increased compared to a subject not administered said composition.

10. The method of claim 1 comprising administering said composition to a subject having said established cancer tumors.

11. The method of claim 10, wherein said cancer comprises hepatocellular cancer.

12. The method of claim 10, wherein said established cancer tumors are eradicated following said administration.

13. A method of increasing immune response by a subject to immunotherapy, the method comprising administering immunotherapy to said subject and administering a composition comprising ceramide nanoliposome, wherein said ceramide nanoliposome comprises a C6, C8, C10 or C12 ceramide nanoliposome or a combination thereof, wherein the immune response of said subject is increased compared to a subject administered said immunotherapy and not administered said compositions comprising said ceramide nanoliposome, and wherein tumor associate macrophages are converted from type M2 to type M1.

14. The method of claim 13, wherein said immunotherapy is selected from the group consisting of administering a composition comprising tumor antigen specific T-cells, administering a composition comprising tumor antigen expressing cells, administering a composition comprising an antagonist of a Programmed Death 1 protein (PD-1) or a combination thereof.

15. The method of claim 13, wherein said immunotherapy comprises an antagonist of PD-1 and the number of PD-1 binding sites are decreased after administration of said ceramide nanoliposome and said antagonist of PD-1.

16. A method of increased downregulation of a Programmed Death 1 protein (PD-1) in a subject, the method comprising administering a composition comprising a ceramide nanoliposome, wherein said ceramide nanoliposome comprises a C6, C8, C10 or C12 ceramide nanoliposome or a combination thereof, and wherein PD-1 downregulation is increased compared to a subject not administered said composition.

* * * * *

SEQUENCE LISTING

```
<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
```

```
<223> OTHER INFORMATION: Primer

<400> SEQUENCE: 1
aagtccctgc cctttgtaca ca                                           22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gcctcactaa accatccaat cg                                           22

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gacgagacgg ataggcagag                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gtggggttgt tgctgaactt                                              20

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
gaaagcctag aaagtctgaa taact                                        25

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
atcagcagcg actcctttc cgctt                                         25

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gaggacttga agatgtacca g                                            21
```

```
<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ttctatctgt gtgaggaggg c                                              21

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
acggcatgga tctcaaagac                                                20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gtgggtgagg agcacgtagt                                                20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
atggaagaga ccttcagcta c                                              21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
gctgtcttcc caagagttgg g                                              21

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
acaggagaag ggacgccat                                                 19

<210> SEQ ID NO 14
<211> LENGTH: 21
<212> TYPE: DNA
<213> ORGANISM: Artificial Sequence
<220> FEATURE:
<223> OTHER INFORMATION: Primer
```

<400> SEQUENCE: 14
gaagccctac agacgagctc a                                              21

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ttgcaactgc ctgtgcttac                                                20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
caagaagcag ggtaaatggg                                                20

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
agaagggagt ttcaaacctg gt                                             22

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
gtcttgctca tgtgtgtaag tga                                            23

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
cgactcgcaa ccacaccatt aag                                            23

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
tcctgcccca aagagcacaa g                                              21

<210> SEQ ID NO 21
<211> LENGTH: 20

```
<212> TYPE: DNA
<213> ORGANISM: Artificial Sequence
<220> FEATURE:
<223> OTHER INFORMATION: Primer

<400> SEQUENCE: 21
gcccatttac aaaggctcaa                                          20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tgttcctgtc aaagctcgtg                                          20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
cagaagctga ggtaatctgg a                                        21

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
tgagtcctgt tctgtggagg                                          20

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
ctggatagcc tttcttctgc tg                                       22

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gcacactgtg tccgaactca                                          20
```